(12) United States Patent
Kato et al.

(10) Patent No.: US 6,596,863 B2
(45) Date of Patent: Jul. 22, 2003

(54) MEDICAL COMPOSITION CONTAINING NITROETHENEAMINE DERIVATIVE OR SALT THERE OF AS ACTIVE CONSTITUENT

(75) Inventors: Fuminori Kato, Shiga (JP); Keizo Miyata, Shiga (JP); Hirohiko Kimura, Shiga (JP); Kazuhiro Yamamoto, Shiga (JP); Hiroyuki Ikegami, Shiga (JP); Hiromi Takeo, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 10/133,752

(22) Filed: Apr. 29, 2002

(65) Prior Publication Data

US 2002/0198184 A1 Dec. 26, 2002

Related U.S. Application Data

(62) Division of application No. 09/805,781, filed as application No. PCT/JP99/05148 on Sep. 21, 1999, now Pat. No. 6,451,792.

(30) Foreign Application Priority Data

Sep. 22, 1998 (JP) ............................. 10-286074
Dec. 28, 1998 (JP) ............................. 10-377076

(51) Int. Cl.$^7$ ................... C07D 213/76; C07D 231/38; C07D 333/22; C07D 213/42; C07C 311/49; C07C 323/37; C07C 323/48; C07C 213/38

(52) U.S. Cl. ................... 544/164; 564/94; 564/98; 564/148; 564/149; 564/271; 564/272; 564/273; 564/274; 564/275; 564/276; 564/277; 564/278; 564/279; 564/310; 564/313; 564/366; 564/372; 564/463; 564/464; 544/219; 544/326; 544/332; 544/356; 544/382; 546/114; 546/122; 546/162; 546/244; 546/261; 546/282.1; 546/283.4; 546/293; 546/297; 546/306; 546/332; 548/179; 548/222; 548/309.7; 548/365.5; 548/371.7; 549/75; 549/366; 549/437; 549/439; 549/495; 560/22; 562/437

(58) Field of Search ................... 544/164, 219, 544/326, 332, 356, 382; 546/114, 122, 162, 244, 261, 282.1, 283.4, 293, 297, 306, 332; 548/179, 222, 309.7, 356.5, 371.7; 549/75, 366, 437, 439, 495; 560/22; 562/437; 564/94, 98, 148, 149, 271–279, 310, 313, 366, 372, 463, 464

(56) References Cited

U.S. PATENT DOCUMENTS 4,098,898 A 7/1978 Durant et al.

OTHER PUBLICATIONS

Database CAPLUS on STN, Acc. No. 1991:514079, Tetrahedron (1991), 47(23), p. 3887–94 (abstract).*

Database CAPLUS on STN, Acc. No. 1977:72655, White, DE 2621092 (abstract).*

Schaefer et al, *J. Prakt. Chem.*, vol. 319, No. 1, pp. 149–158 (1977).

Database CAPLUS on STN, Acc. No. 1989:231447, Minamida et al, Alpha–unsaturated amines, particularly 1,1–diamino–2–nitroethylene derivatives, their insecticidal/miticidal compositions, and processes for their preparation. EP 302389 (Abstract).

Database CAPLUS on STN, Acc. No. 1977–468241, Schaeffer, "Cycliations with 1–nitro–2–anilinoethylenes" J. Prakt. Chem. (1977), 319(1) pp. 149–158 (abstract).

Maybhate et al, *Tetrahedron*, vol. 47, No. 23, pp. 3887–3894 (1991).

(List continued on next page.)

*Primary Examiner*—Brian Davis
(74) *Attorney, Agent, or Firm*—Oblon, Spivak, McClelland, Maier & Neustadt, P.C.

(57) ABSTRACT

Process for producing a nitroetheneamine derivative

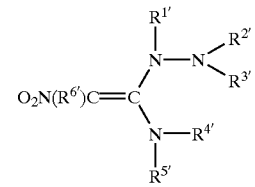

or its stereoisomer, its tautomer or a salt thereof comprising reacting a compound of the formula

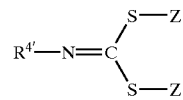

with a compound of the formula $R^6$—$CH_2NO_2$ to obtain a compound of the formula

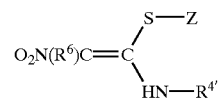

and reacting the resulting compound with a compound of the formula

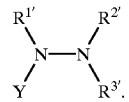

5 Claims, No Drawings

OTHER PUBLICATIONS

Sorba et al, *Arch. Pharm.,* vol. 317, No. 6. pp. 496–501 (1984).

Ishida et al, *Mol. Pharmacol.,* vol. 31, No. 4, pps. 410–416 (1987).

Quadri et al, *J. Med. Chem.,* vol. 39, No. 17, pp. 3385–3393 (1996).

Valli et al, *J. Med. Chem.,* vol. 35, No. 17, pp. 3141–3147 (1992).

* cited by examiner

MEDICAL COMPOSITION CONTAINING NITROETHENEAMINE DERIVATIVE OR SALT THERE OF AS ACTIVE CONSTITUENT

This application is a Division of application Ser. No. 09/805,781 Filed on Mar. 20, 2001, now U.S. Pat. No. 6,451,792 which is a 371 of PCT/JP99/05148, filed Sep. 21, 1999. Which was published in English.

TECHNICAL FIELD

The present invention relates to a medical composition containing a nitroetheneamine derivative or a salt thereof as an active constituent.

BACKGROUND ART

The present invention relates to a medical composition containing a nitroetheneamine derivative or a salt thereof as an active constituent, which has excellent matrix metalloproteinase inhibitory activities and which is useful as an angiogenesis inhibitor, an anticancer agent, a tumor cell infiltration inhibitor or a tumor metastasis inhibitor useful for treatment or prevention of cancer or inflammatory diseases, or as a therapeutic or preventive agent for an articular disease such as chronic articular rheumatism, osteoarthritis or rheumatoid arthritis, or as a therapeutic or preventive agent for various diseases such as gingivitis, glomerular nephritis, interstitial nephritis, encephalomyelitis, arterial sclerosis, cirrhosis, restenosis, diabetic retinopathy, neovascular glaucoma, corneal ulcer, epidermolysis bullosa, herniated disk, a bone resorption such as osteoporosis, multiple sclerosis, bronchial asthma, Alzheimer's disease or an autoimmune disorder (such as Crohn's disease or Sjögren's syndrome). Further, some of the nitroetheneamine derivatives and their salts which are active constituents of such medical compositions, are novel compounds, and the present invention relates also to such novel compounds.

Connective tissues of higher organisms are constituted by extracellular matrices. Extracellular matrices maintain homeostatis of biodynamic functions by repeating new formation and degradation (reassembly) depending upon the functions or morphological features of the particular tissues. Matrix metalloproteinases (MMP) are primary enzymes involved in the decomposition of extracellular matrices and characterized in that they have a bivalent zinc ion at the active center. Presence of about 20 types of MMP has been confirmed up to now including a secreted-type and a membrane-anchored-type, and the physiological functions and in-vivo distributions of the respective molecules are being made clear. MMP in a normal living body acts at a site where restructuring of tissues is required, for example, at a fetal development or for wound healing. However, in order to prevent destruction of extracellular matrices more than necessary, a strict regulation mechanism (regulation of expression or feedback regulation) is functioning. Namely, MMP is usually secreted as an inactive substance by external stimulation and then converted to an active substance by various proteases. On the other hand, the decomposition activities by MMP are controlled by TIMP (tissue inhibitor of metalloproteinase) as its endogenous inhibitor. However, if some abnormality occurs in the above control mechanism, and MMP becomes excessive, various tissue diseases will be induced.

For example, ① with respect to MMP-9 (gelatinase B/92 kDa type IV collagenase) having a strong decomposition activity against type IV collagen which is the main constituting component of a basement membrane, no substantial expression is usually observed in human normal tissues. On the other hand, its over expression has been observed in many epithelial cancer cells and hematopoletic cancer cells including cells of breast cancer and lung cancer. ② In carcinoma of the colon and rectum, a positive correlation has been observed between the expression level of MMP-9 and the metastatic nature (M. Nakajima et al, Journal of National Cancer Institute, Vol. 82, 1890, (1990)). ③ It has also been experimentally shown with respect to various cancer cells that the metastatic potential or infiltrating potential of cancer cells in which MMP-9 or MMP-2 (gelatinase A/72 kDa type IV collagenase) is highly expressed, is advanced as compared with cells in which such expression is low (D. R. Welch et al, Proceedings of the National Academy of Sciences of the United States of America, Vol. 87, 7687, (1990), S. Yamagata et al, Biochemical and Biophysical Research Communication, Vol. 151, 186–162 (1988)). ④ With respect to MMP-13 (collagenase 3), no expression has been observed in normal cells, but its high expression has been observed in breast cancer cells (J. M. Freiji, M. Nakajima et al, Journal of Biological Chemistry, Vol. 269, 16766–76773, (1994)).

Thus, highly malignant metastatic cancer cells have abnormal motility, adhesion and tissue invasive potential in addition to abnormal growth nature inherent to neoplasm, and as one of the background factors, excess production of MMP is involved.

Further, it is already known that ① MMP is involved in capillary-like tube formation of cultured vascular endothelial cells (R. Montesano et al, Cell, Vol. 42, 469–477, (1985)), ② MMP acts as one of angiogenesis factors to promote tumor growth (T. Itoh et al, Cancer Research, Vol. 58, 1048–1051, (1998) ), or ③ with melanoma cells wherein TIMP-2 is excessively expressed, the tissue-infiltration ability or the angiogenesis inducibility decreases (P. Valente et al, International Journal of Cancer, Vol. 75, 246–253 (1998)).

On the other hand, if inflammatory cytokine is induced by some factor at the joint region, and MMP-1 (interstitial collagenase) or MMP-3 (Stromelysin 1) from synovial cells is excessively produced and stored in a large amount in the joint fluid, it acts on the joint cartilage to destroy the cartilage matrix, thus leading to so-called articular diseases represented by symptoms such as pain, regulation of variable joint region or deformations.

Further, it is known that in a coronary disease, MMP will promote migration of smooth muscle cells from the vascular wall to the intima and will promote formation of atherosclerotic plaques, and further that it is involved in reconstruction after angioplasty in the anginal therapy (D. C. Celentano et al, Journal of Clinical Pharmacology, Vol. 37, 991–1000, (1997)).

Further, in gingivitis, an increase in the production of MMP-1 (interstitial collagenase) is observed.

Thus, MMP is responsible for a wide range of physiological functions in a living body, and its overproduction will upset the homeostasis of the living body and will induce a new disease or aggravation of pathology. Accordingly, a MMP inhibitor is considered to be useful as an angiogenesis inhibitor, an anticancer agent, a tumor cell infiltration inhibitor or a tumor metastasis inhibitor, to be used for treatment or prevention of cancer or inflammatory diseases; a therapeutic or preventive agent for an articular disease such as chronic articular rheumatism, osteoarthritis or rheumatoid arthritis; or as a therapeutic or preventive agent for various diseases such as gingivitis, glomerular nephritis, interstitial nephritis, encephalomyelitis, arterial sclerosis, cirrhosis, restenosis, diabetic retinopathy, neovascular glaucoma, corneal ulcer, epidermolysis bullosa, herniated disk, a bone resorption such as osteoporosis, multiple sclerosis, bronchial asthma, Alzheimer's disease or an autoimmune disorder (such as Crohn's disease or Sjögren's syndrome).

Heretofore, many compounds having MMP inhibition activities have been reported (R. A. Nigel et al, Current Opinion on Therapeutic Patents, Vol. 4, 7–16, (1994), R. P. Beckett et al, Drug Discovery Today, Vol. 1, 16–26, (1996)). However, most of them are peptide derivatives designed based on the amino acid sequence of the enzymatic cleavage site in the collagen molecule constituting the substrate of MMP, including, for example, hydroxamic acid type compounds; thiol type compounds; carboxylic acid type compounds; phosphonate type compounds; and phosphonate type compounds. Among them, with respect to some compounds including hydroxamic acid derivatives, clinical trial have been carried out on diseases such as cancer and arthritis.

It is generally known that a MMP inhibitor having a peptide in the basic structure has a low oral absorbance, and particularly, a hydroxamic acid type MMP inhibitor is considered to be poor in the stability in plasma, and a carboxylic acid type MMP inhibitor is known to have high affinity with plasma proteins and is hardly excreted. To overcome such problems, preparation of a new compound of non-peptide type has been attempted (A. Katrin et al, Journal of Medicinal Chemistry, Vol. 41, 2194–2200, (1998)). Recently, a MMP inhibitor containing, as an active constituent, a flavon or anthocyanisine as disclosed in JP-A-8-104628, or a condensed thiophene derivative type MMP inhibitor as disclosed in JP-A-10-130271, is known. However, it has not been known that a medical composition containing, as an active constituent, a non-peptide type nitroetheneamine derivative or a salt thereof like the present invention, has a MMP inhibition activity, particularly a strong and selective enzyme inhibition activity against MMP-9 (gelatinase B/92 kDa type IV collagenase).

Some of the nitroetheneamine derivatives as active constituents of medical compositions of the present invention are known compounds as disclosed in e.g. WO90/5134, JP-A-2-171, JP-A-3-255072, JP-A-3-204848, East German Patent 107276, East German Patent 107674, JP-A-8-277253 and WO97/17954. These known compounds are usually employed mainly as insecticides, but the compounds disclosed in WO97/17954 are employed as painkillers. However, WO97/17954 discloses some of nitroetheneamine derivatives used in the present invention, merely by wording. It is not known at all that the above-mentioned known compounds have MMP inhibition activities. Further, JP-B-58-404956 discloses compounds similar to nitroetheneamine derivatives used as active constituents in the medical compositions of the present invention, as intermediates for compounds useful as active constituents of medical compositions, but such compounds are distinguished from the nitroetheneamine derivatives in that they do not have leaving groups having a "N—N" structure. Further, in this publication, there is no such a disclosure that these compounds have MMP inhibition activities.

The present inventors have conducted an extensive study on the synthesis and the pharmacological activities of compounds having MMP inhibition activities, and as a result, have found nitroetheneamine derivatives or salts thereof which are useful as active constituents of the medical compositions of the present invention, particularly as non-peptide type compounds having strong and selective enzyme inhibition activities against MMP-9. Some of the nitroetheneamine derivatives or the salts thereof are novel compounds, and such novel compounds, the process for producing such novel compounds and the intermediates for the preparation of such novel compounds, are also included in the present invention.

DISCLOSURE OF THE INVENTION

Namely, the present invention relates to a medical composition containing, as an active constituent, a nitroetheneamine derivative represented by the formula (I):

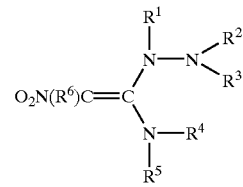

wherein
$R^1$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or a cyano group;

each of $R^2$ and $R^3$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or a —A—$R^7$ group (wherein A is S, SO, $SO_2$, $SO_3$, CO or $CO_2$, and $R^7$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted); or $R^2$ and $R^3$ may form, together with the N atom, a N=$CR^8R^9$ group (wherein each of $R^8$ and $R^9$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a cyano group, a nitro group, an alkoxy group which may be substituted, an alkylthio group which may be substituted, an aryloxy group which may be substituted or a —A—$R^7$ group (wherein A and $R^7$ are as defined above));

each of $R^4$ and $R^5$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an alkoxy group which may be substituted, a —A—$R^7$ group (wherein A and $R^7$ are as defined above), an amino group which may be substituted, a cyano group, an ester group, a hydroxyl group or an aryloxy group which may be substituted; or $R^4$ and $R^5$ may form, together with the N atom, a N=$CR^8R^9$ group (wherein $R^8$ and $R^9$ are as defined above);

$R^6$ is a hydrogen atom, a nitro group, a cyano group, a —A—$R^7$ group (wherein A and $R^7$ are as defined above), an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an alkoxy group which may be substituted, a halogen atom or an amino group which may be substituted; and further at least two selected from $R^1$, $R^2$, $R^3$, $R^4$ and $R^5$ may together form a ring containing or not containing a hetero atom;

or a salt thereof.

The salt of the nitroetheneamine derivative represented by the above formula (I) may be any pharmaceutically acceptable salt. For example, a mineral acid salt such as a hydrochloride, a sulfate or a nitrate; an organic acid salt such as a p-toluenesulfonate, a propanesulfonate or a methanesulfonate; an alkali metal salt such as a potassium salt or a sodium salt; an alkaline earth metal salt such as a calcium salt; or an organic amine salt such as a triethanolamine salt or a tris (hydroxymethyl) aminomethane salt, may be mentioned. Further, among these salts, there may be ones having water of crystallization.

The alkyl moiety in the alkyl group which may be substituted, contained in $R^1$, $R^2$, $R^3$, $R^4$, $R^5$, $R^6$, $R^7$, $R^8$ and $R^9$, in the alkoxy group which may be substituted, contained in $R^4$, $R^5$, $R^6$, $R^8$ and $R^9$, or in the alkylthio group which may be substituted, contained in $R^8$ and $R^9$ in the above formula (I), may usually be one having a carbon number of from 1 to 18, such as a methyl group, an ethyl group, a propyl group, a butyl group, a pentyl group, a hexyl group, an octyl group, a nonyl group, a decyl group or a nonadecyl group, and they include structural isomers of linear or branched aliphatic chains.

The alkenyl moiety of the alkenyl group which may be substituted, contained in $R^1$, $R^2$, $R^3$, $R^4$, $R^5$, $R^6$, $R^7$, $R^8$ and $R^9$ in the above formula (I), may be one having a carbon number of from 2 to 18, such as a vinyl group, a propenyl group, a butenyl group, a pentenyl group, a hexenyl group, a decenyl group or a nonadecenyl group, and they include structural isomers of linear or branched aliphatic chains.

The alkynyl moiety of the alkynyl group which may be substituted, contained in $R^1$, $R^2$, $R^3$, $R^4$, $R^5$, $R^6$, $R^7$, $R^8$ and $R^9$ in the above formula (I), may be one having a carbon number of from 2 to 18, such as an ethynyl group, a propynyl group, a butynyl group, a pentynyl group, a hexynyl group, a decynyl group or a nonadecynyl group, and they include structural isomers of linear or branched aliphatic chains.

The cycloalkyl moiety of the cycloalkyl group which may be substituted, contained in $R^1$, $R^2$, $R^3$, $R^4$, $R^5$, $R^6$, $R^7$, $R^8$ and $R^9$ in the above formula (I), may be one having a carbon number of from 3 to 8, such as a cyclopropyl group, a cyclobutyl group, a cyclopentyl group, a cyclohexyl group or a cyclooctyl group.

The cycloalkenyl moiety of the cycloalkenyl group which may be substituted, contained in $R^1$, $R^2$, $R^3$, $R^4$, $R^5$, $R^6$, $R^7$, $R^8$ and $R^9$ in the above formula (I), may be one having a carbon number of from 5 to 8, such as a cyclopentenyl group, a cyclohexenyl group or a cyclooctenyl group.

The aryl moiety in the aryl group which may be substituted, contained in $R^1$, $R^2$, $R^3$, $R^4$, $R^5$, $R^6$, $R^7$, $R^8$ and $R^9$, or in the aryloxy group which may be substituted, contained in $R^4$, $R^5$, $R^8$ and $R^9$, in the above formula (I), may, for example, be a phenyl group, a naphthyl group, a tetrahydronaphthyl group, an indanyl group, an adamanthyl group, a noradamanthyl group, a norbornanyl group or a norbornanonyl group.

The heterocyclic moiety in the heterocyclic group which may be substituted, contained in $R^1$, $R^2$, $R^3$, $R^4$, $R^5$, $R^6$, $R^7$, $R^8$ and $R^9$ in the above formula (I), may, for example, be a mononuclear heterocyclic group such as a pyrrolyl group, pyrrolinyl group, a pyrrolidinyl group, a furanyl group, a dihydrofuranyl group, a tetrahydrofuranyl group, a thienyl group, a dihydrodithienyl group, a tetrahydrothienyl group, a pyrazolyl group, a pyrazolinyl group, a pyrazolidinyl group, an imidazolyl group, an imidazolinyl group, an imidazolidinyl group, an oxazolyl group, an oxazolinyl group, an oxazolidinyl group, an isoxazolyl group, an isoxazolinyl group, an isoxazolidinyl group, a thiazolyl group, a thiazolinyl group, a thiazolidinyl group, an isothiazolyl group, an isothiazolinyl group, an isothiazolidinyl group, an oxadiazolyl group, an oxadiazolinyl group, an oxadiazolidinyl group, a thiadiazolyl group, a thiadiazolinyl group, a thiadiazolidinyl group, a triazolyl group, a triazolinyl group, a triazolidinyl group, a tetrazolyl group, a tetrazolinyl group, a tetrazolidinyl group, a dioxolyl group, a dioxolanyl group, a dithiolyl group, a dithiolanyl group, a pyridyl group, a dihydropyridyl group, a tetrahydropyridyl group, a piperidinyl group, a pyrimidyl group, a dihydropyrimidyl group, a tetrahydropyrimidyl group, a hexahydropyrimidyl group, a pyridazinyl group, a dihydropyridazinyl group, a tetrahydropyridazinyl group, a hexahydropyridazinyl group, a pyrazinyl group, a dihydropyrazinyl group, a tetrahydropyrazinyl group, a piperazinyl group, a pyranyl group, a dihydropyranyl group, a tetrahydropyranyl group, a dioxynyl group, a dioxenyl group, a dioxanyl group, a dithianyl group or a morpholyl group; a condensed type polynuclear heterocyclic group such as a thienothienyl group, a dihydrocyclopentathienyl group, an indolyl group, a tetrahydroindolyl group, an isoindolyl group, a tetrahydroisoindolyl group, a benzothienyl group, a tetrahydrobenzothienyl group, a benzofuranyl group, a tetrahydrobenzofuranyl group, a benzoxazolyl group, a tetrahydrobenzoxazolyl group, a benzoisoxazolyl group, a tetrahydrobenzoisoxazolyl group, a benzothiazolyl group, a tetrahydrobenzothiazolyl group, a benzoisothiazolyl group, a tetrahydrobenzoisothiazolyl group, a benzoimidazolyl group, a tetrahydrobenzoimidazolyl group, a benzodioxolyl group, a benzodithiolyl group, a benzodioxanyl group, a benzodithianyl group, a quinolyl group, an isoquinolyl group, a quinazolinyl group, a quinoxalinyl group, a phthalazinyl group, a naphthylidinyl group or a purinyl group; or a crosslinked type polynuclear heterocyclic ring such as a quinuclidinyl group.

The substituent(s) for the alkyl group which may be substituted, the alkenyl group which may be substituted and the alkynyl group which may be substituted, contained in $R^1$, $R^2$, $R^3$, $R^4$, $R^5$, $R^6$, $R^7$, $R^8$ and $R^9$ in the above formula (I); for the amino group which may be substituted, contained in $R^2$, $R^3$, $R^4$, $R^5$ and $R^6$; for the carbonyl group which may be substituted, contained in $R^8$ and $R^9$; for the alkoxy group which may be substituted, contained in $R^4$, $R^5$, $R^6$, $R^8$ and $R^9$; and for the alkylthio group which may be substituted, contained in $R^8$ and $R^9$, may, for example, be a halogen atom, an alkoxy group, a haloalkoxy group, an alkylthio group, an alkenyloxy group, an alkynyloxy group, an alkenylthio group, an alkynylthio group, a cycloalkyl group, a cycloalkoxy group, a cycloalkenyl group, a cycloalkenyloxy group, a cycloalkylthio group, a cycloalkenylthio group, an alkoxycarbonyl group, an alkylcarbonyl group, an alkylcarbonyloxy group, an alkenyloxycarbonyl group, an alkynyloxycarbonyl group, an aryloxycarbonyl group, a heteroaryloxycarbonyl group, an alkenylcarbonyl group, an alkynylcarbonyl group, an arylcarbonyl group, a heteroarylcarbonyl group, an alkenylcarbonyloxy group, an alkynylcarbonyloxy group, an arylcarbonyloxy group, a heteroarylcarbonyloxy group, an aryl group, a heteroaryl group, an aryloxy group, an arylthio group, an amino group, an amino group which is substituted by an alkyl group, an amino group which is substituted by an alkenyl group, an amino group which is substituted by an alkynyl group, an amino group which is substituted by a cycloalkyl group, an amino group which is substituted by a cycloalkenyl group, an amino group which is substituted by an aryl group, an amino group which is substituted by a heteroaryl group, an amino group which is substituted by a n acyl group, an amino group which is substituted by an alkylsulfonyl group, an amino group which is substituted by an arylsulfonyl group, an amino group which is substituted by a heteroarylsulfonyl group, a cyano group, an acyl group, a nitro group, a carboxyl group, an aminocarbonyl group, a hydroxyaminocarbonyl group, a sulfonyl group, an alkylsulfonyl group, an arylsulfonyl group and a heteroarylsulfonyl group. The number of such substituent(s) or substituent(s) of such substituent(s) may be one or two or more, and such substituents may be the same or different.

The substituent(s) for the cycloalkyl group which may be substituted, the cycloalkenyl group which may be substituted, the aryl group which may be substituted and the heterocyclic group which may be substituted, contained in $R^1$, $R^2$, $R^3$, $R^4$, $R^5$, $R^6$, $R^7$, $R^8$ and $R^9$ in the above formula (I), and for the aryloxy group which may be substituted, contained in $R^4$, $R^5$, $R^8$ and $R^9$, may, for example, be a halogen atom, an alkyl group, a haloalkyl group, an alkenyl group, an alkynyl group, a heteroaryl group, an alkoxy group, a haloalkoxy group, an alkoxyalkoxy group, an alkylthio group, an alkenyloxy group, an alkynyloxy group, an alkenylthio group, an alkynylthio group, a cycloalkyl group, a cycloalkoxy group, a cycloalkenyl group, a cycloalkenyloxy group, a cycloalkylthio group, a cycloalkenylthio group, an alkoxycarbonyl group, an alkylcarbonyl group, an alkylcarbonyloxy group, an alkenyloxycarbonyl group, an alkynyloxycarbonyl group, an aryloxycarbonyl group, a heteroaryloxycarbonyl group, an alkenylcarbonyl group, an alkynylcarbonyl group, an arylcarbonyl group, a heteroarylcarbonyl group, an alkenylcarbonyloxy group, an alkynylcarbonyloxy group, an arylcarbonyloxy group, a heteroarylcarbonyloxy group, an aryl group, an aryloxy group, a heteroaryloxy group, an arylthio group, a heteroarylthio group, an amino group, an amino group which is substituted by an alkyl group, an amino group which is substituted by an alkenyl group, an amino group which is substituted by an alkynyl group, an amino group which is substituted by a cycloalkyl group, an amino group which is substituted by a cycloalkenyl group, an amino group which is substituted by a n aryl group, an amino group which is substituted by a heteroaryl group, an amino group which is substituted by an acyl group, an amino group which is substituted by an alkylsulfonyl group, an amino group which is substituted by an arylsulfonyl group, an amino group which is substituted by a heteroarylsulfonyl group, a cyano group, an acyl group, a nitro group, a carboxyl group, an aminocarbonyl group, a hydroxyaminocarbonyl group, a sulfonyl group, an alkylsulfonyl group, an arylsulfonyl group, a heteroarylsulfonyl group and an arylalkyl group. The number of such substituent(s) or substituent(s) attached to such substituent(s) may be one or two or more, and such substituents may be the same or different.

Among the compounds represented by the above formula (I) or salts thereof, a nitroetheneamine derivative represented by the formula (I-1):

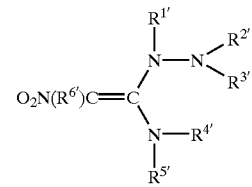

wherein $R^{1'}$ is a hydrogen atom, an alkyl group which may be substituted, an alkenyl group which may be substituted, an alkynyl group which may be substituted, a cycloalkyl group which may be substituted, a cycloalkenyl group which may be substituted or a cyano group;

each of $R^{2'}$ and $R^{3'}$ which are independent of each other, is a hydrogen atom, an alkyl group which may be substituted (provided that a heterocyclic methyl group which may be substituted, is excluded), a cycloalkyl group which may be substituted, a cycloalkenyl group which may be substituted, an aryl group which may be substituted, a heterocyclic group which may be substituted or a —A'—$R^{7'}$ group (wherein A' is S, SO, $SO_2$, $SO_3$, CO or $CO_2$, and $R^{7'}$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted); or $R^{2'}$ and $R^{3'}$ may form, together with the N atom, a N=$CR^{8'}R^{9'}$ group (wherein each of $R^{8'}$ and $R^{9'}$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a cyano group, a nitro group, an alkoxy group which may be substituted, an aryloxy group which may be substituted or a —A'—$R^{7'}$ group (wherein A' and $R^{7'}$ are as defined above));

$R^{4'}$ is an alkyl group which may be substituted, a cycloalkyl group which may be substituted, a cycloalkenyl group which may be substituted, an aryl group which may be substituted, an alkoxy group which may be substituted, a —A'—$R^{7'}$ group (wherein A' and $R^{7'}$ are as defined above) or an amino group which may be substituted;

$R^{5'}$ is a hydrogen atom, an alkyl group which may be substituted, a cycloalkyl group which may be substituted, a cycloalkenyl group which may be substituted, an aryl group which may be substituted, an alkoxy group which may be substituted, a —A'—$R^{7'}$ group (wherein A' and $R^{7'}$ are as defined above) or an amino group which may be substituted; or $R^{4'}$ and $R^{5'}$ may form, together with the N atom, a $N=CR^{8'}R^{9'}$ group (wherein $R^{8'}$ and $R^{9'}$ are as defined above);

$R^{6'}$ is a hydrogen atom, a nitro group, a cyano group, a —A'—$R^{7'}$ group (wherein A' and $R^{7'}$ are as defined above), an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an alkoxy group which may be substituted, a halogen atom or an amino group which may be substituted; and further at least two selected from $R^{1'}$, $R^{2'}$, $R^{3'}$, $R^{4'}$ and $R^{5'}$ may together form a ring containing or not containing a hetero atom;

provided that (1) a case where $R^{1'}$ or $R^{4'}$ is an alkyl group substituted by a hetero-ring which may be substituted, (2) a case where $R^{1'}$, $R^{2'}$, $R^{3'}$, $R^{5'}$ and $R^{6'}$ are all hydrogen atoms and $R^{4'}$ is

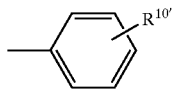

(wherein $R^{10'}$ is a hydrogen atom, a halogen atom, an alkyl group, an alkoxy group or a dialkylamino group) and (3) a case where $R^{1'}$, $R^{3'}$, $R^{5'}$ and $R^{6'}$ are all hydrogen atoms, and $R^{2'}$ is a hydrogen atom, an alkyl group which may be substituted or an aryl group which may be substituted, and $R^{4'}$ is

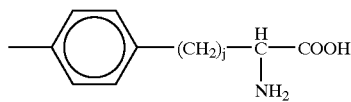

(wherein j is an integer of from 1 to 6), are excluded; or a salt thereof, is a compound which heretofore has not specifically been known.

Among the nitroetheneamine derivatives represented by the above formula (I-1) or salts thereof, as compounds which heretofore have not specifically been known, a nitroetheneamine derivative wherein $R^{1'}$ is a hydrogen atom, an alkyl group which may be substituted, an alkenyl group which may be substituted, an alkynyl group which may be substituted, a cycloalkyl group which may be substituted, a cycloalkenyl group which may be substituted or a cyano group;

each of $R^{2'}$ and $R^{3'}$ which are independent of each other, is a hydrogen atom, an alkyl group which may be substituted (provided that a heterocyclic methyl group which may be substituted, is excluded), a cycloalkyl group which may be substituted, a cycloalkenyl group which may be substituted, a heterocyclic group which may be substituted or a —A'—$R^{7'}$ group (wherein A' is S, SO, $SO_2$, $SO_3$, CO or $CO_2$, and $R^{7'}$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted); or $R^{2'}$ and $R^{3'}$ may form, together with the N atom, a $N=CR^{8''}R^{9''}$ group (wherein each of $R^{8''}$ and $R^{9''}$ which are independent of each other, is a hydrogen atom, an alkyl group which may be substituted, an aryl group which may be substituted, a heterocyclic group which may be substituted or an alkoxy group which may be substituted);

$R^{4'}$ is an alkyl group which may be substituted, an alkoxyphenyl group, a haloalkyloxyphenyl group, a cycloalkyl group which may be substituted, a cycloalkenyl group which may be substituted, an alkoxy group which may be substituted, a —A'—$R^{7'}$ group (wherein A' and $R^{7'}$ are as defined above) or an amino group which may be substituted;

$R^{5'}$ is a hydrogen atom, an alkyl group, an alkoxyphenyl group, a haloalkyloxyphenyl group, a cycloalkyl group which may be substituted, a cycloalkenyl group which may be substituted, an alkoxy group which may be substituted, a —A'—$R^{7'}$ group (wherein A' and $R^{7'}$ are as defined above) or an amino group which may be substituted;

$R^{6'}$ is a hydrogen atom, a nitro group, a cyano group or a —A'—$R^{7'}$ group (wherein A' and $R^{7'}$ are as defined above) or an alkyl group which may be substituted;

or $R^{4'}$ and $R^{5'}$ may form, together with the N atom, a $N=CR^{8''}R^{9''}$ group (wherein $R^{8''}$ and $R^{9''}$ are as defined above); and further at least two selected from $R^{1'}$, $R^{2'}$, $R^{3'}$, $R^{4'}$ and $R^{5'}$ may together form a ring containing or not containing a hetero atom;

provided that (1) a case where $R^{1'}$ or $R^{4'}$ is an alkyl group substituted by a hetero-ring which may be substituted, (2) a case where $R^{1'}$, $R^{3'}$, $R^{5'}$ and $R^{6'}$ are all hydrogen atoms, $R^{2'}$ is a hydrogen atom, an alkyl group which may be substituted or an aryl group which may be substituted, and $R^{4'}$ is

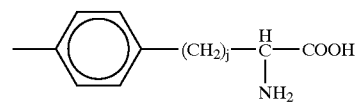

(wherein j is an integer of from 1 to 6), and (3) a case wherein $R^{1'}$ is a hydrogen atom; each of $R^{2'}$ and $R^{3'}$ which are independent of each other, is a hydrogen atom, an alkyl group which may be substituted or a phenyl group which may be substituted; $R^{4'}$ is an alkyl which may be substituted, a phenyl group which may be substituted, a —A'—$R^{7'}$ group (wherein A' and $R^{7'}$ are as defined above) or an amino group which may be substituted; $R^{5'}$ is a hydrogen atom, an alkyl group which may be substituted or a phenyl group which may be substituted; and $R^{6'}$ is a hydrogen atom, are excluded;

or a salt thereof, is a preferred compound.

Among the above-mentioned preferred compounds of the formula (I-1), a nitroetheneamine derivative wherein $R^{1'}$ is a hydrogen atom; $R^{2'}$ is a hydrogen atom, a heterocyclic group which may be substituted or a —A''—$R^{7''}$ group (wherein A'' is CO, $CO_2$ or $SO_2$, and $R^{7''}$ is an alkyl group which may be substituted or an aryl group which may be substituted); $R^{3'}$ is a hydrogen atom, an alkyl group which may be substituted (provided that a heterocyclic methyl group which may be substituted, is excluded), a heterocyclic group which may be substituted or a —A''—$R^{7''}$ group (wherein A'' and $R^{7''}$ are as defined above); or $R^{2'}$ and $R^{3'}$ may together form, a N=CR$^{8"}$R$^{9"}$ group (wherein each of R$^{8"}$ and R$^{9"}$ which are independent of each other, is a hydrogen atom, an alkyl group which may be substituted, an aryl group which may be substituted, a heterocyclic group which may be substituted or an alkoxy group which may be substituted); R$^{4'}$ is an alkyl group which may be substituted (provided that a heterocyclic alkyl group which may be substituted, is excluded), an alkoxyphenyl group, a haloalkyloxyphenyl group, a cycloalkyl group which may be substituted, an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted, a sulfonyl group substituted by a hetero ring which may be substituted or an amino group which may be substituted; R$^{5'}$ is a hydrogen atom; R$^{6'}$ is a hydrogen atom or an alkyl group; and further R$^{2'}$ and R$^{3'}$ may together form a ring containing or not containing a hetero atom; provided that (1) a case where R$^{1'}$, R$^{2'}$, R$^{5'}$ and R$^{6'}$ are hydrogen atoms; R$^{3'}$ is a hydrogen atom or an alkyl group which may be substituted; R$^{4'}$ is an alkyl which may be substituted, an alkoxyphenyl group which may be substituted, a haloalkyloxyphenyl group which may be substituted, an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted or a sulfonyl group substituted by a hetero ring which may be substituted, and (2) a case where R$^{1'}$, R$^{3'}$, R$^{5'}$ and R$^{6'}$ are hydrogen atoms, R$^{2'}$ is a heterocyclic group (provided that a heterocyclic group substituted by at least one halogen atom, is excluded), and R$^{4'}$ is an alkyl group which may be substituted, are excluded; or a salt thereof, is a novel compound.

The above novel compound is a compound particularly excellent as an active constituent for a matrix metalloproteinase inhibitor and can be used as an active constituent for a medical composition such as ① an inhibitor against at least one matrix metalloproteinase selected from MMP-1, MMP-2, MMP-3, MMP-7 and MMP-9, particularly a MMP-9 inhibitor; ② an angiogenesis inhibitor; ③ an anticancer drug; ④ a tumor cell infiltration inhibitor; ⑤ a tumor metastatis inhibitor; or ⑥ a therapeutic or preventive agent for rheumatoid arthritis. Among these novel compounds, the following compounds are particularly excellent as active constituents for matrix metalloproteinase inhibitors.

(1) A nitroetheneamine derivative of the above formula (I-1), wherein R$^{1'}$ is a hydrogen atom; R$^{2'}$ is a heterocyclic group which may be substituted or a —A"—R$^{7"}$ group (wherein A" is CO, CO$_2$ or SO$_2$, and R$^{7"}$ is an alkyl group which may be substituted or an aryl group which may be substituted); R$^{3'}$ is a hydrogen atom, an alkyl group which may be substituted (provided that a heterocyclic methyl group which may be substituted, is excluded), a heterocyclic group which may be substituted or a —A"—R$^{7"}$ group (wherein A" and R$^{7"}$ are as defined above); or R$^{2'}$ and R$^{3'}$ may together form a N=CR$^{8"}$R$^{9"}$ group (wherein each of R$^{8"}$ and R$^{9"}$ which are independent of each other, is a hydrogen atom, an alkyl group which may be substituted, an aryl group which may be substituted, a heterocyclic group which may be substituted or an alkoxy group which may be substituted) or form a ring containing or not containing a hetero atom; R$^{4'}$ is an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted, a sulfonyl group substituted by a hetero ring which may be substituted or an amino group which may be substituted; R$^{5'}$ is a hydrogen atom; and R$^{6'}$ is a hydrogen atom or an alkyl group; or a salt thereof.

(2) A nitroetheneamine derivative of the above formula (I-1), wherein R$^{1'}$ is a hydrogen atom; R$^{2'}$ is a heterocyclic group which may be substituted or a —A"—R$^{7"}$ group (wherein A" is CO, CO$_2$ or SO$_2$, and R$^{7"}$ is an alkyl group which may be substituted or an aryl group which may be substituted); R$^{3'}$ is a hydrogen atom, an alkyl group which may be substituted (provided that a heterocyclic methyl group which may be substituted, is excluded), a heterocyclic group which may be substituted or a —A"—R$^{7"}$ group (wherein A" and R$^{7"}$ are as defined above); or R$^{2'}$ and R$^{3'}$ may together form a N=CR$^{8"}$R$^{9"}$ group (wherein each of R$^{8"}$ and R$^{9"}$ which are independent of each other, is a hydrogen atom, an alkyl group which may be substituted, an aryl group which may be substituted, a heterocyclic group which may be substituted or an alkoxy group which may be substituted); R$^{4'}$ is an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted, a sulfonyl group substituted by a hetero ring which may be substituted or an amino group which may be substituted; R$^{5'}$ is a hydrogen atom; and R$^{6'}$ is a hydrogen atom or an alkyl group; or a salt thereof.

(3) A nitroetheneamine derivative of the above formula (I-1), wherein R$^{1'}$ is a hydrogen atom; R$^{2'}$ is a heterocyclic group which may be substituted or a —A"—R$^{7"}$ group (wherein A" is CO, CO$_2$ or SO$_2$, and R$^{7"}$ is an alkyl group which may be substituted or an aryl group which may be substituted); R$^{3'}$ is a hydrogen atom, an alkyl group which may be substituted (provided that a heterocyclic methyl group which may be substituted, is excluded), a heterocyclic group which may be substituted or a —A"—R$^{7"}$ group (wherein A" and R$^{7"}$ are as defined above); or R$^{2'}$ and R$^{3'}$ may together form a N=CR$^{8"}$R$^{9"}$ group (wherein each of R$^{8"}$ and R$^{9"}$ which are independent of each other, is a hydrogen atom, an alkyl group which may be substituted, an aryl group which may be substituted, a heterocyclic group which may be substituted or an alkoxy group which may be substituted); R$^{4'}$ is an alkylsulfonyl group which may be substituted, an arylsulfonyl group which may be substituted, or an amino group which may be substituted; R$^{5'}$ is a hydrogen atom; and R$^{6'}$ is a hydrogen atom or an alkyl group; or a salt thereof.

(4) A nitroetheneamine derivative of the above formula (I-1), wherein R$^{1'}$ is a hydrogen atom; R$^{2'}$ is a heterocyclic group which may be substituted or a —A"—R$^{7"}$ group (wherein A" is CO, CO$_2$ or SO$_2$, and R$^{7"}$ is an alkyl group which may be substituted or an aryl group which may be substituted); R$^{3'}$ is a hydrogen atom or methyl; or R$^{2'}$ and R$^{3'}$ may together form a N=CR$^{8"}$R$^{9"}$ group (wherein each of R$^{8"}$ and R$^{9"}$ which are independent of each other, is a hydrogen atom, an alkyl group which may be substituted, an aryl group which may be substituted, a heterocyclic group which may be substituted or an alkoxy group which may be substituted); $R^{4'}$ is an alkylsulfonyl group which may be substituted, an arylsulfonyl group which may be substituted, or an amino group which may be substituted; $R^{5'}$ is a hydrogen atom; and $R^{6'}$ is a hydrogen atom or an alkyl group; or a salt thereof.

(5) A nitroetheneamine derivative of the formula (I-1), wherein $R^{1'}$ is a hydrogen atom; $R^{2'}$ and $R^{3'}$ may together form a ring containing or not containing a hetero atom; $R^{4'}$ is an alkyl group which may be substituted, an alkoxyphenyl group, a haloalkyloxyphenyl group, a cycloalkyl group which may be substituted, an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted or a sulfonyl group substituted by a hetero ring which may be substituted; $R^{5'}$ is a hydrogen atom; and $R^{6'}$ is a hydrogen atom or an alkyl group; or a salt thereof.

(6) A nitroetheneamine derivative of the formula (I-1), wherein $R^{1'}$ is a hydrogen atom; $R^{2'}$ and $R^{3'}$ may together form a ring containing or not containing a hetero atom; $R^{4'}$ is an alkylsulfonyl group which may be substituted or an arylsulfonyl group which may be substituted; $R^{5'}$ is a hydrogen atom; and $R^{6'}$ is a hydrogen atom or an alkyl group; or a salt thereof.

The compound of the above formula (I) or a salt thereof can be produced by a known process for producing similar compounds (such as the process disclosed in JP-A-2-171) or a process similar thereto. However, as preferred embodiments, the following processes 1 to 12 may be exemplified.

(1) Process 1

A process for producing a nitroetheneamine derivative of the above formula (I), which comprises:

(1) a first step of reacting a compound represented by the formula (II):

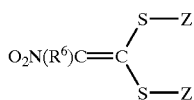

wherein Z is an alkyl group or an arylalkyl group, and $R^6$ is as defined above, with a compound represented by the formula (III):

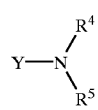

wherein Y is hydrogen or an alkali metal element, and $R^4$ and $R^5$ are as defined above, to obtain a compound represented by the formula (IV):

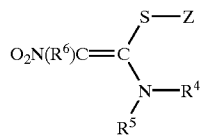

wherein Z, $R^4$, $R^5$ and $R^6$ are as defined above, and (2) a second step of reacting the compound of the above formula (IV) obtained in the first step, with a compound represented by the formula (V):

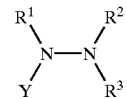

wherein Y is hydrogen or an alkali metal element, and $R^1$, $R^2$ and $R^3$ are as defined above, to obtain a nitroetheneamine derivative of the above formula (I).

(2) Process 2

A process for producing a nitroetheneamine derivative of the above formula (I), which comprises:

(1) a first step of reacting a compound of the above formula (II) with a compound of the above formula (V) to obtain a compound of the formula (VI):

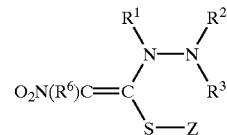

wherein Z, $R^1$, $R^2{}_1$, $R^3$ and $R^6$ are as defined above, and (2) a second step of reacting the above compound of the above formula (VI) obtained in the first step, with a compound of the formula (III) to obtain a nitroetheneamine derivative of the above formula (I).

Here, the compound of the above formula (II) and the compound of the above formula (III) as the starting materials for Process 1 and Process 2 can be produced by known processes or processes similar thereto.

The respective reactions in Process 1 and Process 2 can be carried out in the presence of a suitable solvent. The solvent to be specifically used, may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In order to carry out the respective reactions in Process 1 and Process 2 efficiently, it is preferred to carry out the reactions in the presence of a base. The base to be specifically used, may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide. Further, the compound of the above formula (III) and/or the compound of the above formula (V) will also act as a base.

The respective reactions in Process 1 and Process 2 are carried out usually at a reaction temperature of from −30 to 1500° C., preferably at a reaction temperature of from 0 to 1000° C. The reaction time is usually from 0.1 to 48 hours.

In the first step of Process 1, the compound of the above formula (III) can be used in an amount of from 1 to 1.2 equivalents per mol of the compound of the above formula (II). If the compound of the above formula (III) is used excessively, in addition to the compound of the above formula (IV), a compound represented by the formula (VII):

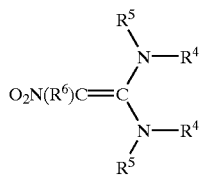

wherein $R^4$, $R^5$ and $R^6$ are as defined above, will be formed as a by-product, such being undesirable. Further, in the second step of Process 1, the compound of the above formula (V) can be used in an amount of from 1 to 1.5 equivalents per mol of the compound of the above formula (IV), but it may be used excessively without any particular problem.

In the first step of Process 2, the compound of the above formula (V) can be used in an amount of from 1 to 1.2 equivalents per mol of the compound of the above formula (II). If the compound of the above formula (V) is used excessively, in addition to the compound of the above formula (VI), a compound represented by the formula (VIII):

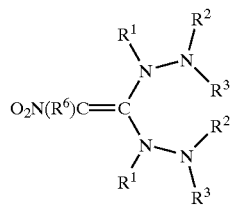

wherein $R^1$, $R^2$, $R^3$ and $R^6$ are as defined above, will be produced as a by-product, such being undesirable. Further, in the second step of Process 2, the compound of the above formula (III) can be used in an amount of from 1 to 1.5 equivalents per mol of the compound of the above formula (VI), but it may be used excessively without any particular problem.

The compound of the above formula (IV) obtained in Process 1 and the compound of the above formula (VI) obtained in Process 2, may be supplied to the subsequent reaction for producing a compound of the above formula (I) directly in the form of the reaction mixture or after separation and purification by a known means such as concentration, concentration under reduced pressure, solvent extraction, recrystallization or chromatography.

Various reaction conditions in Process 1 i.e. (1) the type and/or the amount of the compound of the above formula (II), (2) the type and/or the amount of the compound of the above formula (III), (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature in the first step, (8) the reaction time in the first step, (9) the type of the compound of the above formula (IV) as an intermediate product in the first step, (10) with or without separation and purification of the compound of the above formula (IV), (11) the type and/or the amount of the compound of the formula (V), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature in the reaction of the second step, (17) the reaction time in the reaction of the second step, and (18) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above-mentioned various reaction conditions are also in the scope of Process 1.

Various reaction conditions in Process 2 i.e. (1) the type and/or the amount of the compound of the above formula (II), (2) the type and/or the amount of the compound of the above formula (V), (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature in the first step, (8) the reaction time in the first step, (9) the type of the compound of the above formula (VI) as an intermediate product in the first step, (10) with or without separation and purification of the compound of the above formula (VI), (11) the type and/or the amount of the compound of the formula (III), (12) with or without use of a solvent in the reaction of the second step, (13) the type and/or the amount of the solvent in the reaction of the second step, (14) with or without use of a base in the reaction of the second step, (15) the type and/or the amount of a base in the reaction of the second step, (16) the reaction temperature in the reaction of the second step, (17) the reaction time in the reaction of the second step, and (18) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also in the scope of Process 2.

(3) Process 3

A process for producing a nitroetheneamine derivative of the above formula (I), which comprises:

(1) a first step of reacting a compound represented by the formula (IX):

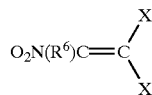

wherein X is a halogen atom, and $R^6$ is as defined above, and/or a compound represented by the formula (X): $O_2N—CH(R^6)CX_3$, wherein X and $R^6$ are as defined above, with a compound of the above formula (III) to obtain a compound represented by the formula (XI):

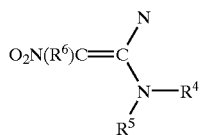

wherein X, $R^4$, $R^5$ and $R^6$ are as defined above, and (2) a second step of reacting a compound of the above formula (XI) obtained in the first step, with a compound of the above formula (V) to obtain a nitroetheneamine derivative of the above formula (I).

(4) Process 4

A process for producing a nitroetheneamine derivative of the above formula (I) which comprises:

(1) a first step of reacting a compound of the above formula (IX) and/or a compound of the above formula (X), with a compound of the above formula (V) to obtain a compound represented by the formula (XII):

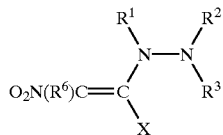

wherein X, $R^1$, $R^2$, $R^3$ and $R^6$ are as defined above, and (2) a second step of reacting the compound of the above formula (XII) obtained in the first step with a compound of the above formula (III) to obtain a nitroetheneamine derivative of the above formula (I).

Further, the compound of the above formula (IX) and the compound of the above formula (X) which are the starting materials in Process 3 and Process 4, can be produced by a known method disclosed, for example, in Journal of Organic Chemistry, Vol. 25, 1312 (1960) or a method similar thereto.

The respective reactions of Process 3 and Process 4 can be carried out in the presence of a suitable solvent. The solvent to be specifically used, may, for example, be an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In Process 3 and Process 4, in order to carry out the respective reactions efficiently, it is preferred to carry out the reaction in the presence of a base. The base to be specifically used, may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide. Further, the compound of the above formula (III) and/or the compound of the above formula (V) also acts as a base.

The respective reactions of Process 3 and Process 4 are carried out usually at a reaction temperature of from −30 to 150° C., preferably at a reaction temperature of from 0 to 80° C. The reaction time is usually from 0.1 to 48 hours.

In the first step of Process 3, the compound of the above formula (III) can be used in an amount of from 0.8 to 2 equivalents, preferably from 1 to 1.2 equivalents, per mol of the compound of the above formula (IX). Further, in the second step of Process 3, the compound of the above formula (III) can be used in an amount of from 1 to 1.5 equivalents per mol of the compound of the above formula (XI). However, it may be used excessively without any particular problem.

In the first step of Process 4, the compound of the above formula (V) can be used in an amount of from 1 to 2 equivalents, preferably from 1 to 1.2 equivalents, per mol of the compound of the above formula (IX). Further, in the second step of Process 4, the compound of the above formula (III) can be used in an amount of from 1 to 1.5 equivalents per mol of the compound of the above formula (XII). However, it may be used excessively without any particular problem.

The compound of the above formula (XI) obtained in Process 3, and the compound of the above formula (XII) obtained in Process 4, may be supplied to the subsequent reaction for producing the compound of the above formula (I) directly in the form of the reaction mixture or after separation and purification by a known means such as concentration, concentration under reduced pressure, solvent extraction, recrystallization or chromatography.

Various reaction conditions in Process 3 i.e. (1) the type of the compound of the above formula (IX) and/or the compound of the above formula (X), (2) the amount of the compound of the above formula (IX) and the compound of the above formula (X), (3) the type and/or the amount of the compound of the above formula (III), (4) with or without use of a solvent in the reaction of the first step, (5) the type and/or the amount of the solvent in the reaction in the first step, (6) with or without use of a base in the reaction of the first step, (7) the type and/or the amount of a base in the reaction of the first step, (8) the reaction temperature in the first step, (9) the reaction time in the first step, (10) the type of the compound of the above formula (XI) which is an intermediate product in the first step, (11) with or without separation and purification of the compound of the above formula (XI), (12) the type and/or the amount of the compound of the formula (V), (13) with or without use of a solvent in the reaction of the second step, (14) the type and/or the amount of the solvent in the reaction of the second step, (15) with or without use of a base in the reaction of the second step, (16) the type and/or the amount of the base in the reaction of the second step, (17) the reaction temperature in the reaction of the second step, (18) the reaction time in the reaction of the second step, and (19) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 3.

Various reaction conditions in Process 4 i.e. (1) the type of the compound of the above formula (IX) and/or the compound of the above formula (X), (2) the amount of the compound of the above formula (IX) and the compound of the above formula (X), (3) the type and/or the amount of the compound of the above formula (V), (4) with or without use of a solvent in the reaction of the first step, (5) the type and/or the amount of the solvent in the reaction of the first step, (6) with or without use of a base in the reaction of the first step, (7) the type and/or the amount of a base in the reaction of the first step, (8) the reaction temperature in the first step, (9) the reaction time in the first step, (10) the type of the compound of the above formula (XII) which is an intermediate product in the first step, (11) with or without separation and purification of the compound of the above formula (XII), (12) the type and/or the amount of the compound of the formula (III), (13) with or without use of a solvent in the reaction of the second step, (14) the type and/or the amount of the solvent in the reaction of the second step, (15) with or without use of a base in the reaction of the second step, (16) the type and/or the amount of the base in the reaction of the second step, (17) the reaction temperature in the reaction of the second step, (18) the reaction time in the reaction of the second step, and (19) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combination of the above various reaction conditions are also within the scope of Process 4.

(5) Process 5

A process for producing a nitroetheneamine derivative of the after-mentioned formula (I'), which comprises:

(1) a first step of reacting a compound represented by the above formula (V) with a compound represented by the formula (XIII): R⁴-NCS, wherein R⁴ is as defined above, to obtain a compound represented by the formula (XIV):

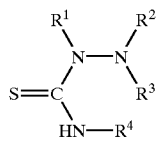

wherein $R^1$, $R^2$, $R^3$ and $R^4$ are as defined above, and (2) a second step of reacting the compound of the above formula (XIV) obtained in the first step with a compound of the formula (XV): Z-X wherein Z and X are as defined above, to obtain a compound of the formula (XVI):

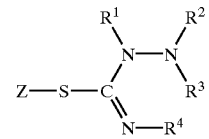

wherein Z, $R^1$, $R^2$, $R^3$ and $R^4$ are as defined above, and (3) a third step of reacting the compound of the above formula (XVI) obtained in the second step with a compound represented by the formula (XVII): $R^6$—$CH_2NO_2$, wherein $R^6$ is as defined above, to obtain a nitroetheneamine derivative of the formula (I'):

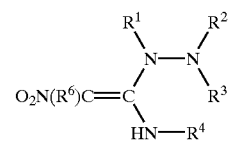

wherein $R^1$, $R^2$, $R^3$, $R^4$ and $R^6$ are as defined above.

Here, the compound of the above formula (I') is a compound of the above formula (I), and a compound where $R^5$ is a hydrogen atom.

The reaction in the first step of Process 5 can be carried out in the presence of a suitable solvent. The solvent to be specifically used, may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In the first step of Process 5, in order to carry out the reaction efficiently, it is preferred to carry out the reaction in the presence of a base. The base to be specifically used, may, for example, be an organic base such as triethylamine, pyridine, N-methylmorpholine, 1,8-diazabicyclo [5,4,0]-7-undecene or N,N-dimethylaniline; an alkali metal carbonate such as lithium carbonate, sodium carbonate or potassium carbonate; or an alkali metal hydrogencarbonate such as lithium hydrogencarbonate, sodium hydrogencarbonate or potassium hydrogencarbonate. Further, the compound of the above formula (V) also acts as a base.

The reaction in the first step of Process 5 is carried out usually at a reaction temperature of from −30 to 200° C., preferably at a reaction temperature of from 0 to 150° C. The reaction time is usually from 0.1 to 48 hours.

In the first step of Process 5, the compound of the above formula (XIII) is used in an amount of from 0.8 to 2 equivalents, preferably from 1 to 1.2 equivalents, per mol of the compound of the above formula (V). The obtained compound of the above formula (XIV) may be supplied to the reaction of the second step directly in the form of the reaction mixture or after separation and purification by a known means such as concentration, concentration under reduced pressure, solvent extraction, recrystallization or chromatography.

The reaction in the second step of Process 5 can be carried out in the presence of a suitable solvent. The solvent to be specifically used, may, for example, be an alcohol such as methanol, ethanol, propanol or butanol; a ketone such as acetone, methyl ethyl ketone, dimethyl ketone or diethyl ketone; an ester such as methyl acetate, ethyl acetate, butyl acetate, methyl formate, ethyl formate, butyl formate or ethyl propionate; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In the second step of Process 5, in order to carry out the reaction efficiently, it is preferred to carry out the reaction in the presence of a base. The base to be specifically used may, for example, be an organic base such as triethylamine, pyridine, N-methylmorpholine, 1,8-diazabicyclo [5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide.

The reaction in the second step of Process 5 is carried out usually at a temperature of from −30 to 150° C., preferably at a temperature of from 0 to 100° C. The reaction time is usually from 0.1 to 48 hours.

In the reaction of the second step in Process 5, the compound of the above formula (XV) can be used in an amount of at least 1 equivalent per mol of the compound of the above formula (XIV). As the compound of the above formula (XV), various compounds may be employed. For example, benzyl bromide or methyl iodide may be employed. The obtained compound of the above formula (XVI) may be supplied to the reaction of the third step directly in the form of the reaction mixture or after separation and purification by a known means such as concentration, concentration under reduced pressure, solvent extraction, recrystallization or chromatography.

The reaction of the third step in Process 5 can be carried out in the presence of a suitable solvent. The solvent to be specifically used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In the third step of Process 5, in order to carry out the reaction efficiently, it is preferred to carry out the reaction in the presence of a base. The base to be specifically used may, for example, be an organic base such as triethylamine, pyridine, N-methylmorpholine, 1,8-diazabicyclo [5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide.

The reaction in the third step of Process 5 can be carried out usually at a reaction temperature of from −30 to 200° C., preferably at a reaction temperature of from 0 to 150° C. The reaction time is usually from 0.1 to 48 hours.

In the reaction of the third step in Process 5, the compound of the above formula (XVII) can be used in an amount of from 1 to 5 equivalents per mol of the compound of the above formula (XVI).

Various reaction conditions in Process 5 i.e. (1) the type and/or the amount of the compound of the formula (V), (2) the type and/or the amount of the compound of the formula (XIII), (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature of the first step, (8) the reaction time of the first step, (9) the type of the compound of the above formula (XIV) which is an intermediate product in the first step, (10) with or without separation and purification of the compound of the formula (XIV) which is an intermediate product in the first step, (11) the type and/or the amount of the compound of the formula (XV), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature of the second step, (17) the reaction time of the second step, (18) the type of the compound of the above formula (XVI) which is an intermediate product in the second step, (19) with or without separation and purification of the compound of the formula (XVI) which is an intermediate product in the second step, (20) the type and/or the amount of the compound of the formula (XVII), (21) with or without use of a solvent in the reaction of the third step, (22) the type and/or the amount of the solvent in the reaction of the third step, (23) with or without use of a base in the reaction of the second step, (24) the type and/or the amount of a base in the reaction of the second step, (25) the reaction temperature of the third step, (26) the reaction time of the third step, and (27) the type of the compound of the formula (I') as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 5.

(6) Process 6

A process for producing a nitroetheneamine derivative of the above formula (I), which comprises:

(1) a first step of reacting a compound represented by the formula (XVIII):

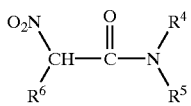

wherein $R^4$, $R^5$ and $R^6$ are as defined above, with a halogenating agent to obtain a compound of the above formula (XI), and (2) a second step of reacting the compound of the above formula (XI) obtained in the first step with a compound of the above formula (V) to obtain a compound of the above formula (I).

(7) Process 7

A process for producing a nitroetheneamine derivative of the above formula (I), which comprises:

(1) a first step of reacting a compound represented by the formula (XIX):

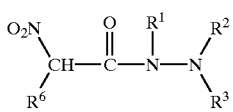

wherein $R^1$, $R^2$, $R^3$ and $R^6$ are as defined above, with a halogenating agent to obtain a compound of the above formula (XII), and (2) a second step of reacting the compound of the above formula (XII) obtained in the first step with a compound of the above formula (III) to obtain a compound of the above formula (I).

Here, the compound of the above formula (XVIII) and the compound of the above formula (XIX) which are the starting materials in Process 6 and Process 7, can be produced by a known method or a method similar thereto.

The reactions of the first step of Process 6 and the first step of Process 7, are preferably carried out in the presence of a solvent. The solvent to be specifically used may, for example, be an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a halogenated hydrocarbon such as chloroform, dichloromethane, carbon tetrachloride or 1,2-dichloroethane; and a solvent mixture thereof. The reaction is preferably carried out in a system where no water is present.

The halogenating agent to be used in the reactions of the first step of Process 6 and the first step of Process 7, may, for example, be phosphorus pentachloride, phosphorus oxychloride, phosphorus trichloride, thionyl chloride or oxalyl chloride. The amount is from 1 to 10 equivalents, preferably from 1 to 5 equivalents, per mol of the compound of the above formula (XVIII) or the compound of the above formula (XIX). Further, it is preferred to let a base be present to capture hydrogen chloride formed by this reaction. Such a base may, for example, be an organic base such as triethylamine, pyridine, N-methylmorpholine, 1,8-diazabicyclo[5,4,0]-7-undecene or N,N-dimethylaniline.

The reactions of the first step of Process 6 and the first step of Process 7 are carried out usually at a reaction temperature of from −30 to 200° C., preferably at a reaction temperature of from 0 to 150° C. The reaction time is usually from 0.1 to 48 hours.

The compound of the above formula (XI) obtained in the first step of Process 6 and the compound of the above formula (XII) obtained in the first step of Process 7, may be supplied to the reaction of the second step of Process 6 which is the same reaction as in the second step of Process 3 and to the reaction of the second step of Process 7 which is the same reaction as in the second step of Process 4, directly in the form of the reaction mixtures or after separation and purification by a known means such as concentration, concentration under reduced pressure, solvent extraction, recrystallization or chromatography.

Various reaction conditions in Process 6 i.e. (1) the type and/or the amount of the compound of the formula (XVIII), (2) the type and/or the amount of the halogenating agent, (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature of the first step, (8) the reaction time of the first step, (9) the type of the compound of the formula (XI) which is an intermediate product in the first step, (10) with or without separation and purification of the compound of the above formula (XI), (11) the type and/or the amount of the compound of the formula (V), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature in the reaction of the second step, (17) the reaction time in the reaction of the second step, and (18) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 6.

Various reaction conditions in Process 7 i.e. (1) the type and/or the amount of the compound of the formula (XIX), (2) the type and/or the amount of the halogenating agent, (3) with or without use of a solvent in the reaction of the first step, (4) the type and/or the amount of the solvent in the reaction of the first step, (5) with or without use of a base in the reaction of the first step, (6) the type and/or the amount of a base in the reaction of the first step, (7) the reaction temperature of the first step, (8) the reaction time of the first step, (9) the type of the compound of the formula (XII) which is an intermediate product in the first step, (10) with or without separation and purification of the compound of the above formula (XII), (11) the type and/or the amount of the compound of the formula (III), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature in the reaction of the second step, (17) the reaction time in the reaction of the second step, and (18) the type of the compound of the formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 7.

(8) Process 8

A process for producing a nitroetheneamine of the above formula (I), which comprises reacting a compound represented by the formula (XX):

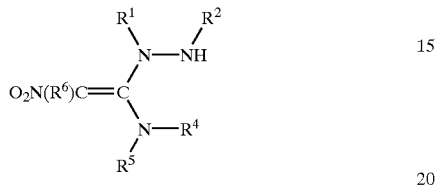

wherein $R^1$, $R^2$, $R^4$, $R^5$ and $R^6$ are as defined above, with a compound represented by the formula (XXI):
X—$R^3$, wherein $R^3$ and X are as defined above.

For the reaction of Process 8, it is preferred to carry out the reaction in the presence of a solvent. The solvent to be specifically used may, for example, be an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In Process 8, in order to carry out the reaction efficiently, it is preferred to carry out the reaction in the presence of a base. The base to be specifically used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; n-butyl lithium, lithium diisopropylamide or sodium amide.

The reaction of Process 8 is carried out usually at a reaction temperature of from −70 to 150° C., preferably at a reaction temperature of from −50 to 100° C. The reaction time is usually from 0.1 to 48 hours.

In Process 8, the compound of the formula (XXI) can be used in an amount of from 0.8 to 2 equivalents, preferably from 1 to 1.5 equivalents, per mol of the compound of the above formula (XX).

Various reaction conditions in Process 8 i.e. (1) the type and/or the amount of the compound of the formula (XX), (2) the type and/or the amount of the compound of the formula (XXI), (3) with or without use of a solvent, (4) the type and/or the amount of the solvent, (5) with or without use of a base, (6) the type and/or the amount of the base, (7) the reaction temperature, (8) the reaction time and (9) the type of the compound of the above formula (I) as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also in the scope of Process 8.

A compound of the formula (I"):

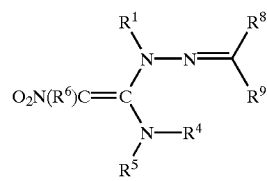

wherein $R^1$, $R^4$, $R^5$, $R^6$, $R^8$ and $R^9$ are as defined above, is a compound of the above formula (I) and a compound wherein $R^2$ and $R^3$ form together with the N atom a N=$CR^8R^9$ group, wherein $R^8$ and $R^9$ are as defined above. This compound can be produced by a method as shown by the following Process 9.

(9) Process 9

A process for producing a nitroetheneamine of the above formula (I"), which comprises reacting a compound represented by the formula (XXII):

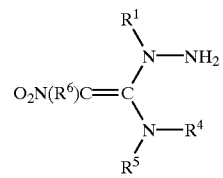

wherein $R^1$, $R^4$, $R^5$ and $R^6$ are as defined above, with a compound represented by the formula (XXIII):

wherein $R^8$ and $R^9$ are as defined above.

For the reaction of Process 9, it is preferred to carry out the reaction in the presence of a solvent. The solvent to be specifically used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane, and a solvent mixture thereof.

In Process 9, in order to carry out the reaction efficiently, it is preferred to carry out the reaction in the presence of a base. The base to be specifically used may, for example, be an organic base such as triethylamine, pyridine, N-methylmorpholine, 1,8-diazabicyclo[5,4,0]-7-undecene or N,N-dimethylaniline; an alkali metal carbonate such as lithium carbonate, sodium carbonate or potassium carbonate; or an alkali metal hydrogencarbonate such as lithium hydrogencarbonate, sodium hydrogencarbonate or potassium hydrogencarbonate.

In Process 9, in order to carry out the reaction efficiently, it is preferred to carry out the reaction in the presence of a dehydrating agent such as molecular sieves. Further, it is also possible to remove formed moisture out of the reaction system by azeotropy using a suitable solvent.

The reaction of Process 9 is carried out usually at a reaction temperature of from −30 to 150° C., preferably at a reaction temperature of from 0 to 100° C. The reaction time is usually from 0.1 to 48 hours.

In the reaction of Process 9, the compound of the above formula (XXIII) can be used in an amount of from 0.8 to 2 equivalents, preferably from 1 to 1.5 equivalents, per mol of the compound of the above formula (XXII).

Various reaction conditions in Process 9 i.e. (1) the type and/or the amount of the compound of the formula (XXII), (2) the type and/or the amount of the compound of the formula (XXIII), (3) with or without use of a solvent, (4) the type and/or the amount of the solvent, (5) with or without use of a base, (6) the type and/or the amount of the base, (7) with or without use of a dehydrating agent, (8) the type and/or the amount of the dehydrating agent, (9) the reaction temperature, (10) the reaction time, and (11) the type of the compound of the formula (I'') as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also in the scope of Process 9.

(10) Process 10

A process for producing a nitroetheneamine derivative of the above formula (I'), which comprises:

(1) a first step of reacting a compound represented by the formula (XXIV):

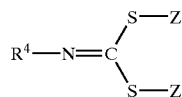

wherein $R^4$ and Z are as defined above, with a compound of the above formula (XVII) to obtain a compound represented by the formula (XXV):

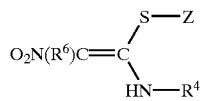

wherein $R^4$, $R^6$ and Z are as defined above, and (2) a second step of reacting the compound of the above formula (XXV) obtained in the first step with a compound of the above formula (V) to obtain a nitroetheneamine derivative of the above formula (I').

(11) Process 11

A process for producing a nitroetheneamine derivative of the after-mentioned formula (I'''), which comprises:

(1) a first step of reacting a compound represented by the formula (XXVI):

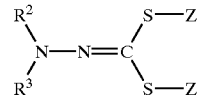

wherein $R^2$, $R^3$ and Z are as defined above, with a compound of the above formula (XVII) to obtain a compound of the formula (XXVII):

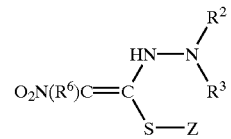

wherein $R^2$, $R^3$, $R^6$ and Z are as defined above, and (2) a second step of reacting the compound of the above formula (XVII) obtained in the first step with a compound of the above formula (III) to obtain a nitroetheneamine derivative represented by the formula (I'''):

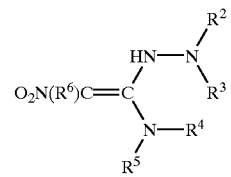

wherein $R^2$, $R_3$, $R^4$, $R^5$ and $R^6$ are as defined above. Here, the compound of the above formula (I''') is a compound of the above formula (I) and a compound wherein $R^1$ is a hydrogen atom. Further, the compound of the above formula (XXIV) and the compound of the above formula (XXVI) which are the starting materials in Process 10 and Process 11, can be produced by a known method or a method similar thereto.

The reaction in each step of Process 10 and Process 11 can be carried out in the presence of a suitable solvent. The solvent to be specifically used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In Process 10 and Process 11, in order to carry out the reaction of each step efficiently, it is preferred to carry out the reaction in the presence of a base. The base to be specifically used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide. Further, in the second step of Process 10, the compound of the above formula (V) acts also as a base. Further, in the second step of Process 11, the compound of the above formula (III) acts also as a base.

Each reaction of the first step in Process 10 and the first step in Process 11 is carried out usually at a reaction temperature of from −30 to 150° C., preferably at a reaction temperature of from 0 to 80° C. The reaction time is usually from 0.1 to 48 hours. In the first step of Process 10, the compound of the above formula (XVII) can be used in an amount of from 0.8 to 2 equivalents, preferably from 1 to 1.5 equivalents, per mol of the compound of the above formula (XXIV). Further, in the first step of Process 11, the compound of the above formula (XVII) can be used in an amount of from 0.8 to 2 equivalents, preferably from 1 to 1.5 equivalents, per mol of the compound of the above formula (XXVI).

Each reaction of the second step in Process 10 and the second step in Process 11, is carried out usually at a temperature of from −30 to 150° C., preferably at a reaction temperature of from 0 to 80° C. The reaction time is usually from 0.1 to 48 hours. In the second step of Process 10, the compound of the above formula (V) can be used in an amount of from 1 to 1.5 equivalents, per mol of the compound of the above formula (XXV). Further, in the second step of Process 11, the compound of the above formula (III) can be used in an amount of from 1 to 1.5 equivalents per mol of the compound of the above formula (XXVII).

The compound of the above formula (XXV) obtained in the first step of Process 10 and the compound of the above formula (XXVII) obtained in the first step of Process 11 may be supplied to the respective reactions in the second step of Process 10 and in the second step of Process 11 directly in the form of the reaction mixtures or after separation and purification by a known means such as concentration, concentration under reduced pressure, solvent extraction, recrystallization or chromatography.

Various reaction conditions in Process 10 i.e. (1) the type and/or the amount of the compound of the formula (XXIV), (2) the type and/or the amount of the compound of the formula (XVII), (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature of the first step, (8) the reaction time of the first step, (9) the type of the compound of the formula (XXV) which is an intermediate product in the first step, (10) with or without separation and purification of the compound of the above formula (XXV), (11) the type and/or the amount of the compound of the formula (V), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature in the reaction of the second step, (17) the reaction time in the reaction of the second step, and (18) the type of the compound of the formula (I') as the final desired product, may mutually suitably be combined.

Further, among these various reaction conditions, there are some which have a reaction condition of a usual range and a reaction condition of a preferred range, and they may also mutually suitably be selected and combined.

Combinations of the above various reaction conditions are also within the scope of Process 10.

Various reaction conditions in Process 11 i.e. (1) the type and/or the amount of the compound of the formula (XXVI), (2) the type and/or the amount of the compound of the formula (XVII), (3) with or without use of a solvent in the reaction of the first step, (4) the type and/or the amount of the solvent in the reaction of the first step, (5) with or without use of a base in the reaction of the first step, (6) the type and/or the amount of the base in the reaction of the first step, (7) the reaction temperature of the first step, (8) the reaction time of the first step, (9) the type of the compound of the formula (XXVII) which is an intermediate product in the first step, (10) with or without separation and purification of the compound of the above formula (XXVII), (11) the type and/or the amount of the compound of the formula (III), (12) with or without use of a solvent in the reaction of the second step, (13) the type and/or the amount of the solvent in the reaction of the second step, (14) with or without use of a base in the reaction of the second step, (15) the type and/or the amount of the base in the reaction of the second step, (16) the reaction temperature in the reaction of the second step, (17) the reaction time in the reaction of the second step, and (18) the type of the compound of the formula (I''') as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 11.

(12) Process 12

A process for producing a nitroetheneamine derivative of the above formula (I'), which comprises:

(1) a first step of reacting a compound represented by the above formula (XIII) with a compound of the above formula (XVII) and then reacting a compound of the above formula (XV) to obtain a compound represented by the formula (XXV):

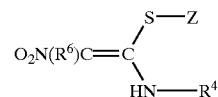

wherein $R^4$, $R^6$ and Z are as defined above, and (2) a second step of reacting the compound of the above formula (XXV) obtained in the first step with a compound of the above formula (V) to obtain a nitroetheneamine derivative of the above formula (I').

Each reaction in Process 12 can be carried out in the presence of a suitable solvent. The solvent to be specifically used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzin; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphoric acid amide such as hexamethylphosphoramide; a halogenated hydrocarbon such as chloroform, dichloromethane, carbon tetrachloride or 1,2-dichloroethane; and a solvent mixture thereof.

In Process 12, in order to carry out each reaction efficiently, it is preferred to carry out the reaction in the presence of a base. The base to be specifically used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or an alkoxide such as sodium methoxide, sodium ethoxide or potassium t-butoxide. Further, in the second step of Process 12, the compound of the above formula (V) acts also as a base.

The reaction in the first step of Process 12 is carried out usually at a reaction temperature of from −30 to 150° C., preferably at a reaction temperature of from 0 to 80° C. The reaction time is usually from 0.1 to 48 hours.

In the first step of Process 12, the compounds of the above formula (XVII) and the formula (XV) can be used in an amount of from 0.8 to 2 equivalents, preferably from 1 to 1.5 equivalents, per mol of the compound of the above formula (XIII), respectively.

The compound of the above formula (XXV) obtained in the first step of Process 12 may be supplied to the reaction of the second step of Process 12 directly in the form of the reaction mixture or after separation and purification by a known means such as concentration, concentration under reduced pressure, solvent extraction, recrystallization or chromatography.

The reaction of the second step of Process 12 is carried out usually at a reaction temperature of from −30 to 150° C., preferably at a reaction temperature of from 0 to 80° C. The reaction time is usually from 0.1 to 48 hours.

In the second step of Process 12, the compound of the above formula (V) can be used in an amount of from 1 to 1.5 equivalents per mol of the compound of the above formula (XXV).

Various reaction conditions in Process 12 i.e. (1) the type and/or the amount of the compound of the formula (XIII), (2) the type and/or the amount of the compound of the formula (XVII), (3) the type and/or the amount of the compound of the formula (XV), (4) with or without use of a solvent in the reaction of the first step, (5) the type and/or the amount of the solvent in the reaction of the first step, (6) with a without use of a base in the reaction of the first step, (7) the type and/or the amount of the base in the reaction of the first step, (8) the reaction temperature of the first step, (9) the reaction time of the first step, (10) the type of the compound of the formula (XXV) which is an intermediate product in the first step, (11) with or without separation and purification of the compound of the above formula (XXV), (12) the type and/or the amount of the compound of the formula (V), (13) with or without use of a solvent in the reaction of the second step, (14) the type and/or the amount of the solvent in the reaction of the second step, (15) with or without use of a base in the reaction of the second step, (16) the type and/or the amount of the base in the reaction of the second step, (17) the reaction temperature in the reaction of the second step, (18) the reaction time in the reaction of the second step, and (19) the type of the compound of the formula (I') as the final desired product, may mutually suitably be combined. Further, among these various reaction conditions, there are some which have a reaction condition of a usual range and a reaction condition of a preferred range, and they may also mutually suitably be selected and combined.

Combinations of the above various reaction conditions are also within the scope of Process 12.

The compounds of the above formula (I) (inclusive of compounds of the formula (I'), the formula (I") and the formula (I'")) obtained by the processes as described in the foregoing Processes 1 to 12, can be isolated and purified by a known means such as concentration, concentration under reduced pressure, distillation, fractionation, redistribution, solvent extraction, crystallization, recrystallization or chromatography.

When the compound of the above formula (I) is obtained in a free form, it may be formed into a salt by a usual method. Further, the compound of the above formula (I) may form an intramolecular salt. The compounds of the above formula (I), and their stereoisomers or tautomer exhibit matrix metalloproteinase inhibition activities individually or in a state of a mixture. The production flowcharts of the above-described Processes 1 to 12 will be shown below.

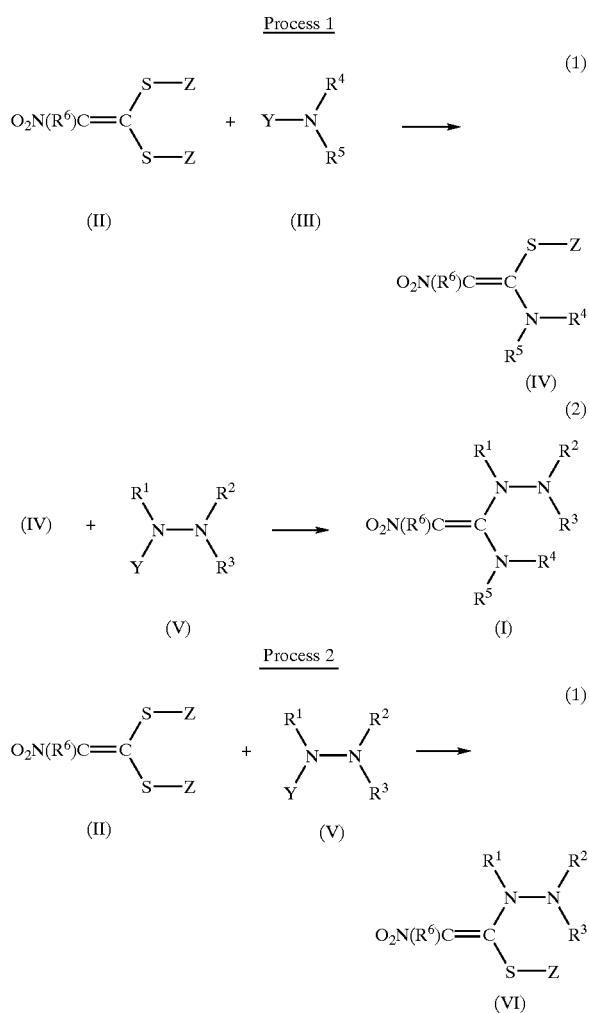

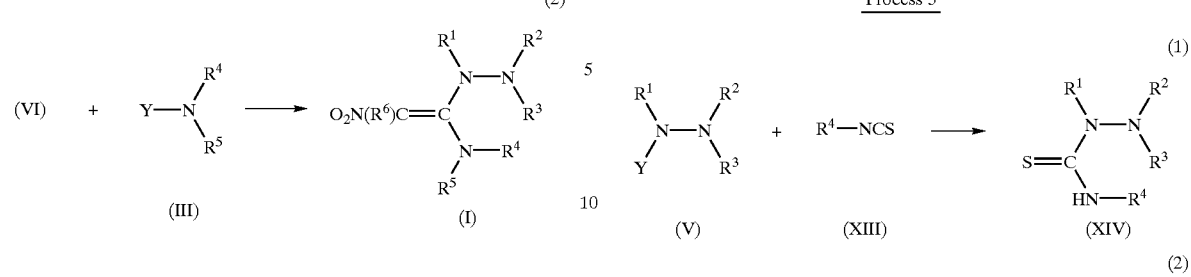
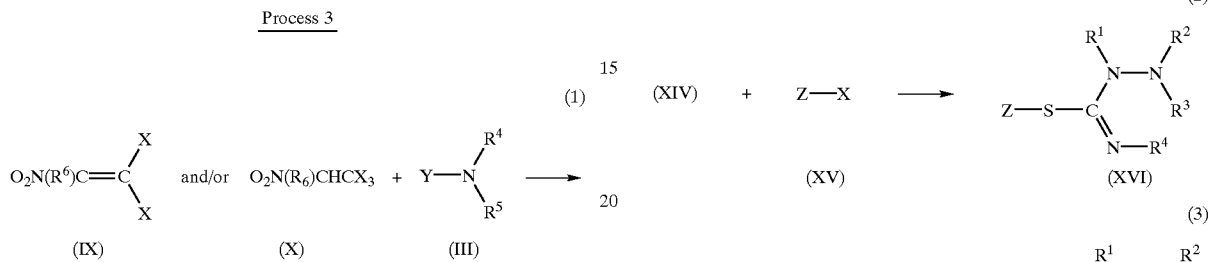
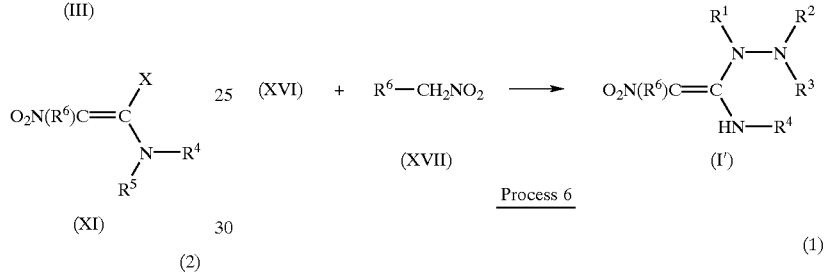
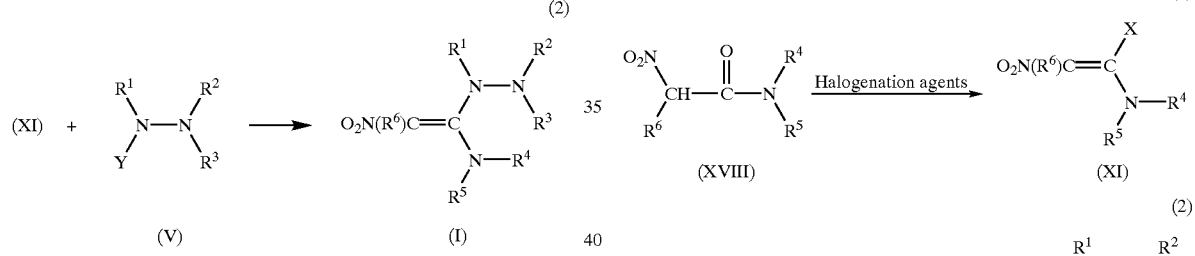
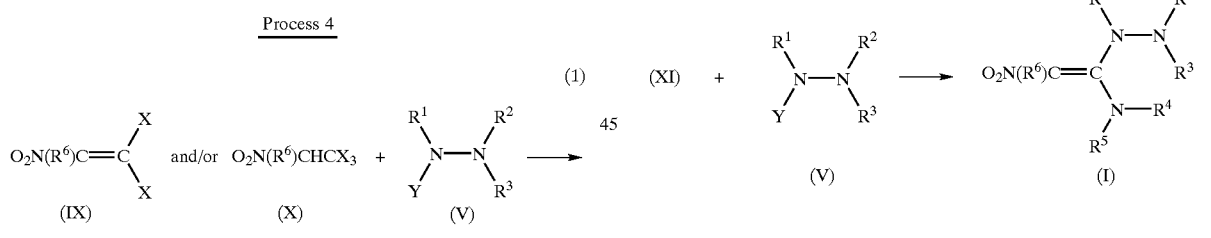
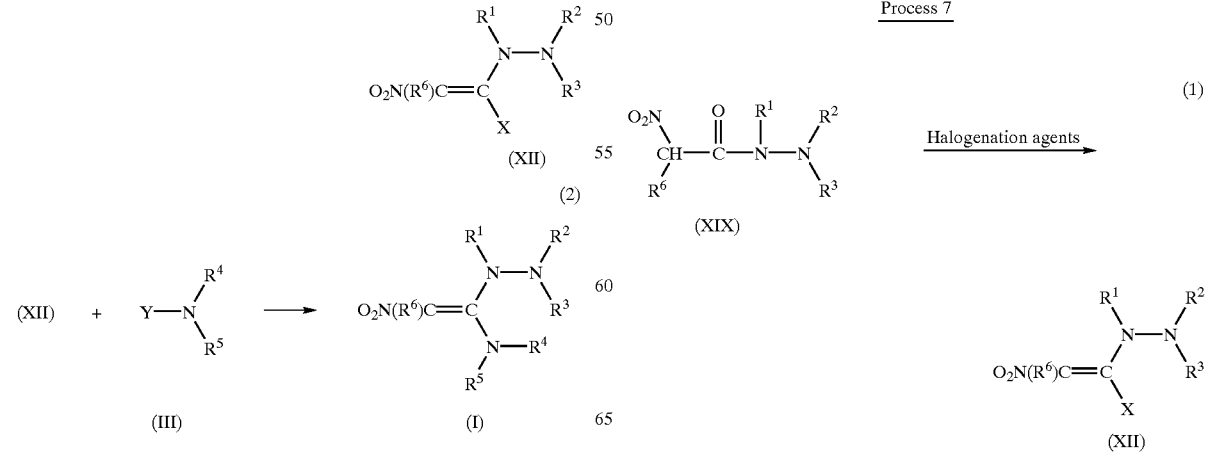

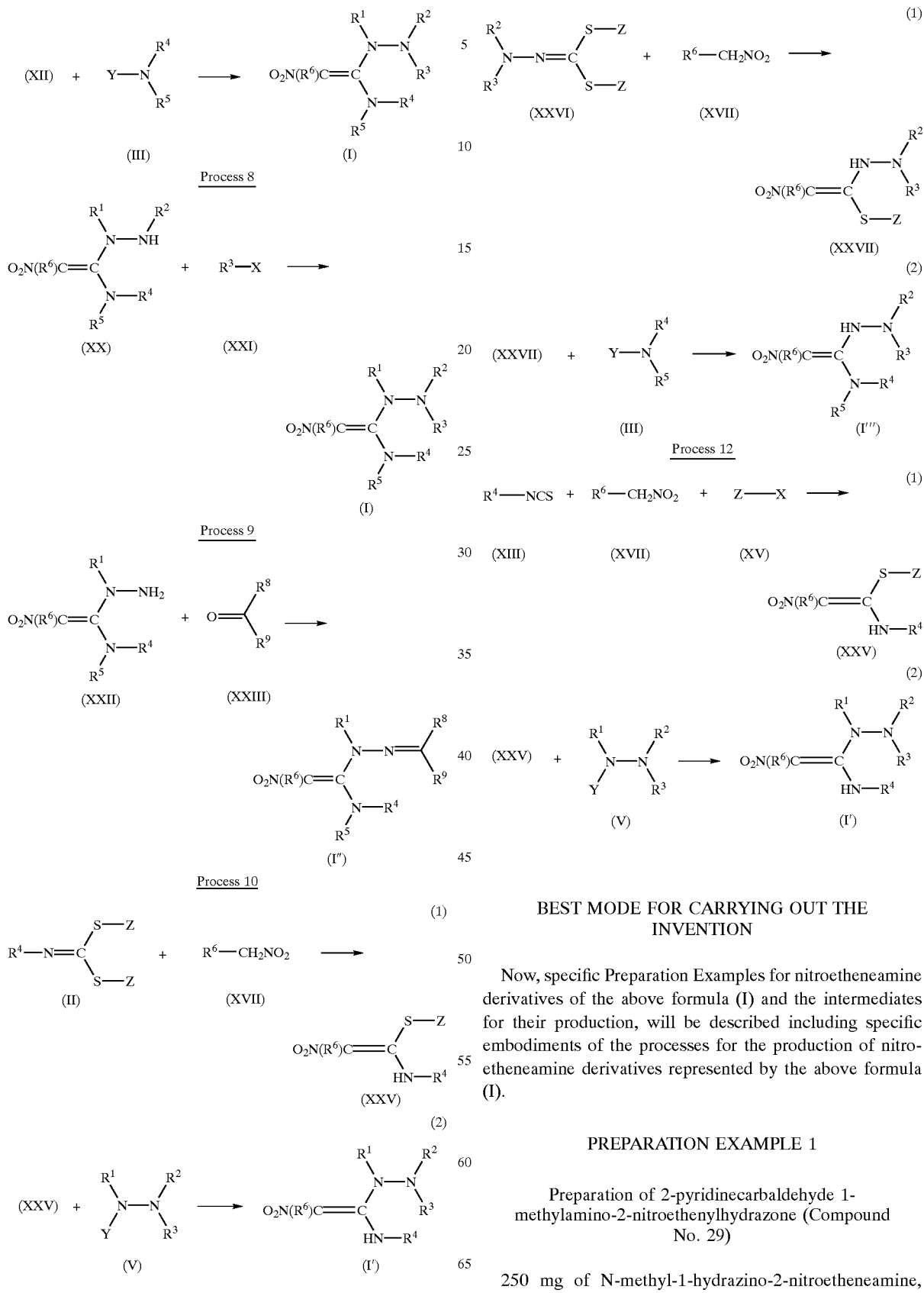

BEST MODE FOR CARRYING OUT THE INVENTION

Now, specific Preparation Examples for nitroetheneamine derivatives of the above formula (I) and the intermediates for their production, will be described including specific embodiments of the processes for the production of nitroetheneamine derivatives represented by the above formula (I).

PREPARATION EXAMPLE 1

Preparation of 2-pyridinecarbaldehyde 1-methylamino-2-nitroethenylhydrazone (Compound No. 29)

250 mg of N-methyl-1-hydrazino-2-nitroetheneamine, 210 mg of 2-pyridinecarbaldehyde and 5 ml of ethanol were stirred for about 30 minutes under heating and refluxing and then cooled to room temperature, whereupon precipitated crystals were collected by filtration. The crystals obtained by filtration were washed with a small amount of ethanol and then dried to obtain 300 mg of 2-pyridinecarbaldehyde 1-methylamino-2-nitroethenylhydrazone (Compound No. 29) having a melting of 165° C. (decomposed).

PREPARATION EXAMPLE 2

Preparation of N-methyl-1-(2-methyl-2-(3-chloro-5-trifluoromethyl-2-pyridyl)hydrazino)-2-nitroetheneamine (Compound No. 35)

500 mg of N-methyl-1-methylthio-2-nitroetheneamine, 770 mg of 1-methyl-1-(3-chloro-5-trifluoromethyl-2-pyridyl)hydrazine and 7 ml of 1,4-dioxane were stirred for about 4 hours under heating and refluxing and then cooled to room temperature, and the solvent was distilled off under reduced pressure. The concentrated residue was purified by silica gel column chromatography to obtain 370 mg of N-methyl-1-(2-methyl-2-(3-chloro-5-trifluoromethyl-2-pyridyl)hydrazino)-2-nitroetheneamine (Compound No. 35) having a melting point of from 159 to 160° C. (decomposed).

PREPARATION EXAMPLE 3

Preparation of N-methyl-1-(2-(4-trifluoromethyl-6-methoxy-2-pyridyl)hydrazino)-2-nitroetheneamine (Compound No. 98)

(1) 9 g of a 28% sodium methylate methanol solution was dissolved in 30 ml of methanol, and a solution obtained by dissolving 10 g of 2,6-dichloro-4-trifluoromethylpyridine in 15 ml of methanol, was dropwise added thereto, followed by stirring for about 90 minutes under heating and refluxing. After completion of the reaction, the solution was cooled to room temperature, and about 40 ml of an ether was added, whereupon an insoluble substance was removed by filtration, and then the filtrate was concentrated under reduced pressure. To the concentrated residue, 15 ml of n-propanol and 6 g of hydrazine monohydrate were added, followed by stirring for about 19 hours under heating and refluxing. After completion of the reaction, the solution was cooled to room temperature, and the solvent was distilled off under reduced pressure. The concentrated residue was extracted with chloroform and dried over anhydrous sodium sulfate, whereupon the solvent was distilled off under reduced pressure to obtain 6.6 g of crude 4-trifluoromethyl-6-methoxy-2-pyridylhydrazine (Intermediate No. 71).

(2) 4.7 g of N-methyl-1-methylthio-2-nitroetheneamine, 6.6 g of crude 4-trifluoromethyl-6-methoxy-2-pyridylhydrazine (Intermediate No. 71) and 35 ml of ethanol were stirred for about 5.5 hours under heating and refluxing and then cooled to room temperature, whereupon precipitated crystals were collected by filtration. The crystals obtained by filtration were washed with a small amount of methanol and then dried to obtain 2.7 g of N-methyl-1-(2-(4-trifluoromethyl-6-methoxy-2-pyridyl)hydrazino)-2-nitroetheneamine (Compound No. 98) having a melting point of 193° C. (decomposed).

PREPARATION EXAMPLE 4

Preparation of N-(1-hydrazino-2-nitroethenyl)-4-trifluoromethoxyaniline (Compound No. 61)

(1) 3.00 g of 1,1-bis(methylthio)-2-nitroethene, 3.38 g of 4-trifluoromethoxyaniline and 30 ml of ethanol were reacted for 5 hours under heating and refluxing and then cooled to room temperature, whereupon precipitated crystals were collected by filtration and washed with a small amount of ethanol and dried to obtain 3.40 g of crystals, to which 1.81 g of 4-trifluoromethoxyaniline and 30 ml of ethanol were added and reacted for 6.5 hours under heating and refluxing. After completion of the reaction, the solution was cooled to room temperature, and precipitated crystals were collected by filtration, washed with a small amount of ethanol and dried to obtain 2.51 g of N-(1-methylthio-2-nitroethenyl)-4-trifluoromethoxyaniline (Intermediate No. 30) having a melting point of from 114 to 115° C.

(2) To 2.00 g of N-(1-methylthio-2-nitroethenyl)-4-trifluoromethoxyaniline (Intermediate No. 30) obtained in the above step (1), 40 ml of ethanol was added at room temperature, and then 0.36 g of hydrazine monohydrate was dropwise added thereto. Thereafter, the reaction was carried out for 1 hour under heating and refluxing. After completion of the reaction, the solution was cooled to room temperature, and precipitated crystals were collected by filtration, washed with a small amount of ethanol and dried to obtain 1.36 g of the desired product (Compound No. 61) having a melting point of 161° C. (decomposition point).

PREPARATION EXAMPLE 5

Preparation of N-(1-(6-chloro-4-trifluoromethyl-2-pyridyl)hydrazino-2-nitroethenyl)methanesulfonamide (Compound No. 157)

(1) In 20 ml of dimethylsulfoxide, 2.00 g of N-((bismethylthio)methylene)methanesulfonamide, 0.92 g of nitromethane and 2.27 g of potassium carbonate were added and reacted for 6 hours at room temperature. The reaction mixture was poured into 75 ml of ice water and then acidified (pH=3) with 6N hydrochloric acid, whereupon precipitated crystals were collected by filtration, washed with a small amount of water and dried to obtain 0.49 g of N-(1-(methylthio)-2-nitroethenyl)methanesulfonamide (Intermediate No. 57) having a melting point of from 81 to 82° C.

(2) 0.40 g of N-(1-(methylthio)-2-nitroethenyl)methanesulfonamide (Intermediate No. 57) obtained in the above step (1), 0.40 g of 6-chloro-4-trifluoromethyl-2-pyridylhydrazine and 10 ml of ethanol were stirred for 1.5 hours under heating and refluxing and then cooled to room temperature, whereupon precipitated crystals were collected by filtration. The crystals obtained by filtration were washed with a small amount of ethanol and then dried to obtain 0.37 g of N-(1-(6-chloro-4-trifluoromethyl-2-pyridyl)hydrazino-2-nitroethenyl)methanesulfonamide (Compound No. 157) having a melting point of 190° C. (decomposed).

PREPARATION EXAMPLE 6

Preparation of N-(1-(6-(2-ethoxyethoxy)-4-trifluoromethyl-2-pyridyl)hydrazino-2-nitroethenyl)methanesulfonamide (Compound No. 164)

1.40 g of N-(1-(methylthio)-2-nitroethenyl)methanesulfonamide (Intermediate No. 57), 1.80 g of 6-(2-ethoxyethoxy)-4-trifluoromethyl-2-pyridylhydrazine and 11 ml of ethanol were stirred for 15 hours under heating and refluxing and then cooled to room temperature, whereupon precipitated crystals were collected by filtration. The crystals obtained by filtration were washed with a small amount of ethanol and then dried to obtain 0.97 g of N-(1-(6-(2-ethoxyethoxy)-4-trifluoromethyl-2-pyridyl)hydrazino-2-nitroethenyl)methanesulfonamide (Compound No. 164) having a melting point of 153° C.

PREPARATION EXAMPLE 7

Preparation of N-(1-(N-morpholino)amino-2-nitroethenyl)methanesulfonamide (Compound No. 163)

(1) 0.32 ml of nitromethane, 0.24 g of sodium hydride and 20 ml of N,N-dimethylformamide were stirred for 1 hour in a nitrogen atmosphere, and then 1.57 g of N-((bismethylthio)methylene)benzenesulfonamide was added thereto and reacted for 22 hours at room temperature. The reaction mixture was poured into 200 ml of ice water, and n-hexane was added and stirred for 30 minutes, followed by liquid separation to remove an organic layer. The aqueous layer was acidified (pH=3) with 6N hydrochloric acid, and then the oil content was extracted with an ether. The obtained extract solution was washed with water and with a saturated sodium chloride aqueous solution and dried over anhydrous magnesium sulfate. The solvent was distilled off under reduced pressure to obtain 1.27 g of oily N-(1-(methylthio)-2-nitroethenyl)benzenesulfonamide (Intermediate No. 56).

(2) 0.27 g of N-(1-(methylthio)-2-nitroethenyl)benzenesulfonamide (Intermediate No. 56) obtained in the above step (1), 0.10 g of N-aminomorpholine and 4 ml of ethanol were stirred for 24 hours under heating and refluxing and then cooled to room temperature, whereupon precipitated crystals were collected by filtration. The crystals obtained by filtration were washed with a small amount of ethanol/n-hexane mixed liquid (1/1) and then dried to obtain 0.22 g of N-(1-(N-morpholino)amino-2-nitroethenyl)methanesulfonamide (Compound No. 163) having a melting point of from 127 to 130° C.

Preparation Examples of compounds of the above formula (I) prepared by the methods of Preparation Examples 1 to 7 and in accordance with the above-described Processes 1 to 12, are shown in the following Tables 1 to 23.

TABLE 1

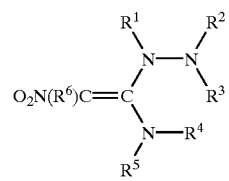

(I)

| Comp. No. | $R^1$ | $R^2$ | $R^3$ | $R^4$ | $R^5$ | $R^6$ | Physical property |
|---|---|---|---|---|---|---|---|
| 1 | H | —CH$_2$Ph | H | CH$_3$ | H | H | mp 151° C. (decomposed) |
| 2 | H | —Ph | H | —Ph | H | H | mp 155° C. (decomposed) |
| 3 | H | —COPh | H | CH$_3$ | H | H | mp 163° C. (decomposed) |
| 4 | H | —COCH$_3$ | H | CH$_3$ | H | H | mp 164° C. (decomposed) |
| 5 | H | —COOPh | H | CH$_3$ | H | H | mp 159° C. (decomposed) |
| 6 | H | —COOCH$_3$ | H | CH$_3$ | H | H | mp 147° C. (decomposed) |
| 7 | H | Bu(t) | H | CH$_3$ | H | H | mp 178° C. (decomposed) |
| 8 | H | 2-Cl-C$_6$H$_4$ | H | CH$_3$ | H | H | mp 178° C. (decomposed) |
| 9 | H | 3-Cl-C$_6$H$_4$ | H | CH$_3$ | H | H | mp 191° C. (decomposed) |
| 10 | H | 4-Cl-C$_6$H$_4$ | H | CH$_3$ | H | H | mp 187° C. (decomposed) |
| 11 | H | 2-NO$_2$-C$_6$H$_4$ | H | CH$_3$ | H | H | mp 194° C. (decomposed) |

TABLE 2

$$\text{O}_2\text{N}(R^6)\text{C}=\text{C}\begin{array}{c}R^1\\|\\N\\|\\N\\|\\R^5\end{array}\begin{array}{c}R^2\\|\\N-R^3\\\\N-R^4\end{array} \quad (I)$$

| Comp. No. | R¹ | R² | R³ | R⁴ | R⁵ | R⁶ | Physical property |
|---|---|---|---|---|---|---|---|
| 12 | H | 3-nitrophenyl | H | CH₃ | H | H | mp 176° C. (decomposed) |
| 13 | H | 4-nitrophenyl | H | CH₃ | H | H | mp 186° C. (decomposed) |
| 14 | H | 2-methylphenyl | H | CH₃ | H | H | mp 171° C. (decomposed) |
| 15 | H | 3-methylphenyl | H | CH₃ | H | H | mp 189° C. (decomposed) |
| 16 | H | 4-methylphenyl | H | CH₃ | H | H | mp 186° C. (decomposed) |
| 17 | H | 4-methoxyphenyl | H | CH₃ | H | H | mp 168° C. (decomposed) |
| 18 | H | =CH—phenyl | | CH₃ | H | H | mp 169–107° C. |
| 19 | H | 5-(trifluoromethyl)pyridin-2-yl | H | CH₃ | H | H | mp 207° C. (decomposed) |
| 20 | H | =CH—Bu(t) | | CH₃ | H | H | mp 134° C. |
| 21 | H | 3-chloro-5-(trifluoromethyl)pyridin-2-yl | H | CH₃ | H | H | mp 168° C. (decomposed) |
| 22 | H | pyridin-2-yl | H | CH₃ | H | H | mp 156° C. (decomposed) |

TABLE 3

$$\text{O}_2\text{N}(\text{R}^6)\text{C}=\text{C}\begin{array}{c}\text{R}^1\;\;\;\text{R}^2\\ |\;\;\;\;\;\;\;|\\ \text{N}-\text{N}\\ \;\;\;\;\;\;\;|\;\;\text{R}^3\\ \text{N}-\text{R}^4\\ |\\ \text{R}^5\end{array} \quad (I)$$

| Comp. No. | R¹ | R² | R³ | R⁴ | R⁵ | R⁶ | Physical property |
|---|---|---|---|---|---|---|---|
| 23 | H | −CH(CF₃)OH | H | CH₃ | H | H | mp 144–145° C. |
| 24 | H | =CH−(4-pyridyl) | | CH₃ | H | H | mp 224° C. (decomposed) |
| 25 | H | =C(CH₃)₂ | | CH₃ | H | H | mp 136° C. |
| 26 | H | =C(CH₃)(OCH₃) | | CH₃ | H | H | mp 159° C. (decomposed) |
| 27 | H | −(4-CF₃-2,6-dimethylpyridyl) | H | CH₃ | H | H | mp 161–162° C. |
| 28 | H | =CH−(3-pyridyl) | | CH₃ | H | H | mp 196° C. (decomposed) |
| 29 | H | =CH−(2-pyridyl) | | CH₃ | H | H | mp 165° C. (decomposed) |
| 30 | H | H | 4-NO₂-1,3,5-trimethylpyrazol-4-yl | CH₃ | H | H | mp 164° C. (decomposed) |
| 31 | H | =C(CH₃)−(3-thienyl) | | CH₃ | H | H | mp 202° C. (decomposed) |

TABLE 4

$$\text{O}_2\text{N}(\text{R}^6)\text{C}=\text{C}\begin{array}{c}\text{R}^1\;\;\;\text{R}^2\\ |\;\;\;\;\;\;\;|\\ \text{N}-\text{N}\\ \;\;\;\;\;\;\;|\;\;\text{R}^3\\ \text{N}-\text{R}^4\\ |\\ \text{R}^5\end{array} \quad (I)$$

| Comp. No. | R¹ | R² | R³ | R⁴ | R⁵ | R⁶ | Physical property |
|---|---|---|---|---|---|---|---|
| 32 | H | =C(CH₃)−(2-thienyl) | | CH₃ | H | H | mp 165° C. (decomposed) |

TABLE 4-continued
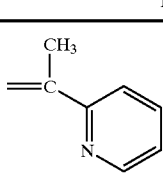
(I)
| Comp. No. | R¹ | R² | R³ | R⁴ | R⁵ | R⁶ | Physical property |
|---|---|---|---|---|---|---|---|
| 33 | H | 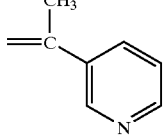 | | CH₃ | H | H | mp 170° C. (decomposed) |
| 34 | H | 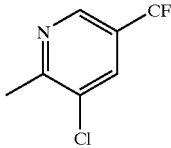 | | CH₃ | H | H | mp 181° C. (decomposed) |
| 35 | H | 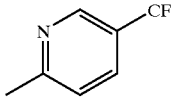 | CH₃ | CH₃ | H | H | mp 159–160° C. |
| 36 | H | 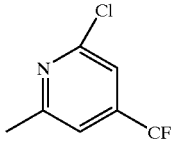 | CH₃ | CH₃ | H | H | mp 153–154° C. |
| 37 | H | 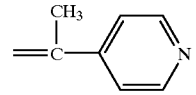 | H | CH₃ | H | H | mp 215–217° C. (decomposed) |
| 38 | H | 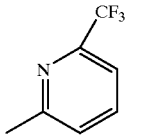 | | CH₃ | H | H | mp 199° C. (decomposed) |
| 39 | H | 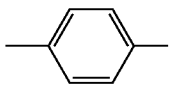 | CH₃ | CH₃ | H | H | mp 191–192° C. (decomposed) |
| 40 | H |  | H | CH₃ | H | H | mp 190° C. |

TABLE 5

$$\text{O}_2\text{N}(\text{R}^6)\text{C}=\text{C}\begin{array}{c}\text{R}^1\quad\text{R}^2\\ \diagdown\text{N}-\text{N}\diagup\\ \phantom{xx}\diagdown\text{R}^3\\ \text{N}-\text{R}^4\\ |\\ \text{R}^5\end{array} \quad (I)$$

| Comp. No. | R¹ | R² | R³ | R⁴ | R⁵ | R⁶ | Physical property |
|---|---|---|---|---|---|---|---|
| 41 | H | 6-methyl-5-(CF₃)-pyridin-2-yl | H | 4-methoxyphenyl | H | H | mp 155–157° C. |
| 42 | H | 3-methyl-(COOH-substituted)phenyl | H | CH₃ | H | H | mp 250° C.< |
| 43 | H | 3-Cl-2-methyl-5-(CF₃)-pyridin-6-yl | H | 4-methoxyphenyl | H | H | mp 130–135° C. |
| 44 | H | 2-methyl-4,6-bis(CF₃)-pyridin-yl | H | CH₃ | H | H | mp 192–193° C. (decomposed) |
| 45 | H | pyrimidin-2-yl (2-methyl) | H | CH₃ | H | H | mp 182–183° C. (decomposed) |
| 46 | H | H | H | CH₃(CH₂)₇— | H | H | mp 106–108° C. |
| 47 | H | H | H | CH₃(CH₂)₉— | H | H | mp 109–110° C. |
| 48 | H | H | H | 4-methylphenyl | H | H | mp 191° C. (decomposed) |
| 49 | H | H | H | 4-methoxyphenyl | H | H | mp 195° C. (decomposed) |

TABLE 5-continued

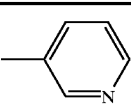

(I)

| Comp. No. | R¹ | R² | R³ R⁴ | R⁵ | R⁶ | Physical property |
|---|---|---|---|---|---|---|
| 50 | H | H | 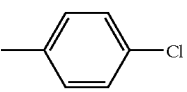 (3-pyridyl) | H | H | mp 175° C. (decomposed) |
| 51 | H | H | 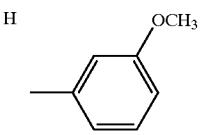 (4-chlorophenyl) | H | H | mp 188° C. (decomposed) |

TABLE 6

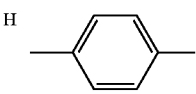

(I)

| Comp. No. | R¹ | R² | R³ | R⁴ | R⁵ | R⁶ | Physical property |
|---|---|---|---|---|---|---|---|
| 52 | H | H | H | 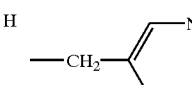 (3-methoxyphenyl) | H | H | mp 144° C. |
| 53 | H | H | H | 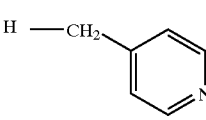 (4-fluorophenyl) | H | H | mp 183.5° C. (decomposed) |
| 54 | H | H | H | —CH₂— (3-pyridylmethyl) | H | H | mp 180° C. (decomposed) |
| 55 | H | H | H | —CH₂— (4-pyridylmethyl) | H | H | mp 176° C. (decomposed) |
| 56 | H | H | H | 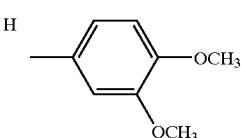 (3,4-dimethoxyphenyl) | H | H | mp 148° C. |
| 57 | H | H | H | 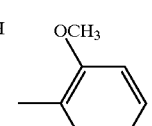 (2-methoxyphenyl) | H | H | mp 135.5–136° C. |

TABLE 6-continued $$\underset{R^5}{\overset{R^1}{\underset{|}{N}}}\underset{|}{\overset{|}{\underset{N}{N}}}\underset{R^3}{\overset{R^2}{\underset{|}{R^3}}}$$ (I)

O$_2$N(R$^6$)C=C, N—R$^4$

| Comp. No. | R$^1$ | R$^2$ | R$^3$ | R$^4$ | R$^5$ | R$^6$ | Physical property |
|---|---|---|---|---|---|---|---|
| 58 | H | H | H | —CH$_2$CH$_2$—C$_6$H$_5$ | H | H | mp 177° C. (decomposed) |
| 59 | H | H | H | —CH$_2$CH$_2$-(2-thienyl) | H | H | mp 180° C. (decomposed) |
| 60 | H | H | H | —CH$_2$-(2-furyl) | H | H | mp 130° C. |
| 61 | H | H | H | —C$_6$H$_4$-OCF$_3$ | H | H | mp 161° C. (decomposed) |
| 62 | H | H | H | —CH$_2$CH$_2$OCH$_3$ | H | H | mp 81–83° C. |
| 63 | H | H | H | —(CH$_2$)$_3$OC$_2$H$_5$ | H | H | Oily |

TABLE 7

$$\underset{R^5}{\overset{R^1}{\underset{|}{N}}}\underset{|}{\overset{|}{\underset{N}{N}}}\underset{R^3}{\overset{R^2}{\underset{|}{R^3}}}$$ (I)

O$_2$N(R$^6$)C=C, N—R$^4$

| Comp. No. | R$^1$ | R$^2$ | R$^3$ | R$^4$ | R$^5$ | R$^6$ | Physical property |
|---|---|---|---|---|---|---|---|
| 64 | H | H | H | —CH(CH$_3$)—C$_6$H$_5$ | H | H | mp 148° C. (decomposed) |
| 65 | H | H | H | cyclopentyl | H | H | mp 142° C. (decomposed) |
| 66 | H | H | H | —NH2 | H | H | mp 154° C. (decomposed) |
| 67 | H | H | H | —N(morpholino) | H | H | mp 187° C. (decomposed) |

TABLE 7-continued $$O_2N(R^6)C=C\begin{array}{c}N-N\\|\phantom{-}\phantom{N}|\\R^1\phantom{N}R^2\\\phantom{O_2N(R^6)C=C}|\\\phantom{O_2N(R^6)C=C}N-R^4\\\phantom{O_2N(R^6)C=C}|\\\phantom{O_2N(R^6)C=C}R^5\end{array}$$ (I)

| Comp. No. | $R^1$ | $R^2$ | $R^3$ | $R^4$ | $R^5$ | $R^6$ | Physical property |
|---|---|---|---|---|---|---|---|
| 68 | H | H | H | —N(piperidinyl) | H | H | mp 179° C. (decomposed) |
| 69 | H | H | H | —N(4-methylpiperazinyl) | H | H | mp 160° C. (decomposed) |
| 70 | H | H | H | —C₆H₄—OCH₂CH₃ (4-) | H | H | mp 198° C. (decomposed) |
| 71 | H | H | H | —C₆H₄—OCH₂CH₂CH₃ (4-) | H | H | mp 179° C. (decomposed) |
| 72 | H | H | H | —C₆H₄—SCH₃ (4-) | H | H | mp 177° C. (decomposed) |
| 73 | H | H | H | —C₆H₄—CH₂COOCH₂CH₂ (4-) | H | H | mp 68–70° C. |
| 74 | H | H | H | —C₆H₄—COOCH₂CH₃ (4-) | H | H | mp 155° C. (decomposed) |
| 75 | H | H | H | —C₆H₄—CH₂CONHOH (4-) | H | H | mp 206° C. (decomposed) |

TABLE 8

$$O_2N(R^6)C=C\begin{array}{c}N-N\\|\phantom{-}\phantom{N}|\\R^1\phantom{N}R^2\\\phantom{O_2N(R^6)C=C}|\\\phantom{O_2N(R^6)C=C}N-R^4\\\phantom{O_2N(R^6)C=C}|\\\phantom{O_2N(R^6)C=C}R^5\end{array}$$ (I)

| Comp. No. | $R^1$ | $R^2$ | $R^3$ | $R^4$ | $R^5$ | $R^6$ | Physical property |
|---|---|---|---|---|---|---|---|
| 76 | H | H | H | —C₆H₄—OH (4-) | H | H | mp 190° C. (decomposed) |

TABLE 8-continued $$O_2N(R^6)C=C\begin{smallmatrix}R^1\\|\\N-N\\\phantom{xx}|\\\phantom{xx}N-R^4\\\phantom{xx}|\\\phantom{xx}R^5\end{smallmatrix}\begin{smallmatrix}R^2\\R^3\end{smallmatrix}\quad(I)$$

| Comp. No. | R¹ | R² | R³ | R⁴ | R⁵ | R⁶ | Physical property |
|---|---|---|---|---|---|---|---|
| 77 | H | H | H | —CH₂—(3-CF₃-C₆H₄) | H | H | mp 155° C. |
| 78 | H | H | H | —CH₂—(4-CF₃-C₆H₄) | H | H | mp 162° C. |
| 79 | H | H | H | —CH₂—(2-pyridyl) | H | H | mp 190° C. (decomposed) |
| 80 | H | H | H | —CH₂—(3,5-Cl₂-C₆H₃) | H | H | mp 203° C. (decomposed) |
| 81 | H | H | H | —CH₂—(2-CF₃-C₆H₄) | H | H | mp 160–161° C. |
| 82 | H | CH₃ | H | CH₃ | H | H | mp 130° C. (decomposed) |
| 83 | H | CH₃ | CH₃ | CH₃ | H | H | mp 135–139° C. |
| 84 | H | H | Ph | CH₃ | H | H | mp 178° C. (decomposed) |
| 85 | H | H | H | —Bu(n) | H | H | mp 118–120.5° C. |
| 86 | H | H | H | —cyclohexyl | H | H | mp 196° C. (decomposed) |
| 87 | H | H | H | —C₆H₅ | H | H | mp 153° C. (decomposed) |

TABLE 9

$$O_2N(R^6)C=C\begin{smallmatrix}R^1\\N-N\\|\\|\\N-R^4\\R^5\end{smallmatrix}\begin{smallmatrix}R^2\\R^3\end{smallmatrix}$$ (I)

| Comp. No. | R¹ | R² | R³ | R⁴ | R⁵ | R⁶ | Physical property |
|---|---|---|---|---|---|---|---|
| 88 | H | H | H | —CH(CH₃)₂ | H | H | mp 172° C. (decomposed) |
| 89 | H | H | H | —Pr(n) | H | H | mp 104–106° C. |
| 90 | H | H | H | cyclopropyl-CH₂ | H | H | mp 145° C. (decomposed) |
| 91 | H | H | H | cyclopentyl-CH₂ | H | H | mp 192° C. (decomposed) |
| 92 | H | H | H | —CH₂-phenyl | H | H | mp 140–143° C. |
| 93 | H | H | H | CH₃ | H | H | mp 190° C. (decomposed) |
| 94 | H | 4-CF₃-6-methyl-pyridin-2-yl | H | CH₃ | H | H | mp 174–175° C. (decomposed) |
| 95 | H | 4-OCF₃-phenyl | H | CH₃ | H | H | mp 176–177° C. (decomposed) |
| 96 | H | 3-NO₂-5-CF₃-6-methyl-pyridin-2-yl | H | CH₃ | H | H | mp 165–167° C. (decomposed) |
| 97 | H | 4-CF₃-6-methyl-pyrimidin-2-yl | H | CH₃ | H | H | mp 217~218° C. (decomposed) |
| 98 | H | 4-CF₃-6-methyl-2-OCH₃-pyridinyl | H | CH₃ | H | H | mp 193° C. (decomposed) |

TABLE 10

$$O_2N(R^6)C=C \begin{array}{c} R^1\phantom{xx}R^2 \\ \diagdown N-N \diagdown \\ \phantom{xxxxxx}R^3 \\ \diagup \\ N-R^4 \\ | \\ R^5 \end{array} \quad (I)$$

| Comp. No. | R¹ | R² | R³ | R⁴ | R⁵ | R⁶ | Physical property |
|---|---|---|---|---|---|---|---|
| 99 | H | 4-methyl-2,6-bis(CF₃)-pyridin-3-yl | H | CH₃ | H | H | mp 180–181° C. (decomposed) |
| 100 | H | 4-CF₃-6-methyl-2-(OCH₂CH₂N(CH₃)₂)-pyridin-3-yl | H | CH₃ | H | H | mp 125–126° C. (decomposed) |
| 101 | H | 4-OCH₃-6-methyl-2-OCH₃-pyrimidin-5-yl | H | CH₃ | H | H | mp 160–162° C. (decomposed) |
| 102 | H | 4-CF₃-6-methyl-2-Cl-pyridin-3-yl | H | CH₂CH₃ | H | H | mp 206° C. (decomposed) |
| 103 | H | 4-CF₃-6-methyl-2-Cl-pyridin-3-yl | H | H | H | H | mp 201–202° C. (decomposed) |
| 104 | H | 2-OCH₃-6-methyl-4-OCH₃-1,3,5-triazin-yl | H | CH₃ | H | H | mp 202–203° C. (decomposed) |
| 105 | H | 4-OMe-2-methyl-6-OMe-pyrimidin-5-yl | H | CH₃ | H | H | mp 166–167° C. (decomposed) |
| 106 | H | 4-CF₃-6-methyl-2-OCH₂CH₃-pyridin-3-yl | H | CH₃ | H | H | mp 185–186° C. (decomposed) |

TABLE 10-continued
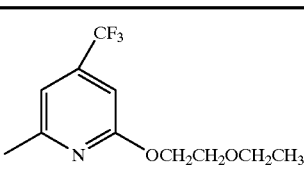
(I)
| Comp. No. | R¹ | R² | R³ | R⁴ | R⁵ | R⁶ | Physical property |
|---|---|---|---|---|---|---|---|
| 107 | H | 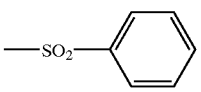 | H | CH₃ | H | H | mp 167–168° C. (decomposed) |
| 108 | H | —SO₂CH₃ | H | CH₃ | H | H | mp 167–168° C. (decomposed) |
| 109 | H | 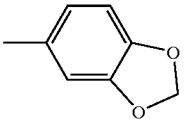 | H | CH₃ | H | H | mp 169–170° C. (decomposed) |
TABLE 11
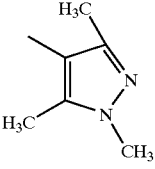
(I)
| Comp. No. | R¹ | R² | R³ | R⁴ | R⁵ | R⁶ | Physical property |
|---|---|---|---|---|---|---|---|
| 110 | H | H | H | 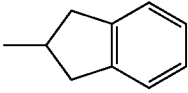 | H | H | mp 177–180° C. (decomposed) |
| 111 | H | H | H | 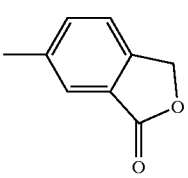 | H | H | mp 210–214° C. (decomposed) |
| 112 | H | H | H | (indane) | H | H | mp 193–197° C. (decomposed) |
| 113 | H | H | H | (isobenzofuranone) | H | H | mp 196–199° C. (decomposed) |

TABLE 11-continued
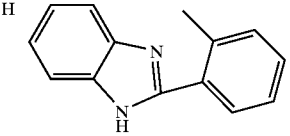
(I)
| Comp. No. | R¹ | R² | R³ | R⁴ | R⁵ | R⁶ | Physical property |
|---|---|---|---|---|---|---|---|
| 114 | H | H | H | 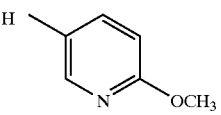 | H | H | mp 212.5° C. |
| 115 | H | H | H | 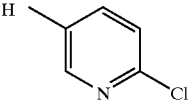 | H | H | mp 162–165 ° C. |
| 116 | H | H | H | 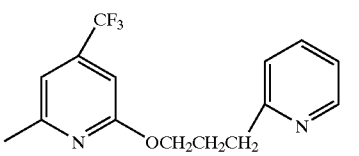 | H | H | mp 180–183° C. |
| 117 | H | H | H | —CH₂CH₃ | H | H | mp 93.5–98.5° C. |
| 118 | H | 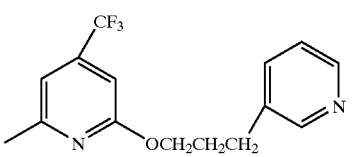 | H | CH₃ | H | H | mp 169° C. (decomposed) |
| 119 | H | 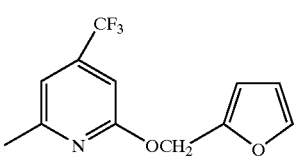 | H | CH₃ | H | H | mp 149° C. (decomposed) |
| 120 | H |  | H | CH₃ | H | H | mp 154° C. (decomposed) |

TABLE 12

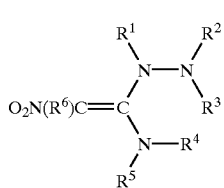

| Comp. No. | R¹ | R² | R³ | R⁴ | R⁵ | R⁶ | Physical property |
|---|---|---|---|---|---|---|---|
| 121 | H | 6-methyl-4-CF₃-pyridin-2-yl-SCH₂-(furan-2-yl) | H | CH₃ | H | H | mp 176° C. (decomposed) |
| 122 | H | 6-methyl-4-CF₃-pyridin-2-yl-OCH₂-(pyridin-2-yl) | H | CH₃ | H | H | mp 170° C. (decomposed) |
| 123 | H | 6-methyl-4-CF₃-pyridin-2-yl-OCH₂-(pyridin-3-yl) | H | CH₃ | H | H | mp 131° C. (decomposed) |
| 124 | H | 6-methyl-4-CF₃-pyridin-2-yl-OCH₂CH₂-(pyridin-2-yl) | H | CH₃ | H | H | mp 181° C. (decomposed) |
| 125 | H | 6-methyl-4-CF₃-pyridin-2-yl-SCH₃ | H | CH₃ | H | H | mp 192° C. (decomposed) |
| 126 | H | 6-methyl-4-CF₃-pyridin-2-yl-O-phenyl | H | CH₃ | H | H | mp 141° C. (decomposed) |
| 127 | H | 2-methylquinolin-yl | H | CH₃ | H | H | mp 202° C. (decomposed) |
| 128 | H | 6-methyl-4-CF₃-pyridin-2-yl-OCH₂-(tetrahydropyran-2-yl) | H | CH₃ | H | H | mp 93–95° C. |

TABLE 12-continued
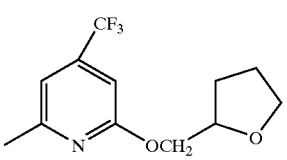
(I)
| Comp. No. | R¹ | R² | R³ | R⁴ | R⁵ | R⁶ | Physical property |
|---|---|---|---|---|---|---|---|
| 129 | H | 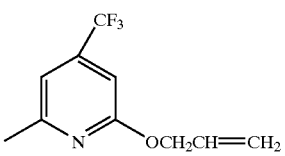 | H | CH₃ | H | H | mp 97–99° C. |
| 130 | H | 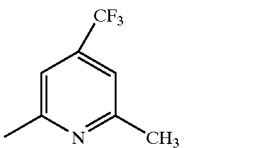 | H | CH₃ | H | H | mp 175° C. (decomposed) |
| 131 | H | 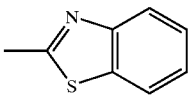 | H | CH₃ | H | H | mp 165° C. (decomposed) |
TABLE 13
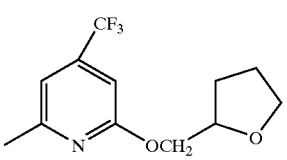
(I)
| Comp. No. | R¹ | R² | R³ | R⁴ | R⁵ | R⁶ | Physical property |
|---|---|---|---|---|---|---|---|
| 132 | H | 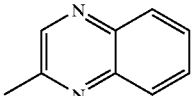 | H | CH₃ | H | H | mp 158° C. (decomposed) |
| 133 | H | 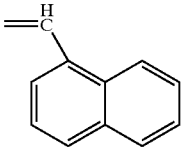 | H | CH₃ | H | H | mp 209° C. (decomposed) |
| 134 | H |  |  | CH₃ | H | H | mp 186° C. (decomposed) |

TABLE 13-continued $$\underset{R^5}{\overset{R^1}{\underset{|}{N}}}\underset{|}{\overset{R^2}{\underset{|}{N}}}\underset{R^3}{\overset{R^2}{\underset{|}{N}}}$$

O$_2$N(R$^6$)C=C, with N—R$^4$ (I)

| Comp. No. | R$^1$ | R$^2$ | R$^3$ | R$^4$ | R$^5$ | R$^6$ | Physical property |
|---|---|---|---|---|---|---|---|
| 135 | H | =CH–(2-naphthyl) | | CH$_3$ | H | H | mp 190° C. (decomposed) |
| 136 | H | =CH–(4-chlorophenyl) | | CH$_3$ | H | H | mp 186° C. (decomposed) |
| 137 | H | =CH–(4-methylphenyl) | | CH$_3$ | H | H | mp 172° C. (decomposed) |
| 138 | H | =CH–(4-nitrophenyl) | | CH$_3$ | H | H | mp 232° C. (decomposed) |
| 139 | H | =CH–(4-biphenyl) | | CH$_3$ | H | H | mp 187° C. (decomposed) |
| 140 | H | =CH–(1,3-benzodioxol-5-yl) | | CH$_3$ | H | H | mp 180° C. (decomposed) |
| 141 | H | =CH–(2,3-dihydro-1,4-benzodioxin-6-yl) | | CH$_3$ | H | H | mp 179° C. (decomposed) |
| 142 | H | =CH–(4-carboxyphenyl) | | CH$_3$ | H | H | mp 210° C. (decomposed) |

TABLE 14

(I)

| Comp. No. | R¹ | R² | R³ | R⁴ | R⁵ | R⁶ | Physical property |
|---|---|---|---|---|---|---|---|
| 143 | H | 4-(benzyloxy)styryl | | CH₃ | H | H | mp 173° C. (decomposed) |
| 144 | H | 3-phenyl-1,2-propadien-1-yl | | CH₃ | H | H | mp 180° C. (decomposed) |
| 145 | H | (6-chloropyridin-2-yl)methyl | H | CH₃ | H | H | mp 221° C. (decomposed) |
| 146 | H | (7-chloro-4-quinolinyl)methyl | H | CH₃ | H | H | mp 210° C. (decomposed) |
| 147 | H | (7-trifluoromethyl-4-quinolinyl)methyl | H | CH₃ | H | H | mp 235° C. (decomposed) |
| 148 | H | (2-phenyl-4-quinazolinyl)methyl | H | CH₃ | H | H | mp 272° C. (decomposed) |
| 149 | H | (2-methyl-4-quinolinyl)methyl | H | CH₃ | H | H | mp 145° C. (decomposed) |
| 150 | H | (1-methylsulfonyl-naphthalen-2-yl)methyl | H | CH₃ | H | H | mp 168° C. (decomposed) |
| 151 | H | (2-methylsulfonyl-naphthalen-2-yl)methyl | H | CH₃ | H | H | mp 129–130° C. |

TABLE 14-continued $$O_2N(R^6)C=C\begin{array}{c}R^1\\N-N\\|\\N-R^4\\R^5\end{array}\begin{array}{c}R^2\\R^3\end{array}\qquad(I)$$

| Comp. No. | R¹ | R² | R³ | R⁴ | R⁵ | R⁶ | Physical property |
|---|---|---|---|---|---|---|---|
| 152 | H | H | H | 6-methyl-1H-indazolyl | H | H | mp 209–213° C. (decomposed) |
| 153 | H | H₂N-pyrazole-COOC₂H₅ | H | phenyl | H | H | mp 128–130° C. |

TABLE 15

| Comp. No. | Compound of the general formula (I) | Physical property |
|---|---|---|
| 154 | O₂N-CH=C-triazolopyridine with CH₃ | mp 126–127° C. |
| 155 | O₂N-CH=C(NH-N=)-CH₃ with N-phenyl, =CH₂ | mp 168–170° C. (decomposed) |

TABLE 16

$$O_2N(R^6)C=C\begin{array}{c}R^1\\N-N\\|\\N-R^4\\R^5\end{array}\begin{array}{c}R^2\\R^3\end{array}\qquad(I)$$

| Comp. No. | R¹ | R² | R³ | R⁴ | R⁵ | R⁶ | Physical property |
|---|---|---|---|---|---|---|---|
| 156 | H | H | H | —SO₂—phenyl | H | H | mp 210° C. (decomposed) |
| 157 | H | 4-CF₃-6-methyl-2-chloropyridyl | H | —SO₂CH₃ | H | H | mp 190° C. (decomposed) |

TABLE 16-continued $$\underset{R^5}{\overset{R^1}{\underset{|}{O_2N(R^6)C}}}=\underset{\underset{R^5}{\overset{|}{N-R^4}}}{\overset{R^1}{\underset{|}{\overset{N-N}{\underset{|}{C}}}\overset{R^2}{\underset{R^3}{}}}}\quad (I)$$

| Comp. No. | R¹ | R² | R³ | R⁴ | R⁵ | R⁶ | Physical property |
|---|---|---|---|---|---|---|---|
| 158 | H | benzoxazol-2-ylmethyl | H | CH₃ | H | H | mp 220–223° C. |
| 159 | H | (2-chloro-4-trifluoromethylpyridin-6-yl)methyl | H | —SO₂—phenyl | H | H | mp 170–173° C. (decomposed) |
| 160 | H | (2-chloro-4-trifluoromethylpyridin-6-yl)methyl | H | —CH₂CH₂OCH₃ | H | H | mp 175–178° C. (decomposed) |

TABLE 17

$$\underset{R^5}{\overset{R^1}{\underset{|}{O_2N(R^6)C}}}=\underset{\underset{R^5}{\overset{|}{N-R^4}}}{\overset{R^1}{\underset{|}{\overset{N-N}{\underset{|}{C}}}\overset{R^2}{\underset{R^3}{}}}}\quad (I)$$

| Comp. No. | R¹ | R² | R³ | R⁴ | R⁵ | R⁶ | Physical property |
|---|---|---|---|---|---|---|---|
| 161 | H | (2-chloro-4-trifluoromethylpyridin-6-yl)methyl | H | —SO₂CH₂CH₃ | H | H | mp 114–119° C. (decomposed) |
| 162 | H | (2-chloro-4-trifluoromethylpyridin-6-yl)methyl | H | —SO₂-biphenyl | H | H | mp 171–174° C. |
| 163 | H | tetrahydropyran-yl | | —SO₂-phenyl | H | H | mp 127–130° C. |

TABLE 17-continued $$O_2N(R^6)C=C\begin{matrix}N-N\\|\\N-R^4\\|\\R^5\end{matrix}\begin{matrix}R^1\\R^2\\R^3\end{matrix}$$ (I)

| Comp. No. | R¹ | R² | R³ | R⁴ | R⁵ | R⁶ | Physical property |
|---|---|---|---|---|---|---|---|
| 164 | H | 4-CF₃-6-methyl-2-(OCH₂CH₂OC₂H₅)-pyridin-? | H | —SO₂CH₃ | H | H | mp 153° C. |
| 165 | H | 4-CF₃-6-methyl-2-chloropyridinyl | H | —SO₂CH₃ | H | CH₃ | mp 30–33° C. |
| 166 | H | =CH—C₆H₄—CF₃ (para) | | CH₃ | H | H | mp 188–189° C. |
| 167 | H | =CH—C₆H₄—CF₃ (meta) | | CH₃ | H | H | mp 180° C. |
| 168 | H | 2-CF₃-6-methylpyridinyl | H | CH₃ | H | H | mp 197° C. (decomposed) |
| 169 | H | 4-CF₃-6-methyl-2-chloropyridinyl | H | —CH₂-(tetrahydrofuran-2-yl) | H | H | mp 164° C. (decomposed) |
| 170 | H | 4,7-dimethylthieno[3,2-d]pyrimidinyl | H | CH₃ | H | H | mp 216° C. (decomposed) |
| 171 | H | 3-chloro-2-methylpyridinyl | H | CH₃ | H | H | mp 188° C. (decomposed) |

TABLE 18

$$\text{O}_2\text{N}(\text{R}^6)\text{C}=\text{C}\begin{array}{c}\text{R}^1\quad\text{R}^2\\|\quad|\\\text{N}-\text{N}\\|\quad\text{R}^3\\\text{N}-\text{R}^4\\|\\\text{R}^5\end{array}\qquad(I)$$

| Comp. No. | R¹ | R² | R³ | R⁴ | R⁵ | R⁶ | Physical property |
|---|---|---|---|---|---|---|---|
| 172 | H | 2-methyl-5-chloropyridin-... | H | CH₃ | H | H | mp 206° C. (decomposed) |
| 173 | H | 6-methyl-4-(trifluoromethyl)-2-(benzyloxy)pyridin-... | H | CH₃ | H | H | mp 160° C. (decomposed) |
| 174 | H | 6-methyl-4-(trifluoromethyl)-2-(2-chlorobenzyloxy)pyridin-... | H | CH₃ | H | H | mp 162° C. (decomposed) |
| 175 | H | 6-methyl-4-(trifluoromethyl)-2-(2-methoxybenzyloxy)pyridin-... | H | CH₃ | H | H | mp 157° C. (decomposed) |
| 176 | H | 6-methyl-4-(trifluoromethyl)-2-(phenethyloxy)pyridin-... | H | CH₃ | H | H | mp 146° C. |
| 177 | H | 6-methyl-4-(trifluoromethyl)-2-propoxypyridin-... | H | CH₃ | H | H | mp 169° C. (decomposed) |
| 178 | H | 6-methyl-4-(trifluoromethyl)-2-propoxypyridin-... | H | CH₃ | H | H | mp 161° C. (decomposed) |

TABLE 18-continued $$O_2N(R^6)C=C\begin{array}{c}R^1\phantom{xx}R^2\\ \backslash N\!-\!N\diagup\\ |\phantom{xxx}\backslash R^3\\ N\!-\!R^4\\ |\\ R^5\end{array}\qquad(I)$$

| Comp. No. | R¹ | R² | R³ | R⁴ | R⁵ | R⁶ | Physical property |
|---|---|---|---|---|---|---|---|
| 179 | H | =CH—(3-Cl,5-CF₃-pyridin-2-yl) | CH₃ | H | H | H | mp 171° C. (decomposed) |
| 180 | H | (4-CF₃,6-CH₃-pyridin-2-yl)-O-CH₂-cyclohexyl | H | CH₃ | H | H | mp 160° C. (decomposed) |
| 181 | H | (4-CF₃,6-CH₃-pyridin-2-yl)-OCH₂CF₃ | H | CH₃ | H | H | mp 180° C. (decomposed) |
| 182 | H | (3-CF₃,5-CH₃-phenyl)-OCH₂CH₂OCH₃ | H | CH₃ | H | H | mp 138° C. |

TABLE 19

$$O_2N(R^6)C=C\begin{array}{c}R^1\phantom{xx}R^2\\ \backslash N\!-\!N\diagup\\ |\phantom{xxx}\backslash R^3\\ N\!-\!R^4\\ |\\ R^5\end{array}\qquad(I)$$

| Comp. No. | R¹ | R² | R³ | R⁴ | R⁵ | R⁶ | Physical property |
|---|---|---|---|---|---|---|---|
| 183 | H | (4-CF₃,6-CH₃-pyridin-2-yl)-OCH₂CH₂OCH₂-phenyl | H | CH₃ | H | H | mp 135° C. |
| 184 | H | (4-CF₃,6-CH₃-pyridin-2-yl)-OCH₂-cyclopropyl | H | CH₃ | H | H | mp 167° C. (decomposed) |

TABLE 19-continued $$O_2N(R^6)C=C\begin{array}{c}N-N{<}^{R^1}_{R^2}\\|\phantom{xxx}R^3\\N-R^4\\|\\R^5\end{array}\quad (I)$$

| Comp. No. | R¹ | R² | R³ | R⁴ | R⁵ | R⁶ | Physical property |
|---|---|---|---|---|---|---|---|
| 185 | H | 4-CF₃-6-methyl-2-(OCH₂CH₂O-phenyl)-pyridin-3-yl | H | CH₃ | H | H | mp 167° C. (decomposed) |
| 186 | H | 3,5-dichloro-4-methylpyridin-? | H | CH₃ | H | H | mp 197° C. (decomposed) |
| 187 | H | 3,5-dichloro-2-methylpyridin-? | H | CH₃ | H | H | mp 195° C. (decomposed) |
| 188 | H | 4-CF₃-6-methyl-2-(OCH₂CH₂-morpholino)-pyridin-3-yl | H | CH₃ | H | H | mp 166° C. (decomposed) |
| 189 | H | 4-CF₃-6-methyl-2-(OCH₂CH₂SCH₃)-pyridin-3-yl | H | CH₃ | H | H | mp 94° C. |
| 190 | H | 4-CF₃-6-methyl-2-chloropyridin-3-yl | H | CH₂CH₂N(CH₃)₂ | H | H | mp 90° C. |
| 191 | Hydrochloride of Compound No. 190 | | | | | | mp 201° C. (decomposed) |
| 192 | H | 4-CF₃-6-methyl-2-(OCH₂CH₂OCH₂CH₂CH₃)-pyridin-3-yl | H | CH₃ | H | H | mp 128° C. |

TABLE 19-continued

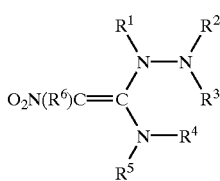
(I)

| Comp. No. | R¹ | R² | R³ | R⁴ | R⁵ | R⁶ | Physical property |
|---|---|---|---|---|---|---|---|
| 193 | H | 4-CF₃-6-methyl-2-(OCH₂CH₂OC(CH₃)₃)-pyridinyl | H | CH₃ | H | H | mp 170° C. (decomposed) |
| 194 | H | 4-CF₃-6-methyl-2-(OCH₂CH₂OCH₂CH₂OCH₃)-pyridinyl | H | CH₃ | H | H | mp 128° C. |

TABLE 20

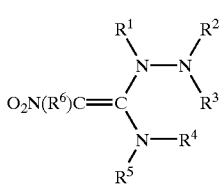
(I)

| Comp. No. | R¹ | R² | R³ | R⁴ | R⁵ | R⁶ | Physical property |
|---|---|---|---|---|---|---|---|
| 195 | H | 4-CF₃-6-methyl-2-(OCH₂CH₂SPh)-pyridinyl | H | CH₃ | H | H | mp 170° C. (decomposed) |
| 196 | H | 4-CF₃-6-methyl-2-(OCH₂CH₂OCH(CH₃)₂)-pyridinyl | H | CH₃ | H | H | mp 167° C. (decomposed) |
| 197 | H | 4-CF₃-6-methyl-2-(OCH₂CH₂CH₂OCH₂CH₃)-pyridinyl | H | CH₃ | H | H | mp 147° C. |
| 198 | H | 4-CF₃-6-methyl-2-chloro-pyridinyl | H | —(CH₂)₃OH | H | H | mp 134–135° C. |

TABLE 20-continued $$O_2N(R^6)C=C \begin{matrix} N(R^1)-N(R^2)(R^3) \\ N(R^5)-R^4 \end{matrix} \quad (I)$$

| Comp. No. | R¹ | R² | R³ | R⁴ | R⁵ | R⁶ | Physical property |
|---|---|---|---|---|---|---|---|
| 199 | H | 2-chloro-4-(trifluoromethyl)-6-methylpyridin-yl | H | —(CH₂)₄OH | H | H | mp 150–151° C. |
| 200 | H | 2,6-dimethyl-4-(trifluoromethyl)pyridin-yl | H | —CH₂-(tetrahydrofuran-2-yl) | H | H | mp 144–145° C. |
| 201 | H | 2,4-bis(trifluoromethyl)-1,8-naphthyridin-7-yl | H | —SO₂CH₃ | H | H | mp 191–193° C. |
| 202 | H | 2,6-dimethyl-4-methyl-3-(methylsulfonyl)pyridin-yl | H | —SO₂CH₃ | H | H | mp 170° C. (decomposed) |
| 203 | H | 5-chloro-2-methylpyridin-yl | H | —SO₂CH₃ | H | H | mp 62–68° C. |
| 204 | H | 5-chloro-2-methylpyridin-yl | H | —CH₂-(tetrahydrofuran-2-yl) | H | H | mp 200° C. (decomposed) |
| 205 | H | 5-bromo-2-methylpyridin-yl | H | CH₃ | H | H | mp 208° C. (decomposed) |

TABLE 21

$$O_2N(R^6)C=C\begin{matrix}R^1\\N-N\\|\phantom{-}\phantom{N}|\\N-R^4\\|\\R^5\end{matrix}\begin{matrix}R^2\\R^3\end{matrix}$$ (I)

| Comp. No. | R¹ | R² | R³ | R⁴ | R⁵ | R⁶ | Physical property |
|---|---|---|---|---|---|---|---|
| 206 | H | 5-bromo-2-methylpyridin-2-yl (5-Br, 2-CH₃-pyridyl) | H | —SO₂CH₃ | H | H | |
| 207 | H | 5-bromo-2-methylpyridin-2-yl | H | —CH₂-(tetrahydrofuran-2-yl) | H | H | mp 206° C. (decomposed) |
| 208 | H | 4-CF₃-2,6-dimethylpyridin-3-yl | H | —SO₂CH₃ | H | H | mp 92–93° C. |
| 209 | H | =CH—(4-CF₃-phenyl) | | —SO₂CH₃ | H | H | mp 188° C. (decomposed) |
| 210 | H | =CH—(4-CF₃-phenyl) | | —CH₂-(tetrahydrofuran-2-yl) | H | H | mp 163° C. |
| 211 | H | =CH—(3-Cl-5-CF₃-pyridin-2-yl) | | —SO₂CH₃ | H | H | mp 236° C. (decomposed) |
| 212 | H | =CH—(3-Cl-5-CF₃-pyridin-2-yl) | | —CH₂-(tetrahydrofuran-2-yl) | H | H | mp 172° C. |
| 213 | H | tetrahydropyran-2-yl | | —CH₂CH(CH₃)₂ | H | H | |
| 214 | H | tetrahydropyran-2-yl | | —CH(CH₃)₂ | H | H | |
| 215 | H | tetrahydropyran-2-yl | | —SO₂CH₃ | H | H | mp 140–142° C. |

TABLE 21-continued
(I)
| Comp. No. | R¹ | R² | R³ | R⁴ | R⁵ | R⁶ | Physical property |
|---|---|---|---|---|---|---|---|
| 216 | H |  | | —SO$_2$C$_2$H$_5$ | H | H | |
| 217 | H | 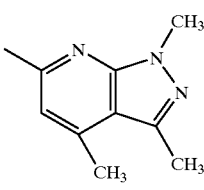 | | 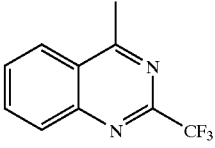 | H | H | |
TABLE 22
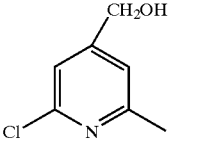
(I)
| Comp. No. | R¹ | R² | R³ | R⁴ | R⁵ | R⁶ | Physical property |
|---|---|---|---|---|---|---|---|
| 218 | H | (1,4,6-trimethylpyrazolo[3,4-b]pyridin-3-yl) | H | —SO$_2$CH$_3$ | H | H | |
| 219 | H | (4-methyl-2-trifluoromethylquinazolin-?-yl) | H | —SO$_2$CH$_3$ | H | H | |
| 220 | H | (6-chloro-2-methyl-4-hydroxymethylpyridin-?-yl) | H | —SO$_2$CH$_3$ | H | H | |

TABLE 22-continued $$O_2N(R^6)C=C\begin{smallmatrix}R^1\phantom{xx}R^2\\|\phantom{xx}|\\N-N\\|\phantom{xx}\diagdown R^3\\|\phantom{xxxxxx}\\N-R^4\\|\\R^5\end{smallmatrix}\qquad(I)$$

| Comp. No. | R¹ | R² | R³ | R⁴ | R⁵ | R⁶ | Physical property |
|---|---|---|---|---|---|---|---|
| 221 | H | 2-chloro-4-methoxy-6-methylpyridin-3-yl | H | —SO₂CH₃ | H | H | |
| 222 | H | 2-chloro-4-ethoxy-6-methylpyridin-3-yl | H | —SO₂CH₃ | H | H | |
| 223 | H | 2-chloro-4-(2-ethoxyethoxy)-6-methylpyridin-3-yl | H | —SO₂CH₃ | H | H | |
| 224 | H | 2-chloro-4-(methoxymethyl)-6-methylpyridin-3-yl | H | —SO₂CH₃ | H | H | |
| 225 | H | 2-chloro-4-(ethoxymethyl)-6-methylpyridin-3-yl | H | —SO₂CH₃ | H | H | |
| 226 | H | 2-chloro-4-(2-ethoxyethoxymethyl)-6-methylpyridin-3-yl | CH₂OCH₂CH₂OCH₂CH₃ | H | —SO₂CH₃ | H | H | |

TABLE 22-continued $$O_2N(R^6)C=C \begin{matrix} R^1 & R^2 \\ N-N \\ & R^3 \\ N-R^4 \\ R^5 \end{matrix} \quad (I)$$

| Comp. No. | R¹ | R² | R³ | R⁴ | R⁵ | R⁶ | Physical property |
|---|---|---|---|---|---|---|---|
| 227 | H | 2-methyl-5-(trifluoromethyl)pyridin-yl | H | —SO₂CH₃ | H | H | |
| 228 | H | 2-methylbenzothiazol-yl | H | —SO₂CH₃ | H | H | |

TABLE 23

$$O_2N(R^6)C=C \begin{matrix} R^1 & R^2 \\ N-N \\ & R^3 \\ N-R^4 \\ R^5 \end{matrix} \quad (I)$$

| Comp. No. | R¹ | R² | R³ | R⁴ | R⁵ | R⁶ | Physical property |
|---|---|---|---|---|---|---|---|
| 229 | H | 2-methyl-5-(trifluoromethyl)pyridin-yl | H | —CH₂-(tetrahydrofuran-2-yl) | H | H | |
| 230 | H | 2-methylquinolin-yl | H | —SO₂CH₃ | H | H | |
| 231 | H | 2-methyl-4-(trifluoromethyl)-6-(2-methoxyethoxy)pyridin-yl | H | —SO₂CH₃ | H | H | |
| 232 | H | 2-methyl-4-(trifluoromethyl)-6-methoxypyridin-yl | H | —SO₂CH₃ | H | H | |
| 233 | H | 2-methyl-6-(trifluoromethyl)pyridin-yl | H | —SO₂CH₃ | H | H | |

TABLE 23-continued $$O_2N(R^6)C=C\begin{smallmatrix}R^1\phantom{xx}R^2\\N-N\\|\phantom{xxx}|\\\phantom{xx}R^3\\N-R^4\\|\\R^5\end{smallmatrix}\quad(I)$$

| Comp. No. | $R^1$ | $R^2$ | $R^3$ | $R^4$ | $R^5$ | $R^6$ | Physical property |
|---|---|---|---|---|---|---|---|
| 234 | H | 6-chloro-2-methylpyridin-3-yl | H | —SO$_2$CH$_3$ | H | H | |
| 235 | H | H | H | —SO$_2$CH$_3$ | H | H | Oily |
| 236 | H | tetrahydropyran-2-yl | H | —CH$_2$-(furan-2-yl) | H | H | mp 160–162° C. (decomposed) |

Preparation Examples of compounds of the above formula (IV) which are intermediates for the preparation of compounds of the above formula (I) prepared by a process in accordance with the above-described Process 1-1, are shown in the following Tables 24 to 29.

TABLE 24

$$O_2N(R^6)C=C\begin{smallmatrix}S-Z\\|\\N-R^4\\|\\R^5\end{smallmatrix}\quad(IV)$$

| Intermediate No. | Z | $R^4$ | $R^5$ | $R^6$ | Physical property |
|---|---|---|---|---|---|
| 1 | CH$_3$ | —CH$_2$CH$_2$CH$_3$ | H | H | mp 63–64° C. |
| 2 | CH$_3$ | cyclopropyl | H | H | mp 101.5–106° C. |
| 3 | CH$_3$ | cyclopentyl | H | H | mp 82–87.5° C. |
| 4 | CH$_3$ | —CH$_2$-phenyl | H | H | mp 101–112° C. |
| 5 | CH$_3$ | —CH$_3$ | H | H | mp 111.5–114.5° C. |
| 6 | CH$_3$ | —CH$_2$CH$_3$ | H | H | mp 65–66.5° C. |
| 7 | CH$_3$ | —CH$_2$CH$_2$CH$_2$CH$_3$ | H | H | mp 50–51° C. |
| 8 | CH$_3$ | cyclohexyl | H | H | mp 105–107° C. |

TABLE 24-continued $$O_2N(R^6)C=C\begin{smallmatrix}S-Z\\|\\N-R^4\\|\\R^5\end{smallmatrix}\quad(IV)$$

| Intermediate No. | Z | $R^4$ | $R^5$ | $R^6$ | Physical property |
|---|---|---|---|---|---|
| 9 | CH$_3$ | —Ph | H | H | mp 140.5–149° C. |
| 10 | CH$_3$ | —CH(CH$_3$)$_2$ | H | H | mp 94–97.5° C. |
| 11 | CH$_3$ | 4-nitrophenyl | H | H | mp 180° C. |

TABLE 25

$$O_2N(R^6)C=C\begin{smallmatrix}S-Z\\|\\N-R^4\\|\\R^5\end{smallmatrix}\quad(IV)$$

| Intermediate No. | Z | $R^4$ | $R^5$ | $R^6$ | Physical property |
|---|---|---|---|---|---|
| 12 | CH$_3$ | 4-hydroxyphenyl | H | H | mp 193° C. (decomposed) |

TABLE 25-continued $$O_2N(R^6)C=C(S-Z)(N(R^4)(R^5))$$ (IV)

| Intermediate No. | Z | R⁴ | R⁵ | R⁶ | Physical property |
|---|---|---|---|---|---|
| 13 | CH₃ | 3-CF₃-C₆H₄-CH₂- | H | H | mp 94–95° C. |
| 14 | CH₃ | —(CH₂)₇CH₃ | H | H | mp 36–38° C. |
| 15 | CH₃ | —(CH₂)₉CH₃ | H | H | mp 42.5–45° C. |
| 16 | CH₃ | 3-pyridyl | H | H | mp 140–142° C. |
| 17 | CH₃ | 4-CH₃-C₆H₄- | H | H | mp 138–141° C. |
| 18 | CH₃ | 4-OCH₃-C₆H₄- | H | H | mp 159–160° C. |
| 19 | CH₃ | 4-Cl-C₆H₄- | H | H | mp 152–155° C. |
| 20 | CH₃ | 3-OCH₃-C₆H₄- | H | H | mp 118–121° C. |
| 21 | CH₃ | 4-F-C₆H₄- | H | H | mp 156° C. |
| 22 | CH₃ | 3-pyridyl-CH₂- | H | H | mp 131–132° C. |
| 23 | CH₃ | 4-pyridyl-CH₂- | H | H | mp 99–101° C. |

TABLE 26

$$O_2N(R^6)C=C(S-Z)(N(R^4)(R^5))$$ (IV)

| Intermediate No. | Z | R⁴ | R⁵ | R⁶ | Physical property |
|---|---|---|---|---|---|
| 24 | CH₃ | 3,4-di-OCH₃-C₆H₃- | H | H | mp 159.5–160° C. |
| 25 | CH₃ | 2-OCH₃-C₆H₄- | H | H | mp 128–130° C. |
| 26 | CH₃ | —CH₂COOCH₂CH₃ | H | H | mp 79–81° C. |
| 27 | CH₃ | —CH₂CH₂-C₆H₅ | H | H | mp 89–91° C. |
| 28 | CH₃ | —CH₂CH₂-(2-thienyl) | H | H | mp 75–76° C. |
| 29 | CH₃ | —CH₂-(2-furyl) | H | H | mp 97.5–98.5° C. |
| 30 | CH₃ | 4-OCF₃-C₆H₄- | H | H | mp 114–116° C. |
| 31 | CH₃ | —CH₂CH₂OCH₃ | H | H | mp 96–97° C. |
| 32 | CH₃ | —(CH₂)₃OCH₂CH₃ | H | H | Oily |
| 33 | CH₃ | —CH(CH₃)-C₆H₅ | H | H | mp 117–119° C. |
| 34 | CH₃ | cyclopentyl | H | H | mp 63–68° C. |
| 35 | CH₃ | cyclohexyl | H | H | mp 38–42° C. |

TABLE 27
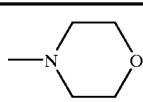
(IV)
| Intermediate No. | Z | R⁴ | R⁵ | R⁶ | Physical property |
|---|---|---|---|---|---|
| 36 | $CH_3$ | 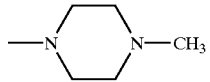 | H | H | mp 174–175° C. |
| 37 | $CH_3$ | 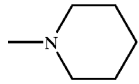 | H | H | mp 140–141° C. |
| 38 | $CH_3$ | 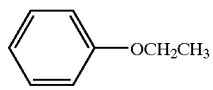 | H | H | mp 142–143° C. |
| 39 | $CH_3$ | 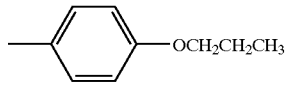 | H | H | mp 164–165° C. |
| 40 | $CH_3$ | 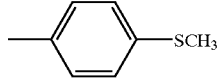 | H | H | mp 155–155.5° C. |
| 41 | $CH_3$ | 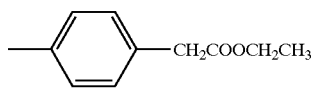 | H | H | mp 156.5–157° C. |
| 42 | $CH_3$ | 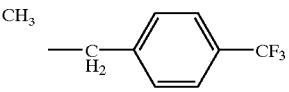 | H | H | mp 105–106° C. |
| 43 | $CH_3$ | 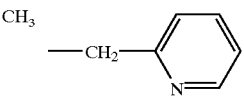 | H | H | mp 139–140° C. |
| 44 | $CH_3$ | 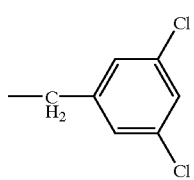 | H | H | mp 144° C. (decomposed) |
| 45 | $CH_3$ | 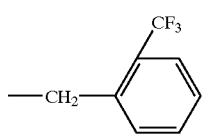 | H | H | mp 157–158° C. |
| 46 | $CH_3$ |  | H | H | mp 135–137° C. |

TABLE 28

(IV)

$$O_2N(R^6)C=C(S-Z)(N(R^4)(R^5))$$

| Intermediate No. | Z | R⁴ | R⁵ | R⁶ | Physical property |
|---|---|---|---|---|---|
| 47 | CH₃ | 5-methyl-2-chloropyridin-yl | H | H | mp 169–172° C. |
| 48 | CH₃ | 2-(2-methylphenyl)-1H-benzimidazol-5-yl | H | H | mp 204–206° C. (decomposed) |
| 49 | CH₃ | 5-methyl-2-methoxypyridin-yl | H | H | mp 134–137° C. |
| 50 | CH₃ | 4-(ethoxycarbonyl)phenyl | H | H | mp 116–123° C. |
| 51 | CH₃ | benzo[1,3]dioxol-5-yl | H | H | mp 153–155° C. |
| 52 | CH₃ | 3-oxo-2,3-dihydrobenzofuran-5-yl | H | H | mp 221–222° C. (decomposed) |
| 53 | CH₃ | 2,3-dihydro-1H-inden-2-yl | H | H | mp 196–197° C. |
| 54 | CH₃ | 1,3,4,5-tetramethyl-1H-pyrazol-yl | H | H | mp 184–188° C. |
| 55 | CH₃ | 6-methyl-1H-indazol-yl | H | H | mp 214–216° C. |
| 56 | CH₃ | —SO₂Ph | H | H | Oily |
| 57 | CH₃ | —SO₂CH₃ | H | H | mp 81–82° C. |

TABLE 29

$$O_2N(R^6)C=C\begin{smallmatrix}S-Z\\ \\N-R^4\\|\\R^5\end{smallmatrix}$$ (IV)

| Intermediate No. | Z | R⁴ | R⁵ | R⁶ | Physical property |
|---|---|---|---|---|---|
| 58 | CH₃ | —SO₂—C₆H₄—OPh | H | H | |
| 59 | CH₃ | —SO₂CH₂CH₃ | H | H | Oily |
| 60 | CH₃ | 5-(dimethylamino)naphthalen-1-ylsulfonyl (dansyl) | H | H | mp 189–191° C. (decomposed) |
| 61 | CH₃ | naphthalen-2-ylsulfonyl | H | H | mp 205° C. (decomposed) |
| 62 | CH₃ | 4-biphenylsulfonyl | H | H | mp 75–77° C. |
| 63 | CH₃ | —OCH₃ | H | H | nD 1.5150 (30° C.) |
| 64 | CH₃ | —SO₂CH₃ | H | H | nD 1.5150 (30° C.) |
| 65 | CH₃ | —SO₂CH₃ | H | H | nD 1.5286 |
| 66 | CH₃ | tetrahydrofuran-2-ylmethyl | H | H | Oily |
| 67 | CH₃ | —CH₂CH₂N(CH₃)₂ | H | H | |
| 68 | CH₃ | —CH₂CH₂CH₂OH | H | H | |
| 69 | CH₃ | —CH₂CH₂CH₂CH₂OH | H | H | |
| 70 | CH₃ | —CH₂CH(CH₃)₂ | H | H | mp 52–54° C. |

Among the compounds of the above formula (V) as intermediates to be used for the above Processes 1, 2 and 4, compounds represented by the formula (V'):

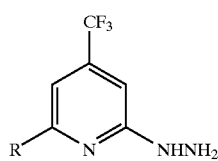

wherein R is as defined below, which are compounds wherein Y, R¹ and R³ is a hydrogen atom, and R² is:

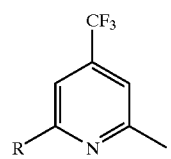

wherein R is a halogen atom (provided that a chlorine atom is excluded) or an organic group (provided that a trifluoromethyl group, a methyl group, a phenyl group and a thienyl group are excluded), are novel compounds and can be prepared by a method in accordance with above Preparation Example 3(1). Specific Preparation Examples thereof are shown in Tables 30 to 33.

TABLE 30

(V')

Structure: Pyridine with CF₃ at 4-position, R at 6-position, NHNH₂ at 2-position.

| Intermediate No. | R | Physical property |
|---|---|---|
| 71 | CH₃O— | mp 52–53° C. |
| 72 | CH₃CH₂O— | mp 72–76° C. |

TABLE 31

(V')

Structure: Pyridine with CF₃ at 4-position, R at 6-position, NHNH₂ at 2-position.

| Intermediate No. | R | Physical property |
|---|---|---|
| 73 | phenyl-O— | Oily |
| 74 | CH₃CH₂OCH₂CH₂O— | mp 48–49° C. |
| 75 | (CH₃)₂N—CH₂CH₂O— | mp 96–97° C. |
| 76 | CH₃S— | mp 102–103° C. |
| 77 | —OCH₂CH₂CH₂-(2-pyridyl) | mp 55–58° C. |
| 78 | —OCH₂CH₂CH₂-(3-pyridyl) | mp 59–60° C. |
| 79 | —OCH₂-(2-furyl) | Oily |
| 80 | —SCH₂-(2-furyl) | mp 77–80° C. |
| 81 | —OCH₂-(2-pyridyl) | mp 70–73° C. |
| 82 | —OCH₂-(3-pyridyl) | mp 118–119° C. |

TABLE 31-continued (V')

| Intermediate No. | R | Physical property |
|---|---|---|
| 83 | —OCH₂CH₂-(2-pyridyl) | mp 98–100° C. |
| 84 | —OCH₂-(tetrahydropyran-2-yl) | mp 79–81° C. |

TABLE 32

(V')

| Intermediate No. | R | Physical property |
|---|---|---|
| 85 | —OCH₂-(tetrahydrofuran-2-yl) | mp 96–97° C. |
| 86 | —OCH=CH₂ | Oily |
| 87 | —OCH₂-phenyl | mp 33–34° C. |
| 88 | —OCH₂-(2-chlorophenyl) | mp 123° C. |
| 89 | —OCH₂-(2-methoxyphenyl) | mp 86–87° C. |
| 90 | —OCH₂CH₂-phenyl | mp 51–55° C. |
| 91 | —OCH₂CH₂CH₃ | mp 51–52° C. |
| 92 | —OCH₂CH₂CH₂CH₃ | mp 33–35° C. |

TABLE 32-continued (V')

Structure: Pyridine with CF₃ at 4-position, R at 6-position, NHNH₂ at 2-position

| Intermediate No. | R | Physical property |
|---|---|---|
| 93 | —OCH₂—(cyclohexyl) | mp40–42° C. |
| 94 | —OCH₂CF₃ | mp71–72° C. |
| 95 | —OCH₂CH₂OCH₃ | mp39–40° C. |
| 96 | —OCH₂CH₂OCH₂—(phenyl) | oily |
| 97 | —OCH₂—(cyclopropyl) | mp63–64° C. |

TABLE 33

(V')

Structure: Pyridine with CF₃ at 4-position, R at 6-position, NHNH₂ at 2-position

| Intermediate No. | R | Physical property |
|---|---|---|
| 98 | —OCH₂CH₂O—(phenyl) | mp72–73° C. |
| 99 | —OCH₂CH₂—N(morpholino) | mp64–66° C. |
| 100 | —OCH₂CH₂SCH₃ | mp55–56° C. |
| 101 | —OCH₂CH₂OCH₂CH₂CH₃ | Oily |
| 102 | —OCH₂CH₂OC(CH₃)₂ | mp100–101° C. |
| 103 | —OCH₂CH₂OCH₂CH₂OCH₃ | Oily |
| 104 | —OCH₂CH₂S—(phenyl) | mp44–45° C. |
| 105 | —OCH₂CH₂OCH(CH₃)₂ | mp62–63° C. |
| 106 | —OCH₂CH₂CH₂OCH₂CH₃ | Oily |

Nitroetheneamine derivatives represented by the above formula (I) or salts thereof have matrix metalloproteinase inhibition activities, particularly MMP-1, MMP-2, MMP-3, MMP-7 and MMP-9 inhibition activities. Among them, MMP-3- and MMP-9 inhibition activities are particularly excellent, and MMP-9 inhibition activities are the best. Not only the compounds of the above formula (I) and salts thereof, compounds of the above formula (IV) or salts thereof, which are intermediates for the preparation of the compounds of the above formula (I) have the above-described matrix metalloproteinase inhibition activities. Accordingly, by using them as active constituents and by combining the after-mentioned carrier, etc., as the case requires, matrix metalloproteinase inhibitors of the present invention can be provided. Further, a medical composition will be provided which comprises a therapeutically effective amount of the compound of the above formula (I) or a salt thereof, or the compound of the above formula (IV) or a salt thereof and a pharmaceutically acceptable carrier. To apply the pharmaceutical composition of the present invention to clinical treatment as an angiogenesis inhibitor, an anticancer agent, a tumor cell infiltration inhibitor or a tumor metastatis inhibitor to be used for treatment or prevention of a cancer or inflammatory diseases or as a therapeutic or preventive agent for rheumatoid arthritis, it is preferred to make it a formulation having an additive such as a diluent, an excipient or a stabilizer further incorporated as the case requires to the medical composition comprising the above active constituent and the pharmaceutical acceptable carrier.

In the medical composition of the present invention, the blend proportion of the above active constituent to the carrier component is usually from 1.0 to 90% w/w. The dosage effective for treatment is usually from 0.1 to 1000 mg/day/person in the case of an adult, although it varies depending upon e.g. the administration method, the sex, the weight and the age of the patient and the disease to be treated.

With respect to the formulation and the administration mode, it may be orally administered in the form of a formulation such as a granule, a loose granule or a pilula, a tablet, a capsule or a solution or in the form of a bulk powder, or it may be administered by non-oral route in the form of a suppository, an aerosol or formulation for local administration such as collunarium. As an injection solution, it may be administered by intravenous administration, intramuscular administration, subcutaneous administration or articular cavity administration. Further, it may be prepared in the form of a powder for injection and may be formulated at the time of use.

A pharmaceutical, organic or inorganic, solid or liquid carrier or diluent suitable for oral, enteral or perenteral administration can be used for formulating the medical composition of the present invention. A typical carrier or diluent which can be incorporated to tablets or capsules, may be a disintegrant such as Acacia, corn starch or alginic acid, a lubricant such as magnesium stearate or a sweetener such as saccharose or lactose. When the formulation is capsules, in addition to the above substance, a liquid carrier such as fatty oil may be incorporated. Various other substances can be used as a coating agent or a physical shape improving agent for a dosage unit. For example, it is preferred to dissolve or suspend the active ingredient in water or in an excipient such as natural vegetable oil or in a synthetic fatty excipient such as ethyl oleate. A buffer agent such as a citrate, an acetate or a phosphate, or an anti oxidant such as ascorbic acid, may also be incorporated in accordance with an acceptable medical method.

TEST EXAMPLES

Now, specific Test Examples will be described wherein MMP inhibition activities of nitroetheneamine derivatives represented by the above formula (I) were measured.

TEST EXAMPLE 1

Measurement of the Enzyme Inhibition Activity Against MMP-3 (Stromelysin-1)

The inhibition activity against human MMP-3 was measured using a fluorescent peptide substrate MOCAc-Arg- Pro-Lys-Pro-Val-Glu-Nva-Trp—Arg-Lys(Dnp)-NH$_2$[NFF-3, manufactured by Peptide Institute, Inc. (No. 3168-v)] with reference to the method disclosed in a literature (Knight C. G. et al, FEBS Letters, Vol. 296, 263–266, 1992, Nagase H. et al, Journal of Biological Chemistry, Vol. 269, 20952–20957, 1994). Namely, into each well of a Fluoro Nunc plate (96C) white (No. 437842, manufactured by Nunc Co.), 180 µl of a MMP-3 solution (0.0125 unit/ml; No. YU-26003, manufactured by Kabushiki Kaisha Yagai Chuo Kenkyusho, purity: at least 99%), 10 µl of a test materials (the compound of the present invention) dissolved in DMSO and 10 µl of a peptide substrate enzyme (final concentration: 10 µM) were added and maintained at 37° C. for 2 hours in a dark place. Dilution of the enzyme was carried out by using 50 mM of Tris-HCl (pH 7.5) comprising 0.1M of NaCl, 10 mM of CaCl$_2$, 0.05% Brij 35 and 0.02% of NaN$_3$.

For the MMP-3 enzymatic activity, the amount of the decomposition product after the reaction was quantitatively analyzed as the change in the relative fluorescence intensity at a fluorescence wavelength of 400 nm with an excitation wavelength of 326 nm (using a variable fluorescence plate reader (variable wavelength type) Spectron FL-2575, manufactured by Towa Kagaku K. K.), and the inhibition activity of the test materials against the enzymatic activity was calculated by comparing the relative fluorescence intensities of the inhibitor added group and the non-added group after completion of the reaction. The test results are shown in Table 34.

TABLE 34

| Inhibition activity against MMP-3 IC$_{50}$ (µmol/l) | | |
|---|---|---|
| Compound No. 157 | Compound No. 107 | Compound No. 164 |
| IC$_{50}$ 24.2 | 22.3 | 17.8 |

TEST EXAMPLE 2

Measurement of the Enzyme Inhibition Activity Against MMP-7 (Matrilysin)

The inhibition activity against human MMP-7 was measured by the same method as the method for MMP-3, by using a MMP-7 solution (0.025 unit/ml; No. YU-31001, manufactured by Kabushiki Kaisha Yagai Chuo Kenkyusho, purity: at least 99.9%) and a fluorescent peptide substrate MOCAc—Arg-Pro-Lys-Pro-Tyr—Ala-Nva-Trp-Met-Lys (Dnp) -NH$_2$ [NFF-2, No. 3167-v, manufactured by Peptide Institute, Inc.]. The enzymatic reaction was carried out at 37° C. for 2.5 hours in a dark place, and the relative fluorescence intensity was measured at a fluorescence wavelength of 400 nm with an excitation wavelength of 327 nm. The test results are shown in Table 35.

TABLE 35

| Inhibition activity against MMP-7 IC$_{50}$ (µmol/l) | | | |
|---|---|---|---|
| Compound No. 37 | Compound No. 157 | Compound No. 107 | Compound No. 164 |
| IC$_{50}$ 24.5 | 16.5 | 18.7 | 12.0 |

TEST EXAMPLE 3

Measurement of the Inhibition Activity of the Compound of the Formula (I) Against Human MMP-9 (Gelatinase B)

(1) Preparation of Human MMP-9

Human MMP-9 (gelatinase B) was purified by the following method from a culture supernatant of HT1080 cells (human fibrosarcoma).

(1-1) Preparation of a Crude Enzyme Solution 2.5×10$^6$ HT1080 cells (ATCC CCL-121, purchased from Dainippon Seiyaku) were inoculated to a tissue culture dish (Code No. 3020-100, manufactured by Iwaki Glass Co., Ltd.) having a diameter of 10 cm and containing 10 ml of Dulbecco's Modified Eagle Medium (DME, No. D-5648, manufactured by Sigma Co.) containing 10% fetal bovine serum (FBS: REHATUIN™, Code No. 1020-90, manufactured by Intergen Co.) and cultured for 72 hours at 37° C. in an atmosphere comprising 5% of CO$_2$ and 95% of air (Carbon Dioxide Incubator LNA-122D Model, manufactured by Tabai Co.). Then, the medium was changed to 10 ml of a DME culture medium containing no FBS, and phorbol 12-myristate 13-acetate (PMA, code No. 163-114851, manufactured by Wako Pure Chemical Industries, Ltd.) was added so that the final concentration became 10 ng/ml. Under the same conditions, the culturing was carried out for further 20 hours, whereupon the culture supernatant was collected and subjected to cool centrifugation at 4° C. for 5 minutes (cool centrifugal separator, manufactured by Hitachi) to remove cell fragments.

(1-2) Column Separation

The pH of a conditioned medium (50 ml) containing MMP-9, thus prepared, was adjusted to 8.0 with 0.2N NaOH. Then, purification was sequentially carried out by the following column operation by a partially improved method by Tanzawa et al (Journal of Antibiotics, Vol. 45, 1733, 1992). Namely, the above-mentioned conditioned medium was passed through DEAE-Sephacel (manufactured by Pharmacia, gel volume: about 35 ml) preliminarily equilibrated with 50 mM Tris-HCl, pH 8.0 (A buffer), and a non-adsorption fraction was collected. Then, it was added to Dye Matrix Gel Green A (manufactured by Amicon Co., gel volume: about 6 ml) preliminarily equilibrated with 50 mM Tris-HCl, pH 7.5/10 MM CaCl$_2$/0.05% Brij 35/0.02% NaN$_3$ (B buffer) and thoroughly washed with the same buffer, whereupon the adsorbed enzyme was eluted with a 1M NaCl-containing B buffer. About 7.5 ml of the eluted fraction was diluted twice with the B buffer and added to Gelatin-Sepharose 4B (manufactured by Pharmacia, gel volume: about 6 ml) preliminarily equilibrated with a 0.5 M NaCl-containing B buffer. It was thoroughly washed with a 0.5M NaCl-containing B buffer, and eluted with the B buffer containing 10% of dimethylsulfoxide (DMSO) and 0.5 M of NaCl. 5.5 ml of the eluted fraction was dialyzed against a 0.1 M NaCl-containing B buffer to obtain 5.2 ml of a purified enzyme solution. The purified MMP-9 standard product was confirmed to have a single band of 92 kDa by a protein staining by SDS electrophoresis, and further, it was confirmed to have an adequate gelatin decomposing activity by gelatinzymography (carried out in accordance with a method by Howard E. W. et al; Journal Biological Chemistry, Vol. 266, 13064–13069, 1991) and to have an adequate substrate decomposing activity by the after-mentioned measurement employing a fluorescent peptide substrate specific to MMP.

(2) Measurement of the Inhibitory Activity Against Human MMP-9 (Gelatinase B)

The inhibition activity against human MMP-9 was measured by the following method in accordance with the method by C. G. Knight et al (FEBS Letters, Vol, 296, 263–266, 1992) employing a fluorescent peptide substrate (7-methoxycoumarin-4-yl)Acetyl-Pro-Leu-Gly-Leu-(3-[2, 4-dinitrophenyl]—Ala—Arg-NH$_2$, Code 3163-VC, manufactured by Peptide Institute, Inc.

Further, as the case requires, commercially available human MMP-9 purified enzyme (No. YU-18003, manufactured by Kabushiki Kaisha Yagai Chuo Kenkyusho; used in a final concentration of from 0.0125 to 0.025 unit/ml, No. CC079, manufactured by Chemicon International, Inc.; used in a final concentration of 0.2 μg/ml) was used for the tests.

Into a micro-centrifuging tube having a capacity of 1.5 ml, 380 μl of the MMP-9 solution (in the case of commercially available purified enzyme, it was used in a final concentration of from 0.0125 to 0.025 unit/ml or 0.2 μg/ml), 10 μl of compound No. 2, 8, 9, 10–30, 32–46, 48–57, 60–61, 67, 70–74, 76–79, 82–88, 90–112, 115, 117, 118–120, 122–132, 135–138, 140–142, 144–148, 152–153, 155–157, 159–170, 172, 174, 177–179, 181–182, 184, 186, 188–189, 191–197, 199 and 202 and Intermediate No. 1-3, 5–7, 10–12, 16, 19–21, 24, 25, 47, 49–52, 54, 55, 57, 59 and 61–64) dissolved in DMSO, and 10 μl of 400 μM fluorescent peptide substrate dissolved in DMSO (final concentration: 10 μM) were added and maintained at 37° C. for 3 hours in a dark place. MMP-9 was present in the form of an inert precursor, and accordingly, 10 μl of a 38 mM 4-aminophenylmercuric acetate (APMA, Code No. A0395, manufactured by Tokyo Kaseil) (final concentration: 1 mM) was preliminarily added to 370 μl of the enzyme solution, and the mixture was left to stand at 4° C. for 20 hours to convert it to an active form, whereupon it was supplied to the test for the enzyme inhibition activity. Further, dilution of the enzyme was carried out by means of 50 mM Tris-HCl (pH 7.5) comprising 0.1 M of NaCl, 10 mM of $CaCl_2$, 0.05% of Brij 35 and 0.02% $NaN_3$.

For the MMP-9 activity, the amount of the decomposition product after the reaction was quantitatively analyzed as a change in the relative fluorescence intensity at a fluorescent wavelength of 393 nm with an excitation wavelength of 328 nm (using F4000 model fluorescent spectrophotometer, manufactured by Hitachi, Ltd., and the inhibition activity by the test materials against the enzyme activity was calculated by comparing the relative fluorescence intensities of the inhibitor-added group and the non-added group after completion of the reaction.

Further, when the enzymatic reaction was carried out by means of a microplate (Fluoro Nunc Plate (96C) White (No. 437842, manufactured by Nunc Co.)) a variable fluorescence plate reader (variable wavelength type) (Spectron FL-2575 (manufactured by Towa Kagaku K. K.) was used, and the measurement was carried out at a fluorescence wavelength of 400 nm with an excitation wavelength of 327 nm.

The measurement of the MMP-9 inhibition activity in Test Example 3 was carried out once or twice for each, and the results are shown in Tables 36 to 40.

TABLE 36

MMP-9 inhibition activities of compounds of the formula (I)

| Comp. No. | $IC_{50}$ (μmol/l) 1st | 2nd | Average | Comp. No. | $IC_{50}$ (μmol/l) 1st | 2nd | Average |
|---|---|---|---|---|---|---|---|
| 2 | 45.1 | 24.7 | 34.9 | 32 | 26.7 | 24.0 | 25.4 |
| 8 | 36.7 | 30.1 | 33.4 | 33 | 30.6 | 31.9 | 31.8 |
| 9 | 42.2 | 43.9 | 43.1 | 34 | 30.2 | 26.9 | 28.6 |
| 10 | 42.6 | 54.2 | 48.4 | 35 | 14.6 | 22.1 | 18.4 |
| 11 | 31.9 | 33.7 | 32.8 | 36 | 19.7 | 24.3 | 22.0 |
| 12 | 32.9 | 24.5 | 28.7 | 37 | 4.5 | 7.0 | 5.8 |
| 13 | 20.1 | 16.1 | 18.1 | 38 | 13.7 | 19.1 | 16.4 |
| 14 | 47.4 | 42.2 | 44.8 | 39 | 16.1 | 29.2 | 22.7 |
| 15 | 46.8 | 52.7 | 49.8 | 40 | 13.5 | 28.7 | 21.1 |
| 16 | 49.8 | 43.9 | 46.8 | 41 | 15.1 | 13.7 | 14.4 |
| 17 | 43.8 | 28.8 | 36.3 | 42 | 41.4 | 40.7 | 41.4 |
| 18 | 18.3 | 26.6 | 22.5 | 43 | 24.7 | 20.2 | 22.5 |
| 19 | 10.1 | 13.2 | 11.7 | 44 | 19.6 | 26.8 | 23.2 |
| 20 | 24.1 | 32.0 | 28.1 | 45 | 33.8 | 26.3 | 30.1 |
| 21 | 11.7 | 18.1 | 14.9 | 46 | 36.2 | 34.8 | 35.5 |
| 22 | 17.9 | 17.4 | 17.7 | 48 | 20.6 | 18.2 | 19.4 |
| 23 | 42.5 | 54.8 | 48.7 | 49 | 15.6 | 18.0 | 16.8 |
| 24 | 28.9 | 34.9 | 31.9 | 50 | 25.7 | 23.0 | 24.3 |
| 25 | 21.9 | 30.0 | 26.0 | 51 | 27.3 | 32.1 | 29.7 |
| 26 | 31.9 | 31.5 | 31.7 | 52 | 21.6 | 30.2 | 25.9 |
| 27 | 26.6 | 24.5 | 25.6 | 53 | 22.6 | 29.3 | 26.0 |
| 28 | 23.3 | 24.6 | 24.0 | 54 | 26.2 | 30.3 | 28.3 |
| 29 | 30.8 | 24.5 | 27.7 | 55 | 25.3 | 30.0 | 27.7 |
| 30 | 11.3 | 17.5 | 14.4 | 56 | 39.9 | 33.5 | 36.7 |

TABLE 37

MMP-9 inhibition activities of compounds of the formula (I)

| Comp. No. | $IC_{50}$ (μmol/l) 1st | 2nd | Average | Comp. No. | $IC_{50}$ (μmol/l) 1st | 2nd | Average |
|---|---|---|---|---|---|---|---|
| 57 | 38.7 | 35.1 | 36.6 | 94 | 4.2 | 7.0 | 5.6 |
| 60 | 48.5 | 45.4 | 47.0 | 95 | 26.7 | 27.0 | 26.9 |
| 61 | 39.7 | 42.2 | 40.9 | 96 | 24.5 | 21.3 | 22.9 |
| 67 | 56.9 | 43.1 | 50.0 | 97 | 45.7 | 35.3 | 40.5 |
| 70 | 42.1 | 57.1 | 49.6 | 98 | 8.8 | 7.8 | 8.3 |
| 71 | 42.9 | 37.4 | 40.2 | 99 | 20.5 | 30.0 | 25.3 |
| 72 | 40.8 | 41.5 | 41.2 | 100 | 38.7 | 26.0 | 32.4 |
| 73 | 44.6 | 47.9 | 46.3 | 101 | 37.8 | 18.5 | 28.2 |
| 74 | 49.6 | 49.4 | 49.5 | 102 | 18.2 | 14.0 | 16.1 |
| 76 | 34.0 | 33.8 | 33.9 | 103 | 8.9 | 10.7 | 9.8 |
| 77 | 41.4 | 35.2 | 38.3 | 104 | 21.1 | 17.5 | 19.3 |
| 78 | 44.1 | 36.0 | 40.1 | 105 | 14.2 | 17.0 | 15.6 |
| 79 | 39.0 | 36.6 | 37.8 | 106 | 11.7 | 8.4 | 10.1 |
| 82 | 52.9 | 19.0 | 36.0 | 107 | 8.0 | 7.4 | 7.7 |
| 83 | 66.2 | 14.2 | 36.0 | 108 | 15.0 | 35.0 | 25.0 |
| 84 | 43.4 | 14.2 | 28.8 | 109 | 20.8 | 26.9 | 23.9 |
| 85 | 52.8 | 41.1 | 47.0 | 110 | 35.2 | 29.3 | 32.3 |
| 86 | 41.8 | 41.5 | 41.7 | 111 | 45.5 | 26.8 | 36.2 |
| 87 | 20.5 | 25.3 | 22.9 | 112 | 38.2 | 30.9 | 34.6 |
| 88 | 37.7 | 57.5 | 47.6 | 115 | 31.8 | 26.5 | 29.2 |
| 90 | 18.7 | 37.4 | 28.0 | 117 | 30.0 | 39.3 | 34.7 |
| 91 | 20.0 | 35.7 | 27.9 | 118 | 32.3 | 35.1 | 33.7 |
| 92 | 15.4 | 20.6 | 18.0 | 119 | 28.0 | 23.4 | 25.7 |
| 93 | 48.3 | 44.8 | 46.6 | | | | |

TABLE 38

MMP-9 inhibition activities of compounds of the formula (I)

| Comp. No. | $IC_{50}$ (μmol/l) 1st | 2nd | Average | Comp. No. | $IC_{50}$ (μmol/l) 1st | 2nd | Average |
|---|---|---|---|---|---|---|---|
| 120 | 39.8 | 39.4 | 39.6 | 152 | 29.6 | 16.3 | 23.0 |
| 122 | 12.6 | 16.3 | 14.5 | 153 | 35.8 | 16.9 | 26.4 |
| 123 | 13.9 | 12.4 | 13.2 | 155 | 24.3 | 43.5 | 33.9 |
| 124 | 16.1 | 18.6 | 17.4 | 156 | 38.3 | 41.8 | 40.1 |
| 125 | 10.1 | 15.8 | 13.0 | 157 | 7.4 | 5.5 | 6.5 |
| 126 | 29.4 | 21.8 | 25.6 | 159 | 7.9 | — | 7.9 |
| 127 | 1.4 | 2.8 | 2.1 | 160 | 9.4 | — | 9.4 |

TABLE 38-continued

MMP-9 inhibition activities of compounds of the formula (I)

| Comp. No. | IC$_{50}$ ($\mu$mol/l) 1st | 2nd | Average | Comp. No. | IC$_{50}$ ($\mu$mol/l) 1st | 2nd | Average |
|---|---|---|---|---|---|---|---|
| 128 | 19.2 | 10.3 | 13.0 | 161 | 6.0 | — | 6.0 |
| 129 | 11.8 | 6.7 | 9.3 | 162 | 6.3 | — | 6.3 |
| 130 | 7.7 | 8.4 | 8.1 | 163 | 9.2 | — | 9.2 |
| 131 | 2.0 | 3.0 | 2.5 | 164 | 5.4 | 5.9 | 5.7 |
| 132 | 1.2 | 2.4 | 1.8 | 165 | 3.2 | — | 3.2 |
| 135 | 28.2 | 20.4 | 24.3 | 166 | 7.8 | — | 7.8 |
| 136 | 21.3 | 29.2 | 25.3 | 167 | 14.0 | — | 14.0 |
| 137 | 17.7 | 37.1 | 27.4 | 168 | 7.1 | 7.3 | 7.2 |
| 138 | 22.3 | 15.7 | 19.0 | 169 | 6.0 | 9.6 | 7.8 |
| 140 | 22.3 | 21.9 | 22.6 | 170 | 5.6 | — | 5.6 |
| 141 | 19.9 | 18.1 | 19.0 | 172 | 0.82 | 1.1 | 0.96 |
| 142 | 20.4 | 22.4 | 21.4 | 174 | 9.0 | — | 9.0 |
| 144 | 4.8 | 14.9 | 9.9 | 177 | 10.7 | 6.1 | 8.4 |
| 145 | 1.7 | 4.1 | 2.9 | 178 | 11.8 | 12.5 | 12.2 |
| 146 | 18.4 | 29.4 | 23.9 | 179 | 8.3 | — | 8.3 |
| 147 | 35.0 | 39.9 | 37.5 | 181 | 11.6 | — | 11.6 |
| 148 | 33.5 | 21.7 | 27.6 | | | | |
| 150 | 14.8 | 11.4 | 13.1 | | | | |

TABLE 39

MMP-9 inhibition activities of compounds of the formula (I)

| Comp. No. | IC$_{50}$ ($\mu$mol/l) 1st | 2nd | Average | Comp. No. | IC$_{50}$ ($\mu$mol/l) 1st | 2nd | Average |
|---|---|---|---|---|---|---|---|
| 182 | 7.0 | 5.6 | 6.4 | 193 | 10.5 | — | 10.5 |
| 184 | 20.0 | 10.6 | 15.3 | 194 | 4.9 | 8.4 | 6.7 |
| 186 | 12.3 | — | 12.3 | 195 | 11.6 | — | 11.6 |
| 188 | 6.2 | — | 6.2 | 196 | 11.2 | — | 11.2 |
| 189 | 11.1 | — | 11.1 | 197 | 10.3 | 10.9 | 10.6 |
| 191 | 7.4 | 4.4 | 5.9 | 199 | 5.7 | 6.2 | 6.0 |
| 192 | 8.1 | 13.6 | 10.9 | 202 | 6.3 | — | 6.3 |

TABLE 40

MMP-9 inhibition activities of compounds of the formula (IV)

| Int. No. | IC$_{50}$ ($\mu$mol/l) 1st | 2nd | Average | Int. No. | IC$_{50}$ ($\mu$mol/l) 1st | 2nd | Average |
|---|---|---|---|---|---|---|---|
| 1 | 28.6 | 42.9 | 35.6 | 25 | 38.9 | 35.3 | 37.1 |
| 2 | 31.4 | 59.9 | 45.7 | 47 | 24.4 | 26.5 | 25.5 |
| 3 | 21.3 | 37.3 | 29.3 | 49 | 29.5 | 29.0 | 29.3 |
| 5 | 26.9 | — | 26.9 | 50 | 33.9 | 25.3 | 29.6 |
| 6 | 33.0 | — | 33.0 | 51 | 31.6 | 26.0 | 28.8 |
| 7 | 38.0 | — | 38.0 | 52 | 61.5 | 50.4 | 56.0 |
| 10 | 26.9 | 46.6 | 36.8 | 54 | 38.7 | 33.9 | 36.3 |
| 11 | 17.6 | 15.9 | 16.8 | 55 | 32.5 | 25.5 | 29.0 |
| 12 | 25.3 | 24.5 | 24.9 | 57 | 49.4 | 37.5 | 43.5 |
| 16 | 24.5 | 18.9 | 21.7 | 59 | 11.4 | — | 11.4 |
| 19 | 29.9 | 35.6 | 32.8 | 61 | 8.2 | — | 8.2 |
| 20 | 38.9 | 49.6 | 44.3 | 62 | 4.5 | — | 4.5 |
| 21 | 31.6 | 54.4 | 43.0 | 63 | 4.3 | — | 4.3 |
| 24 | 43.1 | 31.8 | 37.4 | 64 | 4.4 | — | 4.4 |

TEST EXAMPLE 4

Measurement of the Inhibitory Action Against Capillary-like Tube Formation of Vascular Endothelical Cells (1) Test Method Three Dimensional Culture of Vascular Endothelical Cells Employing Collagen Gel With reference to the method disclosed in a literature (Hayashi, J. N. et al, Virchows arch. (B), Vol. 60,245–252, 1991, Lee, D. Y. et al, Life Science, Vol. 60, 127–134, 1997), evaluation was carried out by the following method.

1) Preparation of Underlayer Collagen Gel

7 Parts by volume of type I-a collagen (manufactured by Nitta Gelatin K. K.) and 2 parts by volume of Dulbecco's Modified Eagle Medium (concentration: 5 times, containing no NaHCO$_3$; No. D-5648, manufactured by Sigma Co.) were thoroughly mixed under cooling with ice, and then one part by volume of a collagen gel-reconstructing buffer solution (2.2% NaHCO$_3$/0.2M HEPES/0.05N NaOH) was added thereto. To withdraw bubbles, centrifugal separation and supersonic treatment were carried out, and then 400 $\mu$l of the gel was introduced into 24 well multi-well plate (Code 3047, manufactured by Falcon Co.) and incubated at 37° C. for about 10 minutes for gelation.

2) Three Dimensional Culture of CPAE Cells

On the gelled collagen, CPAE cells (bovine pulmonary-derived vascular endothelical cells; ATCC CCL209, purchased from Dainippon Seiyaku K. K.) was inoculated in a concentration of 4×10$^4$ cells/400 $\mu$l/well (Day 0). Thereafter the cells were cultured overnight at 37° C. in a 5% CO$_2$ incubator. Next day (Day 1), after confirming that the cells were normally proliferating, the culture solution was removed by aspiration, and a fresh collagen gel (prepared in the same manner as the above layer) was overlaid in an amount of 200 $\mu$l/well and gelled.

3) Evaluation of the Effect of the Test Materials

On the gel, the test materials dissolved in 10% fetal bovine serum-containing Dulbecco's Modified Eagle Medium (No. D-5648, manufactured by Sigma Co.) (prepared to have a concentration four times the final concentration) was added in an amount of 200 $\mu$l, and culturing was continued under the same conditions. Upon expiration of three days from stratification (Day 4), capillary-like tube formation was observed by a microscope, and an optional field of view was photographed with 100 magnifications, whereupon the number of capillary-like structures formed (the number of networks) were visually counted with reference to the method disclosed in a literature by Yeong, H. et al (Cancer Research, Vol. 56, 2428–2433, 1996). For each test sample, 2 well treatment was carried out, and a total of five fields of view were photographed for evaluation.

(2) Test Results

TABLE 41

Inhibition ratio against capillary-like tube formation of CPAE bovine vascular endothelical cells (n = 5)

| Treating concentration | Solvent control | Compound No. 107 | | | | Compound No. 164 | | | |
|---|---|---|---|---|---|---|---|---|---|
| (µM) | 0 | 0.1 | 1 | 10 | 100 | 0.1 | 1 | 10 | 100 |
| Number of networks Average ± SD | 30.8 ± 2.2 | 20.0 ± 5.7 | 18.2 ± 1.6 | 11.8 ± 5.0 | 2.0 ± 2.8 | 23.6 ± 3.2 | 17.2 ± 4.1 | 17.2 ± 6.0 | 10.4 ± 5.7 |
| Inhibition ratio (%) | — | 35* | 41* | 62* | 93* | 23 | 44* | 44* | 66* | p < 0.01 against vehicle control group (Dunnett multiple comparison test)

TEST EXAMPLE 5

Measurement of the Inhibition Effects of Compound No. 107 and Compound No. 164 Against Tumor Growth of Meth A/AD

(1) Preparation of Meth A/AD Strain

Meth A mouse fibrosarcoma cells intraperitoneally subcultured in mouse (supplied from Sasaki Institute) were cultured at 39° C. for 10 days in 5% $CO_2$ (using 10% fetal bovine serum-containing RPMI culture medium (manufactured by Flow Laboratories)) and then inoculated subcutaneously to BALB/c mouse. The tumor grown for 30 days, was taken out and passed through a metal mesh to obtain single cells, which were again returned and continuously cultured in vitro (37° C.). When subculture was repeated for about 1 month, Meth A/AD cell strain was obtained which showed adhesion to the culture dish and which constantly proliferated. The Meth A/AD strain showed substantially the same doubling time and cell proliferation as the parental cells in vitro, but the subcutaneous or growth rate in intradermal region in vivo was at a level of from ½ to ⅓ of the parental cell. Further, the Meth A/AD strain showed no proliferation in the peritoneal cavity of mouse, which is observed in the parental cells. On the other hand, the Meth A/AD strain always produces and secretes MMP-2 in the supernatant in in vitro culture, but when TNF-α (50 ng/ml) was added in the culture solution, it produced MMP-9 remarkably.

(2) Inhibition Effects Against in Vivo Tumor Growth of the Meth A/AD Strain With reference to the method by Keneda et al (Cancer Research, Vol. 58, 290–295, 1998), the inhibitory effect on tumor growth were evaluated. Namely, $1 \times 10^6$ Meth A/AD cells cultured in vitro (suspended in 0.05 ml of a Hanks equilibrium salt solution) were intradermaly transplanted to the dosal skin of a male BALB/c AnNCrj mouse of 5 weeks old (purchased from Charles River Japan, Inc.) (Day 0). The test materials was intraperitoneally administered (administered in a volume of 10 ml/kg) upon expiration of 2 hours from the cell implantation and once a day on Day 1 to 4 and Day 7 to 11 (total of 10 times). Compound No. 107 was suspended in a 1% Tween 80 physiological sodium chloride aqueous solution, and Compound No. 164 was dissolved in 100 mM Tris-HCl (pH 8.5)/150 mM NaCl, for administration. To the vehicle control group, the respective solvents containing no test materials were administered in the same manner. The measurement of the body weight and the observation of the general findings were carried out everyday up to Day 22 or 24, and the tumor diameters (the long diameter and the short diameter) were measured by a slide gauge every one day, and the difference in the tumor volume between the vehicle control group and the drug-treated group was evaluated. The tumor volume was calculated in accordance with the calculation formula of [(long diameter)×(short diameter)$^2$×½].

(3) Results

By the intraperitoneally administration in a total of 10 times of Compound No. 107 (100 mg/kg) and Compound No. 164 (30 mg/kg), the tumor growth of Meth A/AD was significantly inhibited, and the inhibition ratios were 63.5% and 49.8%, respectively. During the test period, no distinct toxicity or inhibition against the increase of the body weight derived from the drug administered group, was observed by the observation of the general findings.

TABLE 42

Inhibition effects of Compound 107 against the tumor growth of Meth A/AD (Intraperitoneal administration)

| Administrated group | Dose (mg/kg × 11 times) | Number of test animals | Tumor volume (Day 22) Average ± standard deviation (mm$^3$) | Tumor growth inhibition ratio (%) |
|---|---|---|---|---|
| Vehicle control | — | 6 | 1058 ± 556 | — |
| Compound No. 107 | 100 | 5 | 386 ± 275* | 63.5* |

*p < 0.05 (t-test)

TABLE 43

Inhibition effects of Compound 107 against the tumor growth of Meth A/AD (Intraperitoneal administration)

| Administrated group | Dose (mg/kg × 11 times) | Number of test animals | Tumor volume (Day 24) Average ± standard deviation (mm$^3$) | Tumor growth inhibition ratio (%) |
|---|---|---|---|---|
| Vehicle control | — | 21 | 2045 ± 987 | — |
| Compound No. 164 | 30 | 6 | 1027 ± 907* | 49.8* |

*p < 0.05 (t-test)

TEST EXAMPLE 6

Measurement of the Inhibition Effects of Compound No. 37 and Compound No. 157 Against Experimental Lung Metastatis of Colon 26/AD

(1) Preparation of Colon 26/AD Cell Strain

Colon 26 mouse colon cancer cells (obtained from Cancer Chemotherapy Center Foundation for Cancer Research) were transplanted subcutaneously to BALB/c mouse, 10 days later, the grown tumor was taken out. It was hashed in a Hanks equilibrium salt solution and passed through a metal mesh to obtain single cells, which were cultured in vitro (37° C., 5% $CO_2$) (using 10% fetal bovine serum-containing Dulbecco's Modified Eagle Medium (D-5648, manufactured by Sigma Co.)). After subculture for several times, Colon 26/AD cell strain was obtained which showed adhesion to the culture dish and which proliferated constantly. The same cell strain always produced and secreted MMP-2 in the supernatant of the in vitro culture, but when cultured by an addition of TNF-α (50 ng/ml) in the culture solution, it produced MMP-9 remarkably.

(2) Inhibition Effects Against Experimental Lung Metastatis of Column 26/AD

With reference to the method by Tsuruo et al (Japanese Journal of Cancer Research (Gann), Vol. 75, 193–198, 1984), the inhibition effects against experimental lung metastasis were evaluated. Namely, $3 \times 10^4$ Colon 26/AD cells (suspended in 0.2 ml of Minimum Essential Medium (manufactured by Nissui Seiyaku K. K.)) cultured in vitro were transplanted through the tail vein of a male BALB/c AnNCrj mouse (purchased from Charles River Japan, Inc.) of 6 weeks old (Day 0). In the case of Compound No. 37, it was suspended in a 1% Tween 80/physiological sodium chloride aqueous solution and intraperitoneally administered (administered in a volume of 10 ml/kg) immediately (within 5 minutes) before transplantation of the cells, 2 hours later and once per day on Day 1–4 and Day 7–11 (a total of 11 times). Further, in the case of Compound No. 157, it was dissolved in 100 mM Tris-HCl (pH 8.5)/150 mM NaCl and forcibly orally administered (administered in a volume of 10 ml/kg) by means of a metal sonde 30 minutes before transplantation of the cells, in the morning and evening of Day 1 and once per day on Day 2–4, Day 7–11 and Day 14 (a total of 12 times). To the vehicle control group, the respective solvents containing no test materials, were administered in the same manner. On Day 14 or Day 15, the lung of each mouse was taken out, and the weight was measured, and the metastatis inhibition rate was calculated in accordance with the following formula.

$$\text{Inhibition ratio (\%)} = 1 - \left(\frac{A-B}{C-B}\right) \times 100$$

where
A is the weight of lung of the treated group
B is the average weight of lung of the normal group
C is the average weight of lung of the solvent control group.

(3) Results

Compound No. 37 (30 mg/kg) in the intraperitoneal administration in a total of 11 times, and Compound No. 157 (10 mg/kg) in oral administration in a total of 12 times, inhibited the experimental metastatis of Colon 26/AD to lung significantly, and their inhibition ratios were 40.2% and 59.5%, respectively. During the test period, no distinct toxicity or inhibition against an increase of the body weight derived from the drug-administered group was observed from the observation of general findings.

TABLE 44

Inhibition effects of Compound No. 37 against experimental lung metastatis of Colon 26/AD

| Administrated group | Dose (mg/kg × 11 times) | Number of test animals | Weight of lung (g) (Day 14) | Lung weight increase (g) against normal mouse | Metastatis inhibition ratio (%) |
|---|---|---|---|---|---|
| Normal mouse | — | 9 | 0.213 ± 0.02 | — | — |
| Vehicle control | — | 8 | 0.402 ± 0.07 | 0.189 ± 0.07 | — |
| Compound No. 37 | 30 | 5 | 0.326 ± 0.06 | 0.113 ± 0.06* | 40.2%* |

*p < 0.05 (t-test)

TABLE 45

Inhibition effects of Compound No. 157 against experimental lung metastatis of Colon 26/AD

| Administrated group | Dose (mg/kg × 11 times) | Number of test animals | Weight of lung (g) (Day 15) | Lung weight increase (g) against normal mouse | Metastatis inhibition ratio (%) |
|---|---|---|---|---|---|
| Normal mouse | — | 12 | 0.181 ± 0.35 | — | — |
| Vehicle control | — | 18 | 0.364 ± 0.11 | 0.183 ± 0.11 | — |
| Compound No. 157 | 10 | 6 | 0.257 ± 0.08 | 0.070 ± 0.08* | 59.5%* |

*p < 0.05 (t-test)

TEST EXAMPLE 7

Inhibition Effects of Compound No. 164 Against Mouse Arthritis Model Induced by a Single Immunization with Collagen

(1) Preparation of Sensitized Antigen for Inducing Arthritis

With reference to the method by Kato, F. et al (Annals of the Rheumatic Diseases, Vol. 55, 535–539, 1996), a bovine type II collagen (K-41, manufactured by collagen Gijutsu Kenkyukai) solution (3 mg/ml) dissolved in 0.05N acetic acid and Freund's complete adjuvant (Freund, Adjuvant Complete; No. F5506, manufactured by Sigma Co.) were mixed in equal amounts and subjected to ultrasonic treatment (under cooling with ice, 20 seconds×3 times) to obtain a uniform emulsion.

(2) Antigen Sensitization of Mouse and Drug Administration 0.1 ml (150 μg) of the antigen prepared as described above, was administered to the tail head skin of a female DBA/1JNCrj mouse of 5 weeks old (purchased from Charles River Japan, Inc.) (Day 0). After 2 weeks from sensitization (Day 14), Compound No. 164 (50 mg/kg) suspended in a 1% Tween 80/physiological sodium chloride aqueous solution was intraperitoneally administered (administered in a volume of 10 ml/kg) once a day continuously for 5 weeks. To the vehicle control group, the 1% Tween 80/physiological sodium chloride aqueous solution was administered in the same manner.

(3) Medicinal Effect

Sideration of arthritis was observed once a week from Day 1 in accordance with the following evaluation standards disclosed in a literature of Kato, F. et al (Annals of the Rheumatic Diseases, Vol. 55, 535–539, 1996) with respect to Knuckle joints of the respective four limbs. When swelling was observed with respect to at least one limb among four limbs, such was judged to be sideration.

(4) Results

By the intraperitoneal administration of 50 mg/kg of Compound No. 164 everyday, sideration of arthritis was significantly delayed as compared with the control group (p<0.01; Wilcoxon ranking test). During the test period, no distinct toxicity or inhibition against the body weight increase derived from the drug-administered group was observed by observation of general findings.

TABLE 46

Influence of Compound No. 164 against mouse arthritis model induced by a single immunization with collagen (intraperitoneal administration)

| Administration group | Dose (mg/ kg) | Number of test animals | Sideration ratio of arthritis (number of diseased animals/number of tested animals) | | | | | |
|---|---|---|---|---|---|---|---|---|
| | | | Day 14* | Day 21 | Day 28 | Day 35 | Day 42 | Day 49 |
| Vehicle control | — | 8 | 0/8 | 2/8 | 7/8 | 8/8 | 8/8 | 8/8 |
| Compound No. 164 | 50 | 8 | 0/8 | 0/8 | 2/8 | 6/8 | 7/8 | 7/8 |

*At the initial of administration of drug

What is claimed is:
1. A process for producing a nitroetheneamine derivative represented by the formula (I'-1)

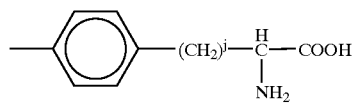

(I'-1)

wherein $R^{1'}$ is a hydrogen atom, an alkyl group which may be substituted, an alkenyl group which may be substituted, an alkynyl group which may be substituted, a cycloalkyl group which may be substituted, a cycloalkenyl group which may be substituted or a cyano group;

each of $R^{2'}$ and $R^{3'}$ which are independent of each other, is a hydrogen atom, an alkyl group which may be substituted (provided that a heterocyclic methyl group which may be substituted is excluded), a cycloalkyl group which may be substituted, a cycloaklenyl group which may be substituted, a hetercyclic group which may be substituted or a A'—$R^{7'}$ group (wherein A' is S, SO, $SO_3$, CO or $CO_2$, and $R^{7'}$ is a hydrogen atom, an alkyl group which may be substituted, an alkenyl group which may be substituted, an alkynyl group which may be substituted, a cycloalkyl group which may be substituted, a cycloaklenyl group which may be substituted, an aryl group which may be substituted or a heterocyclic group which may be substituted); or $R^{2'}$ or or $R^{3'}$ may form, together with the N atom, a N—$CR^{8'}R^{9'}$ group (wherein each of $R^{8'}$ and $R^{9'}$ which are independent of each other, is a hydrogen atom, an alkyl group which may be substituted, an aryl group which may be substituted, a heterocyclic group which may be substituted or an alkoxy group which may be substituted);

$R^{4'}$ is an alkyl group which may be substituted, an alkenyl group which may be substituted, an alkoxyphenyl group, a haloalkyloxyphenyl group, which may be substituted, a cycloalkenyl group which may be substituted, an alkoxy group which may be substituted, a—A'$R^{7'}$ group (wherein A' and $R^{7'}$ are as defined above) or an amino group which may be substituted;

$R^{6'}$ is a hydrogen atom, a nitro group, a cyano group or a A'—$R^{7'}$ group (wherein A' and $R^{7'}$ are as defined above) or an alkyl group which may be substituted;

at least two selected from $R^{1'}$, $R^{2'}$, $R^{3'}$ and $R^{4'}$ may together form a ring containing or not containing a hetero atom in addition to the nitrogen atom;

provided that
(1) a case wherein $R^{1'}$ or $R^{4'}$ is an alkyl group substituted by a hetero-ring which may be substituted,
(2) a case where $R^{1'}$, $R^{3'}$ and $R^{6'}$ are all hydrogen atoms, $R^{2'}$ is a hydrogen atom, an alkyl group which may be substituted or an aryl group which may be substituted, and $R^{4'}$ is

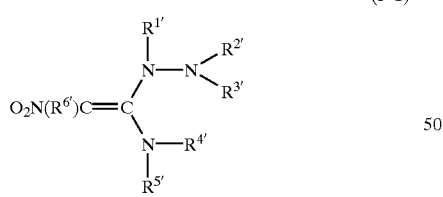

(wherein j is an integer of from 1 to 6), and
(3) a case wherein $R^{1'}$ is a hydrogen atom;
each of $R^{2'}$ and $R^{3'}$ which are independent of each other, is a hydrogen atom, and alkyl group which may be substituted or a phenyl group which may be substituted, $R^{4'}$ is an alkyl which may be substituted, a phenyl group which may be substituted, an A'—$R^{7'}$ group (wherein A' and $R^{7'}$ are as defined above) or an amino group which may be substituted; and
$R^{6'}$ is a hydrogen atom, are excluded; or
its stereoisomers, its tautomer or a salt thereof which comprises:
(a) a first step of reacting a compound represented by the formula (XXIV-1)

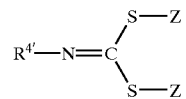

wherein $R^{4'}$ is as defined above, Z is an alkyl group or an arylalkyl group, with a compound by the formula (XVII-1) $R^{6'}$—$CH_2NO_2$ (wherein $R^{6'}$ is as defined above) to obtain a compound represented by the formula (XXV-1):

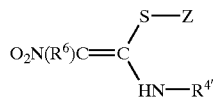

wherein $R^{4'}$, $R^{6'}$ and Z are as defined above, and
(2) a second step of reacting the compound of the above formula (XXV-1) obtained in the first step with a compound represented by the formula (V-1)

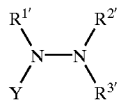

(wherein Y is a hydrogen atom or an alkali metal element, and $R^{1'}$, $R^{2'}$ and $R^{4'}$ are as defined above) to obtain a nitroetheneamine derivative of the above formula (I'-1).

2. A process for producing a nitroetheneamine derivative according to claim 1, wherein $R^{1'}$ is a hydrogen atom;

$R^{2'}$ is a hydrogen atom, a heterocyclic group which may be substituted or a —A"—$R^{7"}$ group (wherein A" is CO, $CO_2$ or $SO_2$, and $R^{7"}$ is an alkyl group which may be substituted or an aryl group which may be substituted);

$R^{3'}$ is a hydrogen atom, an alkyl group which may be substituted (provided that a heterocyclic methyl group which may be substituted, is excluded), a heterocyclic group which may be substituted or a —A"—$R^{7'}$ group (wherein A" and $R^{7"}$ are as defined above); or $R^{2'}$ and $R^{3'}$ may together form, a $N=C^{R8"R9"}$ group (wherein each of $R^{8"}$ and $R^{9"}$ which are independent of each other, is a hydrogen atom, an alkyl group which may be substituted, an aryl group which may be substituted, a heterocyclic group which may be substituted or an alkoxy group which may be substituted);

$R^{4'}$ is an alkyl group which may be substituted (provided that a heterocyclic alkyl group which may be substituted, is excluded), an alkoxyphenyl group, a haloalkyloxyphenyl group, a cycloalkyl group which may be substituted, an alkylsulfonyl group which may be substituted, an alkenylsulfonyl group which may be substituted, an alkynylsulfonyl group which may be substituted, a cycloalkylsufonyl group which may be substituted, a cycloalkenylsulfonyl group which may be substituted, an arylsulfonyl group which may be substituted, a sulfonyl group substituted by a hetero ring which may be substituted or an amino group which may be substituted;

$R^{6'}$ is a hydrogen atom or an alkyl group;

and further $R^{2'}$ and $R^{3'}$ may together form a ring containing or not containing a hetero atom in addition to the nitrogen atom;

provided that
(1) a case where R", $R^{2'}$, $R^{3'}$, and R''' are hydrogen atoms;

$R^{3'}$ is a hydrogen atom or an alkyl group which may be substituted; and $R^{4'}$ is an alkyl group which may be substituted, an alkoxyphenyl group which may be substituted, a haloalkyloxyphenyl group, which may be substituted, an alkylsulfonyl group which may be substituted, an alkenylsulfonyl group which may be substituted, an alkynylsulfonyl group which may be substituted, a cycloalkylsulfonyl group which may be substituted, a cycloalkenylsulfonyl group which may be substituted, an arylsulfonyl group which may be substituted or a sulfonyl group substituted by a hetero ring which may be substituted, and (2) a case where R", $R^{3'}$, and $R^{6'}$ are hydrogen atoms, R''' is a heterocyclic group (provided that a heterocyclic group substituted by at least one halogen atom, is excluded), and $R^{4'}$ is an alkyl group which may be substituted, are excluded; or its stereoisomer, its tautomer or a salt thereof.

3. A process for producing a nitroetheneamine derivative according to claim 2, wherein R" is a hydrogen atom;

$R^{2'}$ is a heterocyclic group which may be substituted or a —A"—R''' group (wherein A" is CO, $CO_2$ or $SO_2$, and $R^{7"}$ is an alkyl group which may be substituted or an aryl group which may be substituted);

$R^{3'}$ is a hydrogen atom, an alkyl group which may be substituted (provided that a heterocyclic methyl group which may be substituted, is excluded), a heterocyclic group which may be substituted or a —A"—$R^{7"}$ group (wherein A" and $R^{7"}$ are as defined above); or $R^T$ and $R^{3'}$ may together form a $N=CR'''R^{9"}$ group (wherein each of $R^{8"}$ and $R^{9"}$ which are independent of each other, is a hydrogen atom, an alkyl group which may be substituted, an aryl group which may be substituted, a heterocyclic group which may be substituted or an alkoxy group which may be substituted) or form a ring containing or not containing a hetero atom;

$R^{4'}$ is an alkylsulfonyl group which may be substituted, an alkenylsulfonyl group which may be substituted, a cycloalkylsulfonyl group which may be substituted, a cycloalkenylsulfonyl group which may be substituted, an arylsulfonyl group which may be substituted, a sulfonyl group substituted by a hetero ring which may be substituted or an amino group which may be substituted; and R" is a hydrogen atom or an alkyl group;

its stereoisomer, its tautomer, or a salt thereof.

4. A process for producing a nitroetheneamine derivative according to claim 3, wherein R" is a hydrogen atom;

R" is a heterocyclic group which may be substituted or a —A'—R" group (wherein A' is CO, $CO_2$ or $SO_2$ and R" is an alkyl group which may be substituted or an aryl group which may be substituted);

$R^{3'}$ is a hydrogen atom, an alkyl group which may be substituted (provided that a heterocyclic methyl group which may be substituted, is excluded), a heterocyclic group which may be substituted or a —A"—R''' group (wherein A" and $R^{7"}$ are as defined above);

or $R^{2'}$ and $R^{3'}$ may together form a $N=CR^{8"}R^{9"}$ group (wherein each of $R^{8"}$ and $R^{9"}$ which are independent of each other, is a hydrogen atom, an alkyl group which may be substituted, an aryl group which may be substituted, a heterocyclic group which may be substituted or an alkoxy group which may be substituted);

$R^{4'}$ is an alkylsulfonyl group which may be substituted, an alkenylsulfonyl group which may be substituted, an alkynylsulfonyl group which may be substituted, a cycloalkylsufonyl group which may be substituted, a cycloalkylsulfonyl group which may be substituted, an arylsulfonyl group which may be substituted, a sulfonyl group substituted by a hetero ring which may be substituted or an amino group which may be substituted; and R'' is a hydrogen atom or an alkyl group;

its stereoisomer, its tatomer, or a salt thereof.

5. A process for producing a nitroetheneamine derivative according to claim 2, wherein R$^{1'}$ is a hydrogen atom;

R$^{2'}$ and R$^{3'}$ together form a ring containing or not containing a hetero atom in addition to the nitrogen atom;

R$^{4'}$ is an alkyl group which may be substituted, an alkoxyphenyl group, a haloaklyloxyphenyl group, a cycloalkyl group which may be substituted, an alkylsulfonyl group which may be substituted, an alkenylsufonyl group which may be substituted, an lakynylsufonyl group which may be substituted, a cycloalkylsufonyl group which may be substituted, a cycloalkenylsulfonyl group which may be substituted, an arylsulfonyl group which may be substituted or a sulfonyl group substituted by a hetero ring which may be substituted; and R$^{6'}$ is a hydrogen atom or an alkyl group;

its stereoisomer, its tautomer or a salt thereof.

* * * * *